United States Patent
Takeda et al.

(10) Patent No.: US 9,617,222 B1
(45) Date of Patent: Apr. 11, 2017

(54) ALKYNYL INDAZOLE DERIVATIVE AND USE THEREOF

(71) Applicant: SENJU PHARMACEUTICAL CO., LTD., Osaka-shi, Osaka (JP)

(72) Inventors: Norihiko Takeda, Kobe (JP); Tomoyo Miyabe, Osaka (JP); Shinnosuke Machida, Osaka (JP); Mamiko Machida, Osaka (JP); Takeshi Nakajima, Osaka (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/126,730

(22) PCT Filed: Mar. 30, 2015

(86) PCT No.: PCT/JP2015/059846
§ 371 (c)(1),
(2) Date: Sep. 16, 2016

(87) PCT Pub. No.: WO2015/152117
PCT Pub. Date: Oct. 8, 2015

(30) Foreign Application Priority Data

Mar. 31, 2014 (JP) .................. 2014-070893

(51) Int. Cl.
*C07D 231/56* (2006.01)
*C07D 401/06* (2006.01)

(52) U.S. Cl.
CPC ......... *C07D 231/56* (2013.01); *C07D 401/06* (2013.01)

(58) Field of Classification Search
None
See application file for complete search history.

(56) References Cited

U.S. PATENT DOCUMENTS 7,232,910 B2 * 6/2007 Ewanicki ............ C07D 401/06
546/275.7

FOREIGN PATENT DOCUMENTS

| WO | 01/02369 A2 | 1/2001 |
|---|---|---|
| WO | 02/10137 A2 | 2/2002 |
| WO | 03/024931 A1 | 3/2003 |
| WO | 2004/056806 A1 | 7/2004 |
| WO | 2005/056519 A1 | 6/2005 |
| WO | 2006/048744 A1 | 5/2006 |
| WO | 2006/048745 A1 | 5/2006 |
| WO | 2009/107753 A1 | 9/2009 |
| WO | 2013/138343 A1 | 9/2013 |
| WO | 2013/138346 A1 | 9/2013 |

OTHER PUBLICATIONS

Cunlong Zhang et al., "Selective VEGFR Inhibitors for Anticancer Therapeutics in Clinical Use and Clinical Trials", Current Pharmaceutical Design, vol. 18, pp. 2921-2935 (2012), Bentham Science Publishers.

* cited by examiner

*Primary Examiner* — Kamal Saeed

(57) ABSTRACT

The main object of the present invention is to provide a novel compound which has a VEGF receptor tyrosine kinase inhibitory activity and is useful as an active ingredient for the treatment of diseases accompanying angiogenesis or edema, for example, age-related macular degeneration or the like.

The present invention includes, for example, an alkynyl indazole derivative represented by the following general formula (I), a pharmaceutical acceptable salt thereof, and a medicine containing thereof.

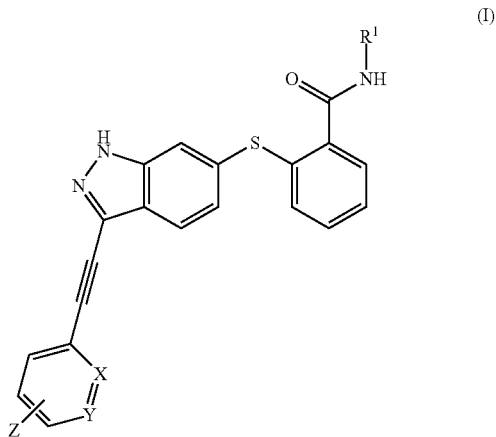

11 Claims, No Drawings

ALKYNYL INDAZOLE DERIVATIVE AND USE THEREOF

CROSS REFERENCE TO RELATED APPLICATIONS

This patent application is a U.S. national stage application under 35 U.S.C. §371 of International Patent Application No. PCT/JP2015/059846 filed on Mar. 30, 2015, which claims the benefit of foreign priority to Japanese Patent Application No. JP 2014-070893 filed on Mar. 31, 2014. The International Application was published in Japanese on Oct. 8, 2015, as International Publication No. WO 2015/152117 A1 under PCT Article 21(2).

The present invention relates to an alkynyl indazole derivative which has a VEGF receptor tyrosine kinase inhibitory activity, a pharmaceutically acceptable salt thereof, and a use thereof.

Although angiogenesis (vasculogenesis) in cells and tissues plays an important role in the process of development, wound healing, etc., pathological angiogenesis is known to be associated with various diseases or conditions such as: retinal diseases like age-related macular degeneration and diabetic retinopathy; formation, proliferation or metastasis of tumor; chronic inflammation; and rheumatoid arthritis.

As a receptor involved in angiogenesis, a VEGF receptor such as a vascular endothelial cell proliferative factor (also referred to as vascular endothelial cell growth factor, and hereinafter, referred to as "VEGF") receptor 2, is known. The VEGF receptor is a kind of receptor tyrosine kinases, and once the VEGF as a ligand binds to the VEGF receptor, and the receptor tyrosine kinase is activated to transmit signals into cells. As a result, for example, vascular permeability, as well as proliferation and migration of vascular endothelial cells are enhanced, and angiogenesis is induced.

The VEGF receptor 2 is involved not only in angiogenesis in a normal body but also in pathological angiogenesis caused by the above-mentioned diseases or conditions. Thus, for example, by inhibiting VEGF receptor 2 tyrosine kinase activity, an angiogenesis caused by the kinase can be inhibited, which is effective for treatment of the diseases or conditions accompanying angiogenesis. Therefore, for the purpose of prevention or treatment of diseases or conditions accompanying angiogenesis, various VEGF receptor 2 tyrosine kinase inhibitors have been developed.

Patent Document 1 discloses indazole compounds which inhibit the protein kinase activity of a VEGF receptor. For example, Example 33 (a) in Patent Document 1 shows (6-[2-(methylcarbamoyl)phenylsulfanyl]-3-E-[2-(pyridine-2-yl) ethenyl]indazole) (generic name: axitinib) that is represented by the following formula.

[Formula 1]

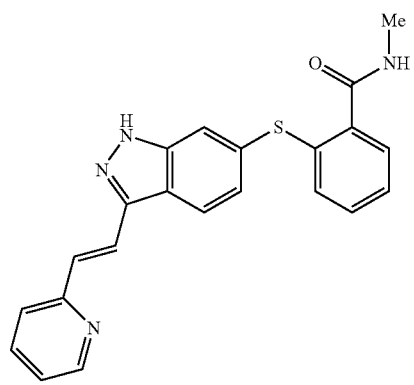

Patent document 2 discloses indazole compounds which are useful as a modulator and/or inhibitor of the protein kinase, and a method for preparing an intermediate thereof. For example, Example 20 shows (6-[2-(methylcarbamoyl) phenylsulfanyl]-3-E-[2-(pyridine-2-yl)ethynyl]indazole) that is represented by the following formula.

[Formula 2]

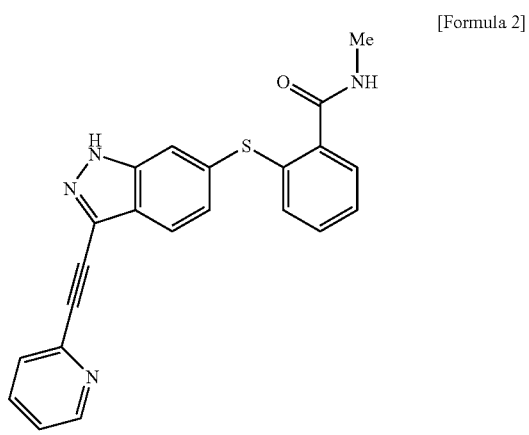 [SMILES: CNC(=O)c1ccccc1Sc1ccc2c(C#Cc3ccccn3)n[nH]c2c1]

Patent document 3 discloses indazole compounds which modulate or inhibit the activity of VEGF receptor 2. Non-Patent document 1 discloses anticancer agents containing a VEGF receptor kinase inhibitor, e.g. pazopanib, axitinib, sorafenib, sunitinib.

Also, as drugs for treatment of age-related macular degeneration which is a posterior eye segment disease, LUCENTIS (registered trademark), MACUGEN (registered trademark) and EYLEA (registered trademark) which are VEGF inhibitors are used. Although these drugs contain high-molecular compounds which specifically bind to VEGF (antibody or aptamer to VEGF), they must be administered into a vitreous body. Thus, for example in the ophthalmological field, development of angiogenesis inhibitors which can be more non-invasively administered is desired. However, an angiogenesis inhibitor which can be instilled into eyes has not yet been marketed.

RELATED ART

Patent Document

[Patent document 1] WO2001/002369
[Patent document 2] WO2006/048745
[Patent document 3] WO2004/056806

Non-Patent Document

[Non-Patent document 1] Current Pharmaceutical Design, 2012, 18, 2921-2935

SUMMARY OF THE INVENTION

Problems to be Solved by the Invention

The main object of the present invention is to provide a novel compound which has a VEGF receptor tyrosine kinase inhibitory activity and is useful as a medicine for the treatment of diseases accompanying angiogenesis or edema, for example, age-related macular degeneration or the like.

Also, another object of the present invention is to provide a compound which has a VEGF receptor tyrosine kinase inhibitory activity, high solubility in an aqueous solution and excellent stability.

As a result of intensive studies for solving the above-mentioned problems, the present inventors found that an alkynyl indazole derivative represented by the following general formula (I) and its salt had an excellent VEGF receptor tyrosine kinase inhibitory activity, and achieved the present invention. The alkynyl indazole derivative represented by the following general formula (I) and its salt had high solubility in an aqueous solution and excellent photostability in the solution.

Axitinib sold as an oral antineoplastic agent is an excellent VEGF receptor inhibitor having a VEGF receptor tyrosine kinase inhibitory activity. When the present inventors examined whether axitinib could be applied for a liquid formulation such as an eye drop, solubility of the compound was low in aqueous solution and it was predicted that transfer to the posterior eyes was insufficient. Furthermore, it was found that axitinib had poor photostability in an aqueous solution. From these points of view, it was difficult to apply axitinib to a liquid formulation such as an eye drop.

The alkynyl indazole derivative represented by the following general formula (1) and its salt have the VEGF receptor tyrosine kinase inhibitory activity as described above, and have an improved solubility in an aqueous solution, furthermore they have excellent photostability in a solution and thus can be suitably used for a liquid formulation such as an eye drop.

The present invention can include the following alkynyl indazole derivative or a pharmaceutically acceptable salt thereof, and a medicine that contains it.

(1) An alkynyl indazole derivative represented by the following general formula (I):

[Formula 3]

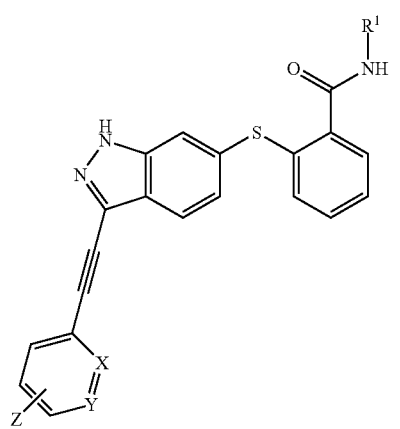

(I)

(In the formula, $R^1$ represents a lower alkyl. X and Y are the same or different and each represents CH or N, with the proviso that X and Y are not simultaneously N. Z is a group represented by the following general formula (a):

[Formula 4]

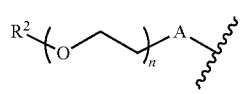

(a)

(In the formula, $R^2$ represents a lower alkyl which may have a substituent. n is an integer of 1 to 7. A is a partial structure represented by the following formula:

[Formula 5]

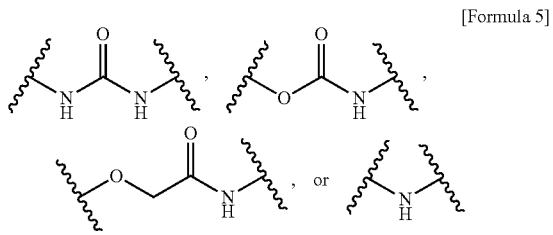

or a pharmaceutically acceptable salt thereof.

(2) The alkynyl indazole derivative according to the above-mentioned (1), or the pharmaceutically acceptable salt thereof, wherein X and Y are simultaneously CH.
(3) The alkynyl indazole derivative according to the above-mentioned (1) or (2), or the pharmaceutically acceptable salt thereof, wherein Z is bound in the para-position.
(4) The alkynyl indazole derivative according to any one of the above-mentioned (1) to (3), or the pharmaceutically acceptable salt thereof, wherein A is a partial structure represented by the following formula:

[Formula 6]

(5) A medicine characterized by containing the alkynyl indazole derivative according to any one of the above-mentioned (1) to (4) or the pharmaceutically acceptable salt thereof.
(6) The medicine according to the above-mentioned (5), which is a vascular endothelial cell growth factor (VEGF) receptor tyrosine kinase inhibitor.
(7) The medicine according to the above-mentioned (5) or (6), which is used for prevention or treatment of a retinal disease accompanying angiogenesis or edema.
(8) The medicine according to the above-mentioned (7), wherein the retinal disease accompanying angiogenesis or edema is age-related macular degeneration, macular edema, diabetic retinopathy, retinopathy of prematurity, retinal vein occlusion, secondary cataract, myopic choroidal neovascularization or glaucoma.

Effects of the Invention

According to the present invention, it is possible to provide an alkynyl indazole derivative represented by the general formula (I), its pharmacologically acceptable salt and a drug containing the alkynyl indazole derivative or its pharmacologically acceptable salt. Since the alkynyl indazole derivative and its pharmacologically acceptable salt of the present invention have excellent VEGF receptor tyrosine kinase inhibitory activities, they are effective for prevention or treatment for diseases or conditions involving the VEGF receptor tyrosine kinase, for example, diseases or conditions accompanying angiogenesis or edema. In addition, the alkynyl indazole derivative and its pharmacologically acceptable salt have not only high solubility in an aqueous solution but also excellent penetrating property to retina or choroid as apparent from the result of Test Example 5 described below. Also, they are excellent in stability, particularly in photostability in a solution. Thus, they can be used in forms of a liquid formulation, for example, an eye drop, an injection, etc.

MODE FOR CARRYING OUT THE INVENTION

The compound of the present invention is an alkynyl indazole derivative represented by the general formula (I) or its pharmacologically acceptable salt. In the present specification, the alkynyl indazole derivative represented by the general formula (I) is also referred to as "compound (I) of the present invention".

In the present invention,

[Formula 7]

is used in a structural formula in order to explain a bond which is a point where a substituent or a partial structure binds to a skeletal structure or another partial structure.

In general formula (I), lower alkyls represented by $R^1$ can include, for example linear, branched or cyclic alkyls having 1 to 4 carbon atoms. Such lower alkyls can include, for example methyl, ethyl, propyl, isopropyl, butyl, isobutyl, sec-butyl, tert-butyl, cyclopropyl and cyclobutyl. $R^1$ is preferably a linear or branched alkyl having 1 to 3 carbon atoms, more preferably an alkyl having 1 or 2 carbon atoms (methyl or ethyl), and in particular preferably methyl.

X and Y are the same or different and each represents CH or N, with the proviso that X and Y are not simultaneously N. Combinations of X and Y can include (i) X and Y are CH, (ii) X is N and Y is CH, and (iii) X is CH and Y is N. Preferably, X and Y are CH.

A binding position in a six-membered ring in the group represented by Z is not particularly limited, and the position may be in any position of an ortho-position, a meta-position or a para-position. Note that the binding position is a position relative to an ethynyl group. Preferably Z is bound in the meta-position or the para-position, and more preferably it is bound in the para-position.

Z is a group represented by the general formula (a). In formula (a), the lower alkyl of a lower alkyl which may have a substituent represented by $R^2$ can include, for example linear, branched or cyclic alkyls having 1 to 4 carbon atoms. Such lower alkyls can include the same lower alkyls as represented by the aforementioned $R^1$. $R^2$ is preferably a linear or branched alkyl having 1 to 3 carbon atoms, more preferably an alkyl having 1 or 2 carbon atoms (methyl or ethyl). The substituent of the lower alkyl which may have a substituent represented by $R^2$ can include, for example hydroxy, amino, dimethylamino, acetylamino and morpholino. Preferable lower alkyls which may have a substituent represented by $R^2$ can include, for example methyl, 2-hydroxyethyl, 2-aminoethyl, 2-(dimethylamino)ethyl, 2-acetylaminoethyl and 2-(N-morpholino)ethyl, and among them, methyl is more preferable.

A in the general formula (a) is a partial structure represented by the following formula.

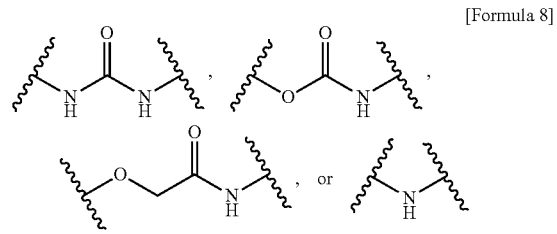

[Formula 8]

The partial structures represented by each formula described above are respectively referred to as urea, carbamate, α-alkoxyamide and amine. In the partial structures represented by each formula described above, their left side binds to a (poly)ethylene glycol moiety ($-(O-CH_2CH_2)n-$, n is the same as defined above) in the general formula (a), and their right side binds to the six-membered ring. For example, if A is carbamate or α-alkoxyamide, oxygen and nitrogen in the above formula bind to the (poly)ethylene glycol moiety and the six-membered ring respectively.

In the general formula (a), A is preferably a partial structure (urea) represented by the following formula:

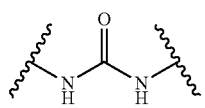

[Formula 9]

In the general formula (a), n is an integer of 1 to 7, preferably an integer of 1 to 5, more preferably an integer of 2 to 5, even more preferably 2 to 4, and in particular preferably 3.

As one of particularly preferred aspects of the compound (I) of the present invention, a compound in which, in the general formula (I), $R^1$ is methyl, X and Y are CH, and in the general formula (a), $R^2$ is methyl, A is urea, n is 3, and Z is bound in the para-position, is exemplified.

The pharmacologically acceptable salts of the compound (I) of the present invention can include, for example pharmacologically acceptable acid addition salts, ammonium salts and amino acid addition salts. For the salt, one kind can be selected and used alone, and two or more kinds can be also combined for use.

The acid addition salts can include inorganic acid salts or organic acid salts. The inorganic acid salts can include, for example inorganic salts of hydrochloride, hydrobromate, hydroiodide, nitrate, sulfate, phosphate. As the inorganic acid salts, hydrochloride or hydrobromate, etc. is preferable, and hydrochloride is more preferable.

The organic acid salts can include, for example organic salts of methanesulfonate, benzensulfonate, p-toluenesulfonate, formate, acetate, trifluoroacetate, oxalate, citrate, malonate, fumarate, glutarate, adipate, ascorbate, maleate, tartrate, mandelate, malate, pantothenate. As the organic acid salts, citrate, fumarate, or tartrate is preferable.

Ammonium salts can include, for example methylpyridinium salt, acetylpyridinium salt. Amino acid addition salts can include, for example addition salts of lysine, glycine, alanine, phenylalanine, glutamic acid, asparagine acid, arginine.

As the pharmaceutically acceptable salts, inorganic acid salts or organic acid salts are preferable, and inorganic acid salts are more preferable. The pharmaceutically acceptable salts may include solvates such as hydrates.

The compound (I) of the present invention or the pharmaceutically acceptable salt thereof has an inhibitory activity of tyrosine kinase. More specifically, the compound (I) of the present invention or the pharmaceutically acceptable salt thereof has an inhibitory activity of VEGF receptor 2 tyrosine kinase.

The compound (I) of the present invention or the pharmaceutically acceptable salt thereof is preferably used as an active ingredient of the VEGF receptor tyrosine kinase inhibitor. The compound is preferably used as an active ingredient of the VEGF receptor 2 tyrosine kinase inhibitor, in particular.

Since the VEGF receptor 2 tyrosine kinase inhibitor has an effect of inhibiting angiogenesis, it is used for treatment of various diseases or conditions accompanying angiogenesis or edema. The diseases or conditions for which the compound (I) of the present invention and its pharmacologically acceptable salt are applied can include, for example diseases and conditions to which the inhibition of the VEGF receptor 2 tyrosine kinase is effective, and for example, diseases, conditions or the like accompanying angiogenesis or edema are suitable.

The diseases or conditions accompanying angiogenesis or edema may specifically include, for example cancer (tumor) (for example, gastric cancer, renal cancer, colon cancer, lung cancer, etc.), retinal diseases accompanying angiogenesis or edema, keratoconjunctive diseases accompanying angiogenesis or edema (keratoconjunctivitis, contact lens disorder, etc.), chronic inflammation, rheumatoid arthritis, inflammatory skin diseases, psoriasis, atherosclerosis and myocardial infarction. The compound (I) of the present invention and its pharmacologically acceptable salt are useful as active ingredients of the drug used for prevention or treatment of such diseases or conditions. Among them, the compound (I) of the present invention and its pharmacologically acceptable salt are suitably used for prevention or treatment of retinal diseases accompanying angiogenesis or edema. The retinal diseases accompanying angiogenesis or edema can include, for example age-related macular degeneration, macular edema, diabetic retinopathy, retinopathy of prematurity, retinal vein occlusion, secondary cataract, myopic choroidal neovascularization and glaucoma.

Note that the term "prevention" means delaying or preventing onsets of conditions or diseases and their accompanying symptoms, or reducing a risk of a subject to develop a condition or a disease. In addition, the term "treatment" means reducing or curing diseases or conditions and/or their accompanying symptoms.

The present invention also encompasses a medicine which contains the compound (I) of the present invention or its pharmacologically acceptable salt.

The compound (I) of the present invention and its pharmacologically acceptable salt can be used as they are or in forms of various formulations according to the purpose of administration. The medicine of the present invention is typically provided as a pharmaceutical composition which contains the compound (I) of the present invention or its pharmacologically acceptable salt and pharmaceutically acceptable carrier.

The medicine of the present invention can be preferably used as a VEGF receptor tyrosine kinase inhibitor, and can be preferably used as a VEGF receptor 2 tyrosine kinase inhibitor, in particular. Additionally, the medicine of the present invention is preferably used for prevention or treatment of various diseases or conditions accompanying angiogenesis or edema.

As a subject to be dosed with the medicine of the present invention, a patient with the disease or condition accompanying angiogenesis or edema is suitable.

Particularly, the medicine is suitably administered to a patient with retinal disease accompanying angiogenesis or edema. Furthermore, in order to prevent the development of the diseases or conditions, the compound (I) of the present invention or its pharmacologically acceptable salt can also be administered to a mammal which may develop the above-mentioned diseases or conditions.

The present invention also encompasses a method for inhibiting the VEGF receptor tyrosine kinase, in which the compound (I) of the present invention or its pharmacologically acceptable salt is administered to a mammal. Also, the present invention encompasses a method for preventing or treating diseases or conditions accompanying angiogenesis or edema (preferably, retinal diseases accompanying angiogenesis or edema), in which the compound (I) of the present invention or its pharmacologically acceptable salt is administered to a mammal.

The medicine of the present invention can be orally or parenterally administered to humans or mammals other than humans. The mammals other than humans can include, for example mice, rats, hamsters, guinea pigs, rabbits, cats, dogs, swine, cattle, horses, sheep and monkeys.

In use of the medicine of the present invention for the purpose of prevention or treatment of diseases or conditions accompanying angiogenesis or edema, generally the medicine can be systemically or topically, orally or parenterally administered. For its administration route, a route which is most effective for treatment is preferably selected. In the case of systemic administration, in addition to by oral administration, it is administered by parenteral administrations such as intravenous injection, subcutaneous injection and intramuscular injection. In the case of local administration, it is administered into, for example, skin, mucosa, lung, bronchus, nasal cavity, nasal mucosa, ocular surface or eyes. Formulations for oral administration can include, for example powders, granules, tablets, capsules, syrups and liquid formulations. Formulations for parenteral administration can include, for example injections, ointments, gels, creams, fomentations, patches, liniments, suppositories, aerosols, inhalants, sprays, eye drops (ophthalmic solutions) and nasal drops. For example, when the medicine of the present invention is applied to eye disease such as retinal disease, parenteral administration is preferable, and in particular, administration as an eye drop is preferable.

The compound (I) of the present invention and its pharmacologically acceptable salt have high solubility in aqueous solutions. Furthermore, the compound (I) of the present invention and its pharmacologically acceptable salt have excellent stability in solutions, particularly have excellent photostability. Accordingly, the compound (I) of the present invention and its pharmacologically acceptable salt can be suitably used for a formulation containing an aqueous solution, preferably a liquid-form formulation containing the aqueous solution as a base. The compound of the present invention or its pharmacologically acceptable salt can be suitably used, for example, for formulations mentioned above such as particularly syrups, injections, eye drops, nasal drops, etc., and among them, eye drops are particularly suitable.

The medicine of the present invention can be produced according to a method known per se in the technical field of pharmaceutical formulations, in which conventionally the compound (I) of the present invention or its pharmacologically acceptable salt is mixed with at least one pharmacologically acceptable carrier or the like. The carrier may be arbitrarily selected depending on the form of the formulation preferable for administration. The content of the compound (I) of the present invention or its pharmacologically acceptable salt in the medicine varies depending on its dosage form, dose and the like, and can be arbitrarily selected. For example, the content may be typically 0.01 to 99.9 mass %, preferably 0.1 to 80 mass % of the total amount of the medicine.

As the pharmacologically acceptable carrier, various organic or inorganic carrier substances which are conventionally used as formulation materials can be used, and they can include, for example: excipients, disintegrators, binders, plasticizers, lubricants, etc. in solid formulations; solvents, solubilizing agents, suspending agents, stabilizers, isotonizing agents, buffers, thickeners, pH adjusters, soothing agents, etc. in liquid formulations. Furthermore, additives such as preservatives, antioxidants, colorants and sweeteners may be used as necessary. The solid formulation may be coated with a coating agent. Only one kind or a combination of two or more kinds of carriers and additives may be used.

The excipients can include, for example lactose, sucrose, D-mannitol, D-sorbitol, starch, dextrin, microcrystalline cellulose, crystalline cellulose, carmellose, carmellose calcium, carboxymethyl starch sodium, low-substituted hydroxypropylcellulose, acacia.

The disintegrators can include, for example carmellose, carmellose calcium, carmellose sodium, carboxymethyl starch sodium, croscarmellose sodium, crospovidone, low-substituted hydroxypropylcellulose, hydroxypropylmethylcellulose, crystalline cellulose.

The binders can include, for example hydroxypropylcellulose, hydroxypropylmethylcellulose, povidone, crystalline cellulose, sucrose, dextrin, starch, gelatin, carmellose sodium, acacia.

The plasticizers can include, for example light anhydrous silicic acid, magnesium stearate.

The lubricants can include, for example magnesium stearate, calcium stearate, talc.

The coating agents can include, for example gelatin, sucrose.

The solvents can include, for example purified water, distilled water for injection, physiological saline solution, ethanol, propylene glycol, macrogol, sesame oil, corn oil, olive oil.

The solubilizing agents can include, for example propylene glycol, D-mannitol, benzyl benzoate, ethanol, triethanolamine, sodium carbonate, sodium citrate, polysorbate 80.

The suspending agents can include, for example benzalkonium chloride, carmellose, hydroxypropylcellulose, propylene glycol, povidone, methylcellulose, glycerin mono stearate.

The stabilizers can include, for example sodium edetate, sodium hydrogen sulfite, sodium thiosulfate, sodium citrate, ascorbic acid, dibutyl hydroxytoluene.

The isotonizing agents can include, for example sodium chloride, potassium chloride, glycerin, mannitol, sorbitol, boric acid, borax, glucose, propylene glycol.

The buffers can include, for example sodium hydrogen phosphate, sodium acetate, sodium carbonate, sodium citrate, boric acid, borax.

The thickeners can include, for example hydroxyethylcellulose, hydroxypropylcellulose, polyvinyl alcohol, polyethylene glycol.

The pH adjusters can include, for example hydrochloric acid, citric acid, sodium hydroxide, phosphoric acid, acetic acid, boric acid.

The soothing agents can include, for example benzyl alcohol.

The preservatives can include, for example benzalkonium chloride, methyl parahydroxybenzoate, ethyl parahydroxybenzoate, propyl parahydroxybenzoate, chlorobutanol, benzylalcohol, sodium dehydroacetate, sorbic acid.

The antioxidants can include, for example sodium sulfite, ascorbic acid.

The colorants can include, for example edible dye (for example, food red No. 2, or No. 3), beta-carotene.

The sweeteners can include, for example saccharine sodium, dipotassium glycyrrhizinate, aspartame.

The medicine of the present invention can contain one or a plurality of any other medicinal ingredients unless the effects of the present invention are impaired.

The dose of the compound (I) of the present invention or its pharmacologically acceptable salt varies depending on diseases or conditions and subjects to be treated, and medication methods, but for example, when it is administered to an adult, a dose is typically 1 ng to 1000 mg, preferably 1 to 200 mg in oral administration. This dose can be administered typically once to 4 times per a day. In the case of parenteral administration, the dose is typically, for example 1 ng to 1000 mg, preferably 1 to 200 mg. This dose can be administered typically once to 4 times per a day. In addition, for example in the case of topical administration to eyes, it is preferable that an eye drop typically containing 0.001 to 10 w/v %, preferably 0.01 to 1 w/v % of the compound (I) of the present invention or its pharmacologically acceptable salt is instilled in eyes, in an amount of 5 to 100 µL, preferably 30 to 60 µL per a dose, about once to 6 times per a day.

Next, a method for producing the compound (I) of the present invention will be explained. The following producing method is an example of a producing method of the compound (I) of the present invention, and the producing method of the compound of the present invention is not limited thereto.

Even if there is no particular description in the following producing method, the production can be efficiently carried out by: a device to introduce a protecting group to a functional group as necessary and carry out deprotection in a subsequent step; a device to provide a functional group as a precursor in each step and convert it into a desired functional group at an appropriate stage; a device to change the order of each process and step; etc.

Additionally, in each step or reaction, the post-reaction treatment can be carried out by a conventional method. The compounds obtained in each step or reaction can be used for the subsequent reaction in a state of a reaction liquid or as a crude product. The product can be isolated from a reaction mixture according to a routine procedure. The product can be isolated or purified by arbitrarily selecting a conventional method such as crystallization, recrystallization, distillation, separation and chromatography, and by combining them, as necessary.

The compound (I) of the present invention can be produced by, for example, the method shown in the following reaction formula 1 or methods based on it.

[Formula 10]

(Reaction formula 1)

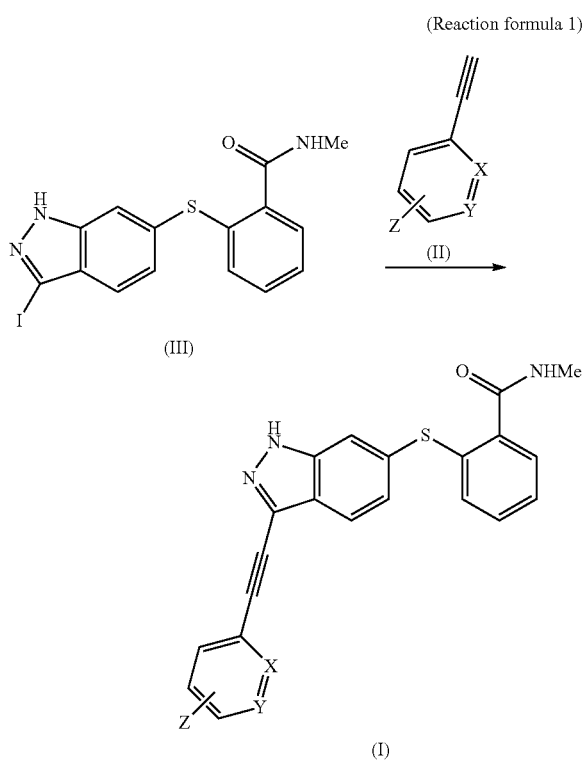

The symbols in the formula are the same as described in general formula (I). Me represents methyl.

The compound (I) of the present invention can be produced by reacting a compound represented by general formula (II) (hereinafter, referred to as "compound (II)") with a compound represented by formula (III) (hereinafter, referred to as "compound (III)") in the presence of a base and a catalyst. Relative to the compound (III), typically 0.5 to 3 equivalents, preferably 0.8 to 2 equivalents of the compound (II) are used.

The base can include, for example N,N-diisopropylethylamine, triethylamine, diethylamine, diisopropylamine, etc., and among them, N,N-diisopropylethylamine or triethylamine is preferable. Relative to the compound (III), typically 1 to 50 equivalents, preferably 3 to 30 equivalents of this base are used.

The catalyst can include, for example $PdCl_2(PPh_3)_2$, $Pd(PPh_3)_4$, copper iodide, copper bromide, etc., and among them, $PdCl_2(PPh_3)_2$ and copper iodide are preferable. Relative to the compound (III), typically 0.01 to 0.5 equivalent, preferably 0.03 to 0.1 equivalent of this catalyst is used.

This reaction is preferably carried out in a solvent inert to the reaction. Although such a solvent is not particularly limited as long as the reaction proceeds, it can include, for example N,N-dimethylformamide, acetonitrile, tetrahydrofuran, 1,4-dioxane, 1,2-dimethoxyethane, toluene, ethyl acetate, etc., and among them, N,N-dimethylformamide or acetonitrile is preferable.

Although the reaction time varies depending on reagents or solvents to be used, it is typically 1 to 24 hours, preferably 2 to 4 hours. Although the reaction temperature varies depending on reagents or solvents to be used, it is typically 25 to 160° C., preferably 60 to 100° C.

When A in general formula (a) is urea or carbamate in the group represented by Z, the compound (II) can be produced by the method represented by the following reaction formula 2. A compound represented by general formula (II-1) (hereinafter, referred to as "compound (II-1)") and a compound represented by general formula (II-2) (hereinafter, referred to as "compound (II-2)") are encompassed in compound (II).

[Formula 11]

(Reaction formula 2)

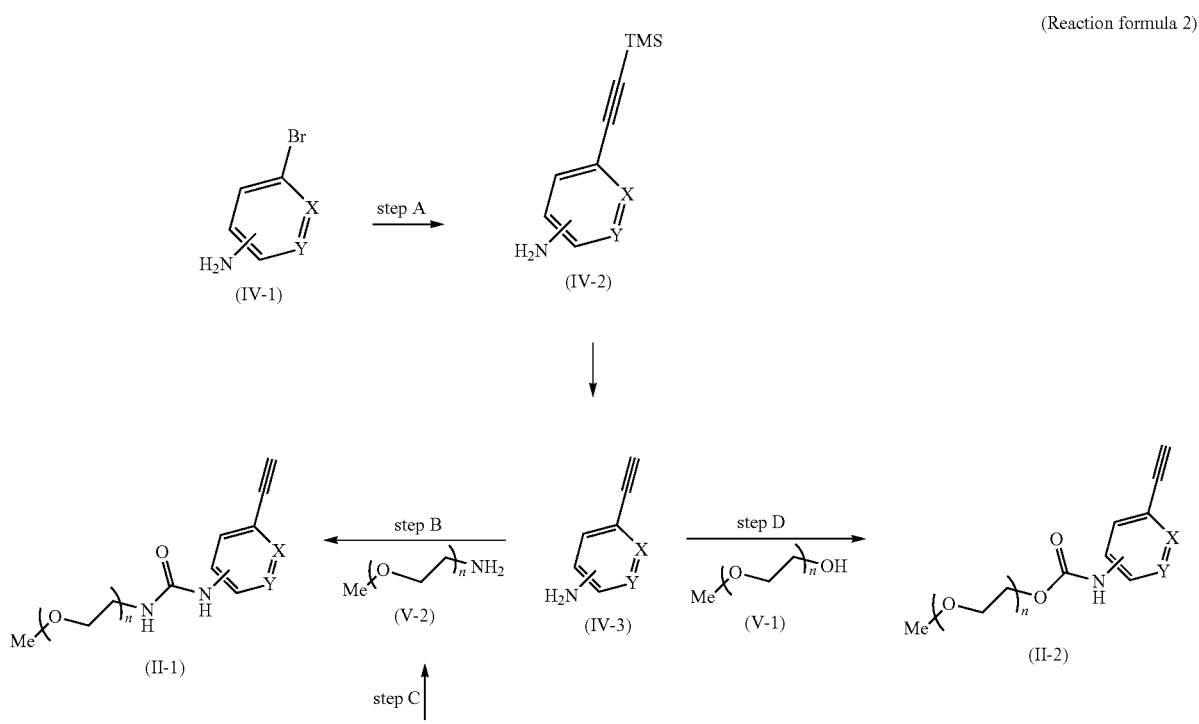

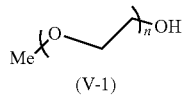

(V-1)

The symbols in the formula are the same as described in general formula (I). TMS represents a trimethylsilyl group. Me represents methyl.

A compound represented by general formula (IV-3) (hereinafter, referred to as "compound (IV-3)") is commercially available, and commercial products can be used. In addition, compound (IV-3) can be produced according to a method known per se, for example, methods described in WO2013/101184, WO2011/092197 or the like, or methods based on them, for example step A described below.

In step A, a compound represented by general formula (IV-2) (hereinafter, referred to as "compound (IV-2)") is produced by reacting a compound represented by general formula (IV-1) (hereinafter, referred to as "compound (IV-1)") with trimethylsilyl acetylene in a solvent in the presence of a base and a catalyst, and subsequently a trimethylsilyl group of the compound (IV-2) is deprotected to produce the compound (IV-3). In the reaction related to step A, relative to the compound (IV-1), typically 1 to 3 equivalents, preferably 1.2 to 1.5 equivalents of trimethylsilyl acetylene are used. The base can include the same bases as exemplified in reaction formula 1, preferably triethylamine. Relative to the compound (IV-1), typically 1 to 30 equivalents, preferably 10 to 20 equivalents of this base are used. The catalyst can include the same catalysts as exemplified in reaction formula 1, and preferably $PdCl_2(PPh_3)_2$ and copper iodide are used. Relative to the compound (IV-1), typically 0.01 to 0.2 equivalent, preferably 0.02 to 0.05 equivalent of each of these catalysts is used. The solvent can include the same solvent as exemplified in reaction formula 1, preferably tetrahydrofuran. Although the reaction time varies depending on reagents or solvents to be used, it is typically 1 to 24 hours, preferably 3 to 4 hours. Although the reaction temperature varies depending on reagents or solvents to be used, it is typically 25 to 120° C., preferably 60 to 90° C. Furthermore, a trimethylsilyl group of the obtained compound (IV-2) is deprotected with a methanol solution with the addition of bases, allowing production of the compound (IV-3). A concentration of the bases in the methanol solution is typically 5 to 50 w/v %, preferably 10 to 15 w/v %. This base can include, for example sodium hydroxide, potassium hydroxide, lithium hydroxide, potassium carbonate, cesium carbonate, etc., and among them, sodium hydroxide is preferable. Although the reaction temperature and the reaction time for deprotection vary depending on reagents or solvents to be used, the reaction temperature is typically 1 to 30° C., preferably 15 to 25° C., and the reaction time is typically 1 to 24 hours, preferably 2 to 4 hours.

In step B, the compound (IV-3) is reacted with 4-nitrophenyl chloroformate in a solvent to form a carbamate product, and then this carbamate product is reacted with a compound represented by general formula (V-2) (hereinafter, referred to as "compound (V-2)") to produce the compound (II-1). Relative to the compound (IV-3), typically 0.8 to 10 equivalents, preferably 1 to 1.3 equivalents of 4-nitrophenyl chloroformate are used. Instead of 4-nitrophenyl chloroformate, 2,2,2-trichloroethyl chloroformate, bis(trichloromethyl)carbonate, 1,1'-carbonyldiimidazole, phenyl chloroformate, di(N-succinimidyl)carbonate, etc. may be used. Also a base may be used as necessary. This base can include, for example triethylamine, tributylamine, N,N-diisopropylethylamine, pyridine, 4-dimethylaminopyridine, etc., and among them, triethylamine or pyridine is preferable. Relative to the compound (IV-3), typically 1 to 30 equivalents, preferably 1 to 5 equivalents of the base are used. The solvent is not particularly limited unless it adversely affects the reaction, and can include dichloromethane, chloroform, tetrahydrofuran, 1,4-dioxane, ethyl acetate, N,N-dimethylformamide, dimethyl sulfoxide, acetonitrile, etc., and among them, dichloromethane, tetrahydrofuran or 1,4-dioxane is preferable. Relative to the compound (IV-3), typically 1 to 5 equivalents, preferably 1 to 3 equivalents of the compound (V-2) are used. Although the reaction time varies depending on reagents or solvents to be used, it is typically 1 to 48 hours, preferably 2 to 24 hours. Although the reaction temperature varies depending on reagents or solvents to be used, it is typically 0 to 120° C., preferably 25 to 110° C. Compound (V-2) is commercially available and commercial products can be used. In addition, compound (V-2) can be produced according to a method known per se, for example a method described in WO2009/109035 (JP 2011-105735 A), or methods based on them, for example step C described below.

In step C, the compound (V-2) is produced from a compound represented by general formula (V-1) (hereinafter, referred to as "the compound (V-1)"). First, the compound (V-1) is reacted with phthalimide, triphenylphosphine and diethyl azodicarboxylate in a solvent (first step). Then, a product obtained in the solvent can be reacted with hydrazine monohydrate to obtain the compound (V-2) (second step).

In the first step, relative to the compound (V-1), typically 0.5 to 2 equivalents, preferably 1 to 1.2 equivalents of phthalimide, typically 0.5 to 2 equivalents, preferably 1 to 1.2 equivalents of triphenylphosphine, as well as typically 0.5 to 2 equivalents, preferably 1 to 1.2 equivalents of diethyl azodicarboxylate are used. Instead of diethyl azodicarboxylate, bis(2-methoxyethyl) azodicarboxylate, diisopropyl azodicarboxylate, cyanomethylene tributylphosphorane or the like may be used. The solvent is not particularly limited unless it adversely affects the reaction, and can include, for example dichloromethane, 1,4-dioxane, tetrahydrofuran, toluene, N,N-dimethylformamide, etc., and among them, tetrahydrofuran is preferable. Although the reaction time varies depending on reagents or solvents to be used, it is typically 5 to 20 hours, preferably 12 to 18 hours. Although the reaction temperature varies depending on reagents or solvents to be used, it is typically 0 to 40° C., preferably 0 to 25° C.

In the second step, relative to the compound (V-1) used in the first step, typically 0.5 to 3 equivalents, preferably 1 to 2.2 equivalents of hydrazine monohydrate are used for the product obtained in the first step. The solvent is not particularly limited unless it adversely affects the reaction, and can include, for example methanol, ethanol, isopropanol, etc., and among them, ethanol is preferable. Although the reaction time varies depending on reagents or solvents to be used, it is typically 2 to 20 hours, preferably 4 to 18 hours.

Although the reaction temperature varies depending on reagents or solvents to be used, it is typically 25 to 120° C., preferably 80 to 100° C.

In step D, the compound (V-1) was reacted with di(N-succinimidyl) carbonate in a solvent in the presence of base to form a carbonate product, and then this carbonate product is condensed with the compound (IV-3) to produce the compound (II-2). Relative to the compound (V-1), typically 0.5 to 5 equivalents, preferably 2 to 3.5 equivalents of the base and typically 0.5 to 5 equivalents, preferably 1 to 2 equivalents of di(N-succinimidyl) carbonate are used. Instead of the di(N-succinimidyl) carbonate, bis(trichloromethyl)carbonate, 1,1'-carbonyldiimidazole, 4-nitrophenylchloroformate, phenyl chloroformate, etc. may be used. The bases can include, for example triethylamine, tributylamine, pyridine, N,N-diisopropylethylamine, 4-dimethylaminopyridine, etc., and among them, triethylamine is preferable. In addition, a reaction accelerator may be used as necessary. This reaction accelerator can include, for example 4-dimethylaminopyridine, 4-pyrrolidinopyridine, etc., and among them, 4-dimethylaminopyridine is preferable. Relative to the compound (V-1), typically 0.05 to 0.5 equivalent, preferably 0.1 to 0.2 equivalent of the reaction accelerator is used. In addition, relative to the compound (IV-3), typically 0.5 to 5 equivalents, preferably 1 to 2 equivalents of the compound (V-1) are used. The solvent is not particularly limited unless it adversely affects the reaction, and can include, for example dichloromethane, chloroform, tetrahydrofuran, 1,4-dioxane, acetonitrile, ethyl acetate, N,N-dimethylformamide, etc., and among them, ethyl acetate is preferable. Although the reaction time varies depending on reagents or solvents to be used, it is typically 1 to 48 hours, preferably 10 to 24 hours. Although the reaction temperature varies depending on reagents or solvents to be used, it is typically 0 to 100° C., preferably 60 to 80° C.

When A in general formula (a) is α-alkoxy amide or amine in the group represented by Z, the compound (II) can be produced by for example a method represented by the following reaction formula 3. A compound represented by general formula (II-3) (hereinafter, referred to as "compound (II-3)") and a compound represented by general formula (II-4) (hereinafter, referred to as "compound (II-4)") are encompassed in the compound (II).

[Formula 12]

(Reaction formula 3)

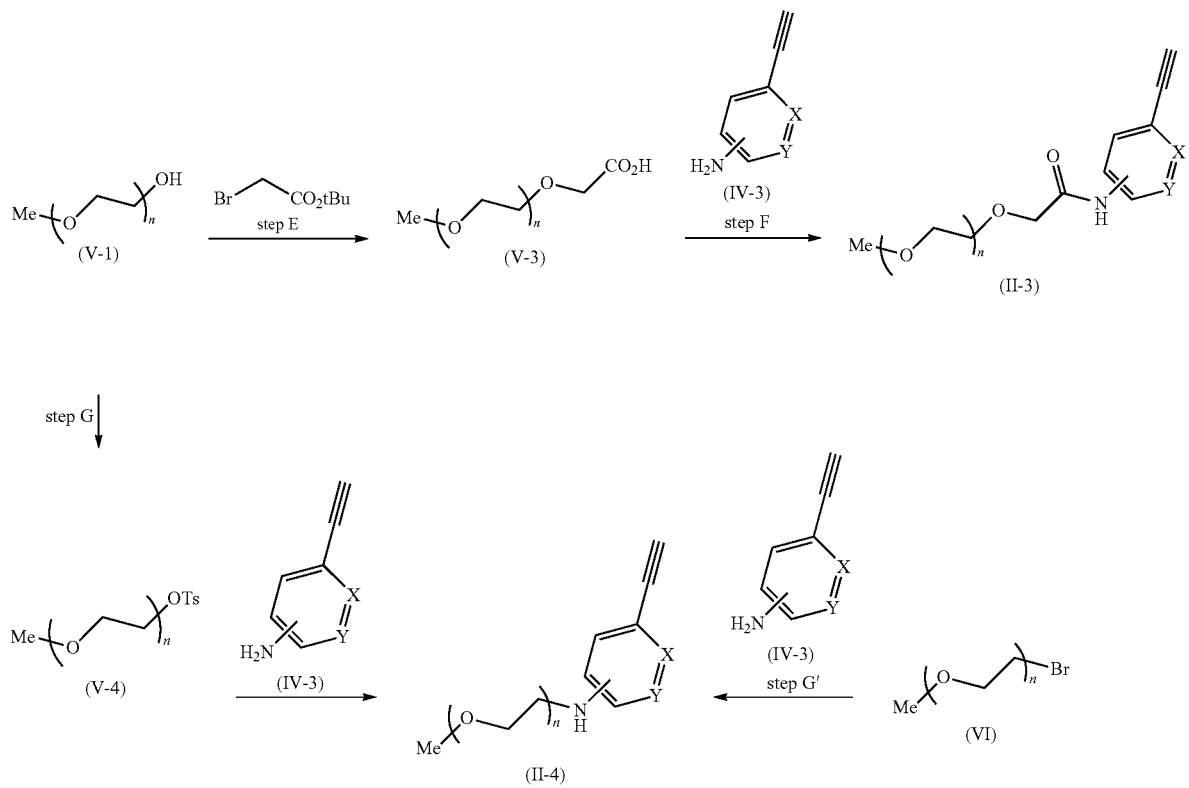

The symbols in the formula are the same as described in general formula (I). Ts represents a p-toluenesulfonyl group (tosyl group). Me represents methyl, and tBu represents tert-butyl.

In step E, the compound (V-1) is reacted with tert-butyl bromoacetate in a conventional solvent in the presence of a base, and then a compound represented by general formula (V-3) (hereinafter, referred to as "compound (V-3)") is produced by hydrolysis of the ester. Relative to the compound (V-1), typically 1 to 5 equivalents, preferably 2 to 3 equivalents of the base, and typically 1 to 3 equivalents, preferably 1 to 1.2 equivalents of tert-butyl bromoacetate are used. The base can include, for example sodium hydride, lithium diisopropylamide, lithium hexamethyldisilazide, n-butyllithium, etc., and among them, sodium hydride is preferable. Instead of the tert-butyl bromoacetate, methyl chloroacetate, ethyl chloroacetate, methyl bromoacetate, ethyl bromoacetate, etc. may also be used. The solvent is not particularly limited unless it adversely affects the reaction, and can include, for example N,N-dimethylformamide, toluene, diethyl ether, 1,2-dimethoxyethane, tetrahydrofuran, etc., and among them, tetrahydrofuran is preferable. Although the reaction time varies depending on reagents or solvents to be used, it is typically 1 to 24 hours, preferably 10 to 17 hours. Although the reaction temperature varies depending on reagents or solvents to be used, it is typically 0 to 100° C., preferably 0 to 25° C.

The hydrolysis of the ester is carried out in a conventional solvent in the presence of a base. In the hydrolysis of the ester, relative to the ester, typically 1 to 5 equivalents, preferably 2 to 4 equivalents of the base are used. The base can include, for example lithium hydroxide, sodium hydroxide, potassium hydroxide, etc., and among them, lithium hydroxide is preferable. The solvent is not particularly limited unless it adversely affects the reaction, and can include, for example mixed solvents of organic solvents (for example, acetonitrile, 1,4-dioxane, tetrahydrofuran, etc.) and water, and among them, a mixed solvent of tetrahydrofuran and water is preferable. Although the reaction time varies depending on reagents or solvents to be used, it is typically 1 to 24 hours, preferably 3 to 5 hours. Although the reaction temperature varies depending on reagents or solvents to be used, it is typically 0 to 100° C., preferably 60 to 100° C.

In step F, the compound (V-3) is reacted with the compound (IV-3) in a conventional solvent in the presence of a base and a condensation agent to produce the compound (II-3). Relative to the compound (IV-3), typically 0.1 to 3 equivalents, preferably 0.5 to 1.2 equivalents of the compound (V-3) are used. In addition, relative to the compound (IV-3), typically 1 to 3 equivalents, preferably 1 to 2 equivalents of the condensation agent, and typically 0.5 to 5 equivalents, preferably 2 to 4 equivalents of the base are used. The condensation agent can include, for example N,N'-dicyclohexylcarbodiimide, 1,1'-carbonyldiimidazole, 1-ethyl-3-[3-(dimethylamino)propyl] carbodiimide hydrochloride, benzotriazol-1-yloxytripyrrolidinophosphonium hexafluorophosphate, 0-(benzotriazol-1-yl)-N,N,N',N'-tetramethyluronium hexafluorophosphate, 0-(7-azabenzotriazol-1-yl)-N,N,N',N'-tetramethyluronium hexafluorophosphate, diethyl cyanophosphonate, diphenylphosphoryl azide, pentafluorophenyl trifluoroacetate ester, isopropyl chloroformate, etc., and among them, 1-ethyl-3-[3-(dimethylamino)propyl]carbodiimide hydrochloride or O-(7-azabenzotriazol-1-yl)-N,N,N',N'-tetramethyluronium hexafluorophosphate is preferable. The bases can include, for example triethylamine, pyridine, N,N-diisopropylethylamine, 4-dimethylaminopyridine, etc., and among them, triethylamine, N,N-diisopropylethylamine or 4-dimethylaminopyridine is preferable. The solvent is not particularly limited unless it adversely affects the reaction, and can include, for example dichloromethane, chloroform, tetrahydrofuran, 1,4-dioxane, 1,2-dimethoxyethane, diethyl ether, acetonitrile, N,N-dimethylformamide, etc., and among them, dichloromethane or N,N-dimethylformamide is preferable. Although the reaction time varies depending on reagents or solvents to be used, it is typically 1 to 24 hours, preferably 3 to 24 hours. Although the reaction temperature varies depending on reagents or solvents to be used, it is typically 0 to 100° C., preferably 25 to 40° C.

In step G, first, the compound (V-1) is reacted with p-toluenesulfonyl chloride in a conventional solvent in the presence of a base to produce a compound represented by general formula (V-4) (hereinafter, referred to as "compound (V-4)"). Then, the compound (V-4) is reacted with the compound (IV-3) in a conventional solvent in the presence of a base to produce the compound (II-4).

Relative to the compound (V-1), typically 1 to 2.2 equivalents, preferably 1.2 to 1.5 equivalents of p-toluenesulfonyl chloride are used. Relative to the compound (V-1), typically 1 to 5 equivalents, preferably 1.5 to 3 equivalents of the base are used. The base can include, for example pyridine, triethylamine, N,N-diisopropylethylamine, 4-dimethylaminopyridine, etc., and among them, triethylamine is preferable. The solvent is not particularly limited unless it adversely affects the reaction, and can include, for example dichloromethane, chloroform, tetrahydrofuran, 1,4-dioxane, 1,2-dimethoxyethane, etc., and among them, dichloromethane is preferable. Although the reaction time varies depending on reagents or solvents to be used, it is typically 1 to 24 hours, preferably 14 to 21 hours. Although the reaction temperature varies depending on reagents or solvents to be used, it is typically 0 to 100° C., preferably 25 to 50° C.

In the reaction of the compound (V-4) and the compound (IV-3), relative to the compound (V-3), typically 0.3 to 5 equivalents, preferably 0.5 to 4.5 equivalents of the compound (V-4) are used. Relative to the compound (IV-3), typically 1 to 5 equivalents, preferably 1.5 to 3 equivalents of the base are used. The base can include, for example sodium hydroxide, potassium hydroxide, cesium carbonate, potassium carbonate, etc., and among them, cesium carbonate or potassium carbonate is preferable. In the reaction of the compound (V-4) and the compound (IV-3), it is preferable to use a reaction accelerator. Relative to the compound (IV-3), typically 0.1 to 3 equivalents, preferably 0.2 to 1 equivalent of this reaction accelerator is used. The reaction accelerator can include, for example sodium iodide, potassium iodide, tetrabutylammonium iodide, etc., and among them, potassium iodide is preferable. The solvent is not particularly limited unless it adversely affects the reaction, and can include, for example acetonitrile, tetrahydrofuran, dichloromethane, N,N-dimethylformamide, dimethylsulfoxide, etc., and among them, acetonitrile or N,N-dimethylformamide is preferable. Although the reaction time varies depending on reagents or solvents to be used, it is typically 9 to 60 hours, preferably 18 to 24 hours. Although the reaction temperature varies depending on reagents or solvents to be used, it is typically 25 to 120° C., preferably 80 to 120° C.

In the reaction of the compound (V-4) and the compound (IV-3), the compound (II-4) can also be produced by using, instead of the compound (V-4), a compound represented by general formula (VI) (hereinafter referred to as "compound (VI)"), which is shown in step G' in reaction formula 3. Preferred conditions and the like for the reaction of the compound (VI) and the compound (IV-3) according to the step G' are the same as those for the reaction of the compound (V-4) and the compound (IV-3) according to the above-mentioned step G.

The compound (III) can be produced according to methods described in known methods, for example methods described in WO 2006/048745 (JP 2008-518901 A), WO 2001/002369 (JP Patent No. 3878849), etc. or methods based thereon, for example the following reaction formula 4.

[Formula 13]

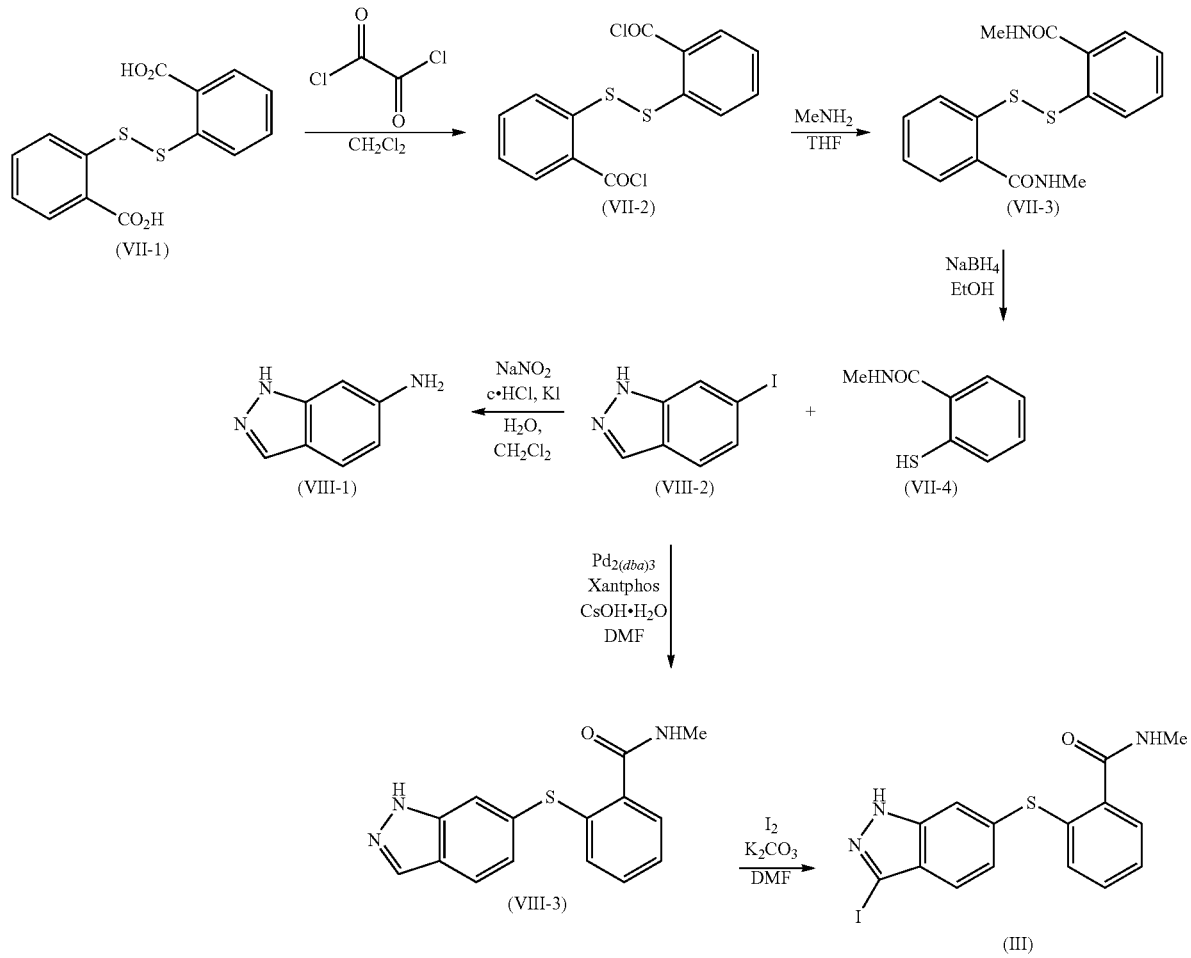

(Reaction formula 4)

In the formula, Me represents methyl.

In the method of reaction formula 4, a compound represented by the formula (VII-1) (hereinafter, referred to as "compound (VII-1)") is reacted with oxalyl chloride in a conventional solvent to form an acid chloride represented by formula (VII-2) (hereinafter, referred to as "acid chloride (VII-2)"), which is then reacted with methylamine to obtain an amide product represented by formula (VII-3) (hereinafter, referred to as "amide product (VII-3)"). The amide product represented by formula (VII-3) can be reduced with sodium borohydride to obtain a thiol product represented by formula (VII-4) (hereinafter, referred to as "thiol product (VII-4)").

Relative to the compound (VII-1), typically 1 to 5 equivalents, preferably 2 to 4 equivalents of oxalyl chloride are used. The solvent is not particularly limited unless it adversely affects the reaction, and can include, for example tetrahydrofuran, dichloromethane, toluene, etc., and among them, dichloromethane is preferable. In the reaction of the compound (VII-1) with oxalyl chloride, it is preferable to use a reaction accelerator. Relative to the compound (VII-1), typically 0.01 to 0.5 equivalent, preferably 0.01 to 0.1 equivalent of this reaction accelerator is used. The reaction accelerator can include N,N-dimethylformamide. Although the reaction time varies depending on solvents to be used, it is typically 10 to 60 hours, preferably 15 to 40 hours. Although the reaction temperature varies depending on solvents, it is typically 15 to 100° C., preferably 20 to 80° C.

The reaction of the acid chloride (VII-2) with methylamine can be carried out, for example in tetrahydrofuran. Relative to the acid chloride (VII-2), typically 1 to 5 equivalents, preferably 2 to 5 equivalents of methylamine are used. The reaction time is typically 6 to 24 hours, preferably 12 to 24 hours. The reaction temperature is typically 0 to 100° C., preferably 0 to 30° C.

In the reduction of the amide product (VII-3), relative to the amide product (VII-3), typically 1 to 5 equivalents, preferably 1 to 3 equivalents of sodium borohydride are used. The reaction may be carried out, for example in ethanol. The reaction time is typically 6 to 24 hours, preferably 12 to 20 hours. The reaction temperature is typically 0 to 50° C., preferably 0 to 30° C.

On the other hand, a compound represented by formula (VIII-1) (hereinafter, referred to as "compound (VIII-1)") can be reacted with sodium nitrite and then with potassium iodide in an acidic aqueous solution to obtain a compound represented by formula (VIII-2) (hereinafter, referred to as "compound (VIII-2)"). This compound (VIII-2) can be reacted in the presence of a thiol product (VII-4), $Pd_2(dba)_3$, 4,5-bis(diphenylphosphino)-9,9-dimethylxanthene and cesium hydroxide monohydrate to obtain a compound represented by formula (VIII-3) (hereinafter, referred to as "compound (VIII-3)"). Subsequently, this compound (VIII-3) can be iodized in the presence of potassium carbonate to produce the compound (III).

In the reaction for obtaining the compound (VIII-2) from the compound (VIII-1), relative to the compound (VIII-1), typically 1 to 5 equivalents, preferably 1 to 3 equivalents of sodium nitrite, and typically 1 to 5 equivalents, preferably 1 to 3 equivalents of potassium iodide are used. The reaction time of the compound (VIII-1) with sodium nitrite is typically 10 minutes to 6 hours, preferably 0.5 hour to 2 hours. The reaction temperature is typically 0 to 50° C., preferably 0 to 30° C. The reaction time with potassium iodide is typically 10 minutes to 6 hours, preferably 0.5 hour to 3 hours. The reaction temperature is typically 0 to 50° C., preferably 0 to 40° C.

The reaction for obtaining the compound (VIII-3) from the compound (VIII-2) and the thiol product (VII-4) can be carried out under an argon gas atmosphere, for example in N,N-dimethylformamide. Relative to the compound (VIII-2), typically 1 to 5 equivalents, preferably 1 to 3 equivalents of the thiol product (VII-4) are used. Relative to the compound (VIII-2), typically 0.01 to 3 equivalents, preferably 0.03 to 1 equivalent of $Pd_2(dba)_3$ is used. Relative to the compound (VIII-2), typically 0.05 to 3 equivalents, preferably 0.1 to 2 equivalents of 4,5-bis(diphenylphosphino)-9,9-dimethylxanthene are used. Relative to compound (VIII-2), typically 1 to 5 equivalents, preferably 1 to 3 equivalents of cesium hydroxide monohydrate are used. The reaction time is typically 1 to 24 hours, preferably 2 to 10 hours. The reaction temperature is typically 25 to 150° C., preferably 80 to 120° C.

Iodization of the compound (VIII-3) can be carried out, for example in N,N-dimethylformamide. Relative to the compound (VIII-3), typically 1 to 5 equivalents, preferably 1 to 3 equivalents of potassium carbonate are used. Relative to the compound (VIII-3), typically 1 to 5 equivalents, preferably 1 to 3 equivalents of iodine are used. The reaction time is typically 1 to 24 hours, preferably 1 to 6 hours. It is typically 0 to 50° C., preferably 0 to 30° C.

When A in general formula (a) is urea and $R^2$ is a lower alkyl which may be substituted in the group represented by Z, the compound (II) can be produced by a method shown in the following reaction formula 5. A compound represented by formula (II-5) (hereinafter, referred to as "compound (II-5)"), a compound represented by formula (II-6) (hereinafter, referred to as "compound (II-6)"), a compound represented by formula (II-7) (hereinafter, referred to as "compound (II-7)"), a compound represented by formula (II-8) (hereinafter, referred to as "compound (II-8)") and a compound represented by formula (II-9) (hereinafter, referred to as "compound (II-9)") are encompassed in the compound (II).

[Formula 14]

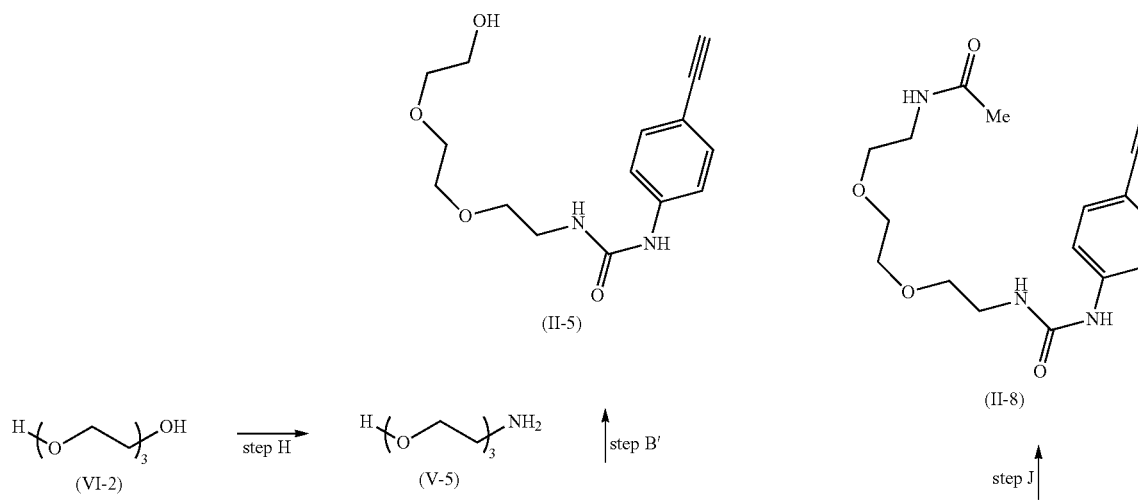

(Reaction formula 5)

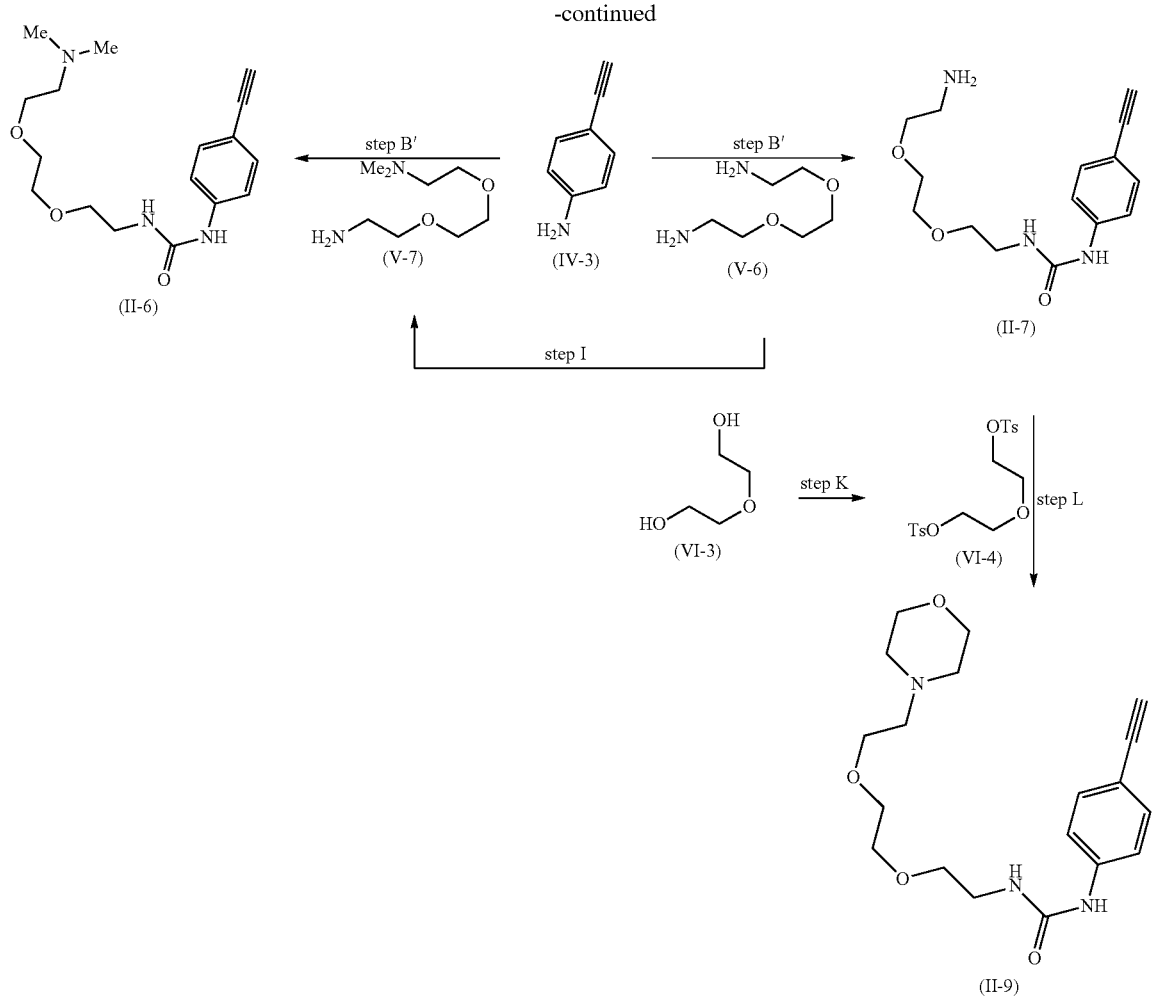

In the formula, Is represents a p-toluenesulfonyl group (tosyl group), and Me represents methyl.

In step H, a compound represented by formula (V-5) (hereinafter, referred to as "compound (V-5)") is produced from a compound represented by formula (VI-2) (hereinafter, referred to as "compound (VI-2)"). First, the compound (VI-2) is reacted with tert-butyl dimethylchlorosilane in the presence of a base in a solvent (first step). Then, a product obtained in a solvent is reacted with phthalimide, triphenylphosphine, and diethyl azodicarboxylate (second step). Subsequently, a product obtained can be reacted with hydrazine monohydrate and then with hydrochloric acid to obtain the compound (V-5) (third step).

In the first step, relative to the compound (VI-1), typically 0.8 to 1.2 equivalents, preferably 1 to 1.1 equivalents of a base, and typically 0.8 to 2 equivalents, preferably 1 to 1.2 equivalents of tert-butyl methylchlorosilane are used. The base can include, for example sodium hydride, lithium di-isopropylamide, lithium hexamethyldisilazide, n-butyl-lithium, and among them, sodium hydride is preferable. The solvent is not particularly limited, and can include, for example N,N-dimethylformamide, toluene, diethyl ether, 1,2-dimethoxyethane, tetrahydrofuran, etc., and among them, tetrahydrofuran is preferable. Although the reaction time varies depending on reagents or solvents to be used, it is typically 1 to 48 hours, preferably 15 to 24 hours. Although the reaction temperature varies depending on reagents or solvents to be used, it is typically 0 to 100° C., preferably 0 to 25° C.

In the second step, relative to the product obtained in the first step, typically 0.5 to 2 equivalents, preferably 1 to 1.6 equivalents of phthalimide, typically 1 to 2 equivalents, preferably 1 to 1.6 equivalents of triphenylphosphine, as well as typically 1 to 2 equivalents, preferably 1 to 1.2 equivalents of diethylazodicarboxylate are used. Instead of diethylazodicarboxylate, bis(2-methoxyethyl)azodicarboxylate, diisopropyl azodicarboxylate, cyanomethylene tributylphosphorane or the like may be used. The solvent is not particularly limited, and can include, for example dichloromethane, 1,4-dioxane, tetrahydrofuran, toluene, N,N-dimethylformamide etc., and among them, tetrahydrofuran is preferable. Although the reaction time varies depending on reagents or solvents to be used, it is typically 5 to 20 hours, preferably 12 to 18 hours. Although the reaction temperature varies depending on reagents or solvents to be used, it is typically 0 to 40° C., preferably 0 to 25° C.

In the third step, relative to the product obtained in the second step, typically 1 to 5 equivalents, preferably 1 to 4.4 equivalents of hydrazine monohydrate are used. The solvent is not particularly limited, and can include, for example methanol, ethanol, isopropanol, etc., and among them, ethanol is preferable. Although the reaction time varies depending on reagents or solvents to be used, it is typically 2 to 20 hours, preferably 4 to 18 hours.

Although the reaction temperature varies depending on reagents or solvents to be used, it is typically 25 to 120° C., preferably 80 to 100° C. Then, 5 to 10 equivalents, preferably 8 to 10 equivalents of concentrated hydrochloric acid are added. Although the reaction time varies depending on reagents or solvents to be used, it is typically 2 to 20 hours, preferably 2 to 4 hours. Although the reaction temperature varies depending on reagents or solvents to be used, it is typically 0 to 120° C., preferably 90 to 110° C.

In step I, a compound represented by formula (V-7) (hereinafter, referred to as "compound (V-7)") is produced from a compound represented by formula (V-6) (hereinafter, referred to as "compound (V-6)"). First, the compound (V-6) is reacted with di-tert-butyl dicarbonate in a solvent (first step). Then, a product obtained in a solvent is reacted with formaldehyde, acetic acid, and sodium triacetoxyborohydride (second step). Subsequently, a product obtained can be reacted with a trifluoroacetic acid to obtain the compound (V-7) (third step).

In the first step, relative to the compound (V-6), typically 0.4 to 0.6 equivalents, preferably 0.5 to 0.6 equivalents of di-tert-butyl dicarbonate (in 30% tetrahydrofuran solution), and typically 0.8 to 1.1 equivalents, preferably 0.9 to 1.0 equivalent of diisopropylethylamine are used. The solvent is not particularly limited, and can include, for example tetrahydrofuran, dichloromethane, chloroform, acetonitrile, 1,4-dioxane, etc., and among them, dichloromethane is preferable. Although the reaction time varies depending on reagents or solvents to be used, it is typically 2 to 10 hours, preferably 2 to 4 hours. Although the reaction temperature varies depending on reagents or solvents to be used, it is typically 0 to 40° C., preferably 0 to 25° C.

In the second step, relative to the product obtained in the first step, typically 10 to 40 equivalents, preferably 20 to 30 equivalents of formaldehyde (37% solution in water), typically 10 to 40 equivalents, preferably 20 to 30 equivalents of acetic acid, as well as typically 1.5 to 5 equivalents, preferably 1.5 to 2 equivalents of sodium triacetoxyborohydride are used. The solvent is not particularly limited, and can include, for example methanol, ethanol, isopropanol, etc., and among them, methanol is preferable. Although the reaction time varies depending on reagents or solvents to be used, it is typically 2 to 10 hours, preferably 2 to 3 hours. Although the reaction temperature varies depending on reagents or solvents to be used, it is typically 0 to 40° C., preferably 0 to 25° C.

In the third step, relative to the product obtained in the second step, typically 5 to 20 equivalents, preferably 5 to 17 equivalents of trifluoroacetic acid are used. The solvent is not particularly limited, and can include, for example tetrahydrofuran, dichloromethane, chloroform, acetonitrile, 1,4-dioxane, etc., and among them, dichloromethane is preferable. Although the reaction time varies depending on reagents or solvents to be used, it is typically 30 minutes to 2 hours, preferably 30 minutes to 1 hour. Although the reaction temperature varies depending on reagents or solvents to be used, it is typically 0 to 40° C., preferably 0 to 25° C.

In step J, the compound (II-7) is reacted with acetic anhydride to produce the compound (II-8) in a conventional solvent. Relative to the compound (II-7), typically 1 to 5 equivalents, preferably 1.5 to 3 equivalents of acetic anhydride, and typically 0.1 to 0.5 equivalents, preferably 0.1 to 0.3 equivalents of 4-dimethylaminopyridine are used. The solvent is not particularly limited, and can include, for example tetrahydrofuran, dichloromethane, chloroform, acetonitrile, 1,4-dioxane, etc., and among them, acetonitrile is preferable. Although the reaction time varies depending on reagents or solvents to be used, it is typically 6 to 10 hours, preferably 6 to 8 hours. Although the reaction temperature varies depending on reagents or solvents to be used, it is typically 0 to 40° C., preferably 0 to 25° C.

In step K, a compound represented by formula (VI-3) (hereinafter, referred to as "compound (VI-3)") is reacted with p-toluenesulfonyl chloride to produce a compound represented by formula (VI-4) (hereinafter, referred to as "compound (VI-4)") in a conventional solvent in the presence of a base. Relative to the compound (VI-3), typically 2 to 3 equivalents, preferably 2 to 2.2 equivalents of p-toluenesulfonyl chloride are used. Relative to the compound (VI-3), typically 2 to 8 equivalents, preferably 5 to 8 equivalents of a base are used. The base can include, for example sodium hydroxide, potassium hydroxide, cesium carbonate, potassium carbonate, and among them, sodium hydroxide or potassium hydroxide is preferable. The solvent is not particularly limited, and can include, for example dichloromethane, chloroform, tetrahydrofuran, 1,4-dioxane, 1,2-dimethoxyethane, etc., and among them, dichloromethane is preferable. Although the reaction time varies depending on reagents or solvents to be used, it is typically 1 to 24 hours, preferably 3 to 10 hours. Although the reaction temperature varies depending on reagents or solvents to be used, it is typically 0 to 40° C., preferably 0 to 25° C.

In step L, the compound (II-7) is reacted with the compound (VI-4) to produce the compound (II-9) in a conventional solution in the presence of a base. Relative to the compound (II-7), typically 1 to 3 equivalents, preferably 1.5 to 2.0 equivalents of the compound (VI-4) are used. The base can include, for example sodium hydroxide, potassium hydroxide, cesium carbonate, potassium carbonate, and among them, sodium carbonate or potassium carbonate is preferable. The solvent is not particularly limited, and can include, for example acetonitrile, dichloromethane, chloroform, tetrahydrofuran, 1,4-dioxane, 1,2-dimethoxyethane, etc., and among them, acetonitrile is preferable. Although the reaction time varies depending on reagents or solvents to be used, it is typically 10 to 24 hours, preferably 10 to 18 hours. Although the reaction temperature varies depending on reagents or solvents to be used, it is typically 25 to 120° C., preferably 80 to 100° C.

In step B', the compound (II-5), (II-6), or (II-7) can be produced by using the compound (V-5), (V-6), or (V-7) instead of the compound (V-2) in the same way as step B.

The produced compound (I) of the present invention can be isolated or purified as an educt, or as its salt caused by salt formation treatment according to a conventional method. The isolation or purification method is not particularly limited and can be carried out, for example by arbitrarily selecting, a conventional method such as crystallization, recrystallization, distillation, separation and chromatography or their combination. A solvate of the compound (I) of the present invention can be obtained according to a method known per se.

EXAMPLES

Hereinafter, the present invention will be more specifically explained by citing Reference Examples, Examples, Formulation Examples and Test Examples, but the present invention is not limited thereto.

In Reference Examples, Examples and Test Examples, temperatures in all cases were designated in Celsius (° C.)

unless otherwise specified. All of amounts and percentages are based on the weights unless otherwise specified. Reagents were purchased from reagent suppliers such as Sigma-Aldrich Corporation, Tokyo Chemical Industry Co., Ltd., or Nacalai Tesque Inc., and used without purification unless otherwise stated.

Operations in Reference Examples and Examples were generally conducted in an anhydrous solvent under an argon atmosphere. The reactions were analyzed by TLC (Thin Layer Chromatography), judged by consumption of a starting material, and terminated. For TLC, silica gel 60F254 (Merck) was used, an appropriate solvent was used for development, and it was displayed at an appropriate position. Flash column chromatography was carried out using silica gel SiliaFlash (registered trademark) F60 (230 to 600 meshes, Silicycle Inc.).

For the analytical values of the compounds which will be described in Reference Examples and Examples, melting points were measured using MP-500 type V (non correction) produced by Yanaco Co. $^1$H-NMR spectra were recorded by Bruker instrument operating at 400 MHz. The NMR spectra were obtained as a $CDCl_3$ solution by arbitrarily using chloroform as a reference standard (7.26 ppm) or using tetramethylsilane (0.00 ppm) internally. Other NMR solvents were also used as needed. When peak multiplicities are reported, the following abbreviations are used: s (singlet), d (doublet), t (triplet), q (quartet), m (multiplet), br (broad), dd (doublet of doublets), dt (doublet of triplets), td (triplet of doublets). When coupling constants (J values) are explained, they are reported in hertz (Hz).

Reference Example 1

Production of
5-[(trimethylsilyl)ethynyl]pyridine-3-amine

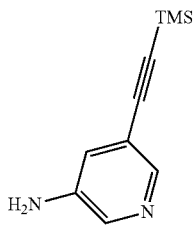

[Formula 15]

Triethylamine (20 mL) and trimethylsilylacetylene (3.32 mL, 24 mmol) were added to a solution of 3-amino-5-bromopyridine (3.46 g, 20 mmol), $PdCl_2(PPh_3)_2$ (561.5 mg, 0.80 mmol) and CuI (76.2 mg, 0.40 mmol) in tetrahydrofuran (5 mL) at room temperature, stirred for 5 minutes, and then stirred under heat reflux for 21 hours. After filtration of the resulting solution, the solvent was distilled away under a reduced pressure. The residue was purified by silica gel column chromatography (hexane/ethyl acetate (v/v)=50/50→0/100) to obtain the title compound (2.36 g, 62%) as a brown powder.

$^1$H NMR (400 MHz, $CDCl_3$) δ 8.10 (1H, d, J=1.6 Hz), 8.01 (1H, d, J=2.8 Hz), 7.03 (1H, dd, J=2.8, 1.6 Hz), 3.68 (2H, br s), 0.25 (9H, s).

Reference Example 2

Production of
5-[(trimethylsilyl)ethynyl]pyridine-2-amine

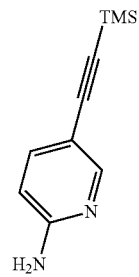

[Formula 16]

2-Amino-5-bromopyridine (5.2 g, 30 mmol), $PdCl_2(PPh_3)_2$ (842.3 mg, 1.2 mmol), CuI (114.3 mg, 0.60 mmol), tetrahydrofuran (15 mL), triethylamine (30 mL) and trimethylsilylacetylene (4.98 mL, 36 mmol) were used as raw materials, and treated in the same way as Reference Example 1 to obtain the title compound (5.17 g, 91%) as a yellow powder.

$^1$H NMR (400 MHz, $CDCl_3$) δ 8.21 (1H, d, J=2.0 Hz), 7.49 (1H, dd, J=8.4, 2.0 Hz), 6.41 (1H, br d, J=8.4 Hz), 4.56 (2H, br s), 0.24 (9H, s).

Reference Example 3

Production of
6-[(trimethylsilyl)ethynyl]pyridine-3-amine

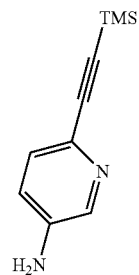

[Formula 17]

3-Amino-6-bromopyridine (6.50 g, 37.6 mmol), $PdCl_2(PPh_3)_2$ (1.05 g, 1.5 mmol), CuI (142.8 mg, 0.75 mmol), tetrahydrofuran (19 mL), triethylamine (38 mL) and trimethylsilylacetylene (6.24 mL, 45.1 mmol) were used as raw materials, and treated in the same way as Reference Example 1 to obtain the title compound (6.28 g, 88%) as a brown powder.

$^1$H NMR (400 MHz, $CDCl_3$) δ 8.03 (1H, d, J=2.8 Hz), 7.25 (1H, d, J=8.4 Hz), 6.88 (1H, dd, J=8.4, 2.8 Hz), 3.84 (2H, br s), 0.24 (9H, s).

Reference Example 4

Production of 5-ethynylpyridine-3-amine

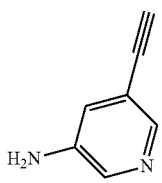

[Formula 18]

A solution of sodium hydroxide (1.00 g) in methanol (10 mL) was added to a solution of 5-[(trimethylsilyl)ethynyl]pyridine-3-amine (1.90 g, 10 mmol) in tetrahydrofuran (10 mL) at room temperature, and stirred for 4 hours. The resulting solution was diluted with water and extraction was carried with ethyl acetate. The organic layer was washed with saturated saline, dried with anhydrous sodium sulfate, and then the solvent was distilled away under a reduced pressure. The residue was purified by silica gel column chromatography (hexane/ethyl acetate (v/v)=50/50→25/75) to obtain the title compound (800.1 mg, 68%) as a brown powder.

$^1$H NMR (400 MHz, CDCl$_3$) δ 8.13 (1H, d, J=1.6 Hz), 8.05 (1H, d, J=2.4 Hz), 7.05 (1H, dd, J=2.4, 1.6 Hz), 3.72 (2H, br s), 3.14 (1H, s).

Reference Example 5

Production of 5-ethynylpyridine-2-amine

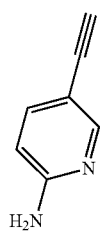

[Formula 19]

5-[(Trimethylsilyl)ethynyl]pyridine-2-amine (4.40 g, 23.2 mmol), tetrahydrofuran (23 mL), sodium hydroxide (2.30 g), and methanol (23 mL) were used as raw materials and treated in the same way as Reference Example 4 to obtain the title compound (2.71 g, 99%) as a brown powder.

$^1$H NMR (400 MHz, CDCl$_3$) δ 8.23 (1H, d, J=2.0 Hz), 7.51 (1H, dd, J=8.8, 2.0 Hz), 6.43 (1H, br d, J=8.8 Hz), 4.59 (2H, br s), 3.05 (1H, s).

Reference Example 6

Production of 6-ethynylpyridine-3-amine

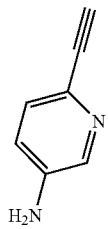

[Formula 20]

6-[(Trimethylsilyl)ethynyl]pyridine-3-amine (6.28 g, 33.0 mmol), tetrahydrofuran (33 mL), sodium hydroxide (3.30 g), and methanol (33 mL) were used as raw materials and treated in the same way as Reference Example 4 to obtain the title compound (3.60 g, 92%) as a black powder.

$^1$H NMR (400 MHz, CDCl$_3$) δ 8.05 (1H, d, J=2.8 Hz), 7.27 (1H, d, J=8.4 Hz), 6.89 (1H, dd, J=8.4, 2.8 Hz), 3.89 (2H, br s), 3.01 (1H, s).

Reference Example 7

Production of 2-(2-methoxyethoxy)ethane-1-amine

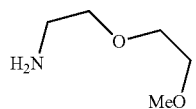

[Formula 21]

Diethylene glycol monomethyl ether (3.9 mL, 33.3 mmol) and diethyl azodicarboxylate (2.2 mol/L toluene solution) (15.5 mL, 34.1 mmol) were added to a solution of phthalimide (4.90 g, 34.2 mmol) and triphenylphosphine (9.00 g, 34.2 mmol) in tetrahydrofuran (180 mL) at room temperature, and stirred overnight. To the resulting solution, ethanol (60 mL) was further added, stirred at room temperature for 30 minutes, and then the solvent was distilled away under a reduced pressure. Ethyl acetate (50 mL) and hexane (50 mL) were added to the residue, and insolubles were filtered off. After the filtrate was concentrated under a reduced pressure, ethanol (120 mL) and hydrazine monohydrate (2.4 mL, 68.6 mmol) were added, and stirred under heat reflux overnight. After this solution was cooled to room temperature, concentrated hydrochloric acid (15 mL) was added, and stirred under heat reflux for 1 hour. After this solution was cooled to room temperature, insolubles were filtered off, and the filtrate was concentrated under a reduced pressure. Water was added to the residue, which was washed with diethyl ether. The aqueous layer was adjusted to pH=13 with a 3N sodium hydroxide aqueous solution, and extraction was carried out with dichloromethane. The organic layer was dried with anhydrous sodium sulfate, the solvent was distilled away under a reduced pressure to obtain the title compound (1.74 g, 44%) as a pale yellow oily matter.

$^1$H NMR (400 MHz, CDCl$_3$) δ 3.64-3.61 (2H, m), 3.57-3.55 (2H, m), 3.51 (2H, t, J=5.2 Hz), 3.39 (3H, s), 2.89-2.87 (2H, m).

Reference Example 8

Production of 2-[2-(2-methoxyethoxy)ethoxy]ethane-1-amine

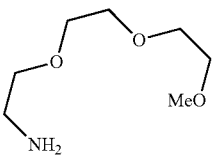

[Formula 22]

Phthalimide (5.59 g, 38 mmol), triphenylphosphine (10.3 g, 39.2 mmol), triethylene glycol monomethyl ether (6 mL, 38.4 mmol), diethyl azodicarboxylate (2.2 mol/L toluene solution) (18.2 mL, 40 mmol), tetrahydrofuran (150 mL), ethanol (220 mL) and hydrazine monohydrate (3 mL, 84.5 mmol) were used as raw materials and treated in the same way as Reference Example 7 to obtain the title compound (4.48 g, 72%) as a yellow oily matter.

$^1$H NMR (400 MHz, CDCl$_3$) δ 3.67-3.64 (6H, m), 3.57-3.55 (2H, m), 3.51 (2H, t, J=5.2 Hz), 3.38 (3H, s), 2.87 (2H, br t, J=5.2 Hz).

Reference Example 9

Production of 2,5,8,11-tetraoxatridecane-13-amine

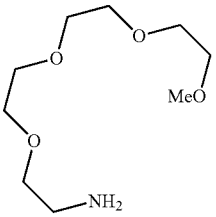

[Formula 23]

Phthalimide (2.28 g, 15.5 mmol), triphenylphosphine (4.06 g, 15.5 mmol), tetraethylene glycol monomethyl ether (3 mL, 15 mmol), diethyl azodicarboxylate (2.2 mol/L toluene solution) (7.2 mL, 15.9 mmol), tetrahydrofuran (60 mL), ethanol (50 mL) and hydrazine monohydrate (1.2 mL, 33 mmol) were used as raw materials and treated in the same way as Reference Example 7 to obtain the title compound (2.94 g, 95%) as a yellow oily matter.

$^1$H NMR (400 MHz, CDCl$_3$) δ 3.67-3.62 (10H, m), 3.56-3.54 (2H, m), 3.51-3.49 (2H, m), 3.37 (3H, s), 2.88-2.83 (2H, m).

Reference Example 10

Production of 2,5,8,11,14-pentaoxahexadecane-16-amine

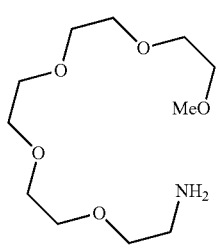

[Formula 24]

Phthalimide (1.34 g, 9.4 mmol), triphenylphosphine (2.47 g, 9.4 mmol), pentaethyleneglycol monomethyl ether (2 mL, 8.6 mmol), diethyl azodicarboxylate (2.2 mol/L toluene solution) (4.3 mL, 9.4 mmol), tetrahydrofuran (50 mL), ethanol (100 mL) and hydrazine monohydrate (660 μL, 18.8 mmol) were used as raw materials and treated in the same way as Reference Example 7 to obtain the title compound (1.34 g, 62%) as a pale yellow oily matter.

$^1$H NMR (400 MHz, CDCl$_3$) δ 3.66-3.64 (14H, m), 3.56-3.54 (2H, m), 3.51 (2H, d, J=5.2 Hz), 3.38 (3H, s), 2.86 (2H, t, J=5.2 Hz).

Reference Example 11

Production of 1-(3-ethynylphenyl)-3-(2-methoxyethyl)urea

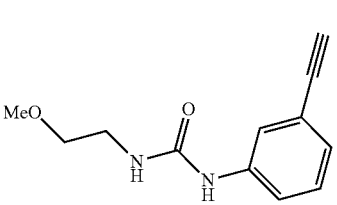

[Formula 25]

3-Ethynylaniline (585.8 mg, 5.0 mmol) and pyridine (0.44 mL, 5.5 mmol) were added to a solution of 4-nitrophenyl chloroformate (1.00 g, 5.0 mmol) in dichloromethane (50 mL), and stirred at room temperature overnight. To the resulting solution, 2-methoxyethylamine (0.94 mL, 11 mmol) was further added, stirred at room temperature for 5 hours, and then the solvent was distilled away under a reduced pressure. The residue was purified by silica gel column chromatography (hexane/ethyl acetate (v/v)=50/50→0/100) to obtain the title compound (1.05 g, 96%) as a white powder.

$^1$H NMR (400 MHz, CDCl$_3$) δ 7.42 (1H, br s), 7.37 (1H, br d, J=7.6 Hz), 7.23 (1H, t, J=7.6 Hz), 7.17 (1H, br d, J=7.6 Hz), 7.03 (1H, br s), 5.31 (1H, br, s), 3.52 (2H, br t, J=4.8 Hz), 3.46-3.42 (2H, m), 3.38 (3H, s), 3.04 (1H, s).

Reference Example 12

Production of 1-(3-ethynylphenyl)-3-[2-(2-methoxyethoxy)ethyl]urea

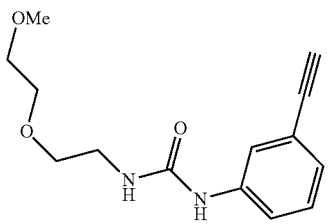

[Formula 26]

4-Nitrophenyl chloroformate (907.0 mg, 4.5 mmol), dichloromethane (45 mL), 3-ethynylaniline (527.1 mg, 4.5 mmol), pyridine (0.58 mL, 7.2 mmol) and 2-(2-methoxyethoxy)ethane-1-amine (1.43 g, 12 mmol) were used as raw materials and treated in the same way as Reference Example 11 to obtain the title compound (620.0 mg, 53%) as a brown oily matter.

$^1$H NMR (400 MHz, CDCl$_3$) δ 7.45-7.44 (1H, m), 7.42 (1H, br d, J=7.6 Hz), 7.23 (1H, t, J=7.6 Hz), 7.15 (1H, br d, J=7.6, 1.2 Hz), 6.98 (1H, br s), 5.31 (1H, br s), 3.67-3.65 (2H, m), 3.62 (2H, br t, J=4.8 Hz), 3.58-3.56 (2H, m), 3.47-3.43 (2H, m), 3.38 (3H, s), 3.04 (1H, s).

Reference Example 13

Production of 1-(3-ethynylphenyl)-3-{2-[2-(2-methoxyethoxy)ethoxy]ethyl}urea

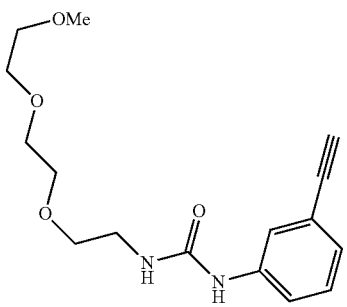

[Formula 27]

4-Nitrophenyl chloroformate (907.0 mg, 4.5 mmol), dichloromethane (45 mL), 3-ethynylaniline (527.1 mg, 4.5 mmol), pyridine (0.58 mL, 7.2 mmol) and 2-[2-(2-methoxyethoxy)ethoxy]ethane-1-amine (1.96 g, 12 mmol) were used as raw materials and treated in the same way as Reference Example 11 to obtain the title compound (819.5 mg, 59%) as a brown oily matter.

$^1$H NMR (400 MHz, CDCl$_3$) δ 7.58 (1H, br s), 7.51 (1H, br d, J=7.6 Hz), 7.48 (1H, t, J=1.2 Hz), 7.21 (1H, t, J=7.6 Hz), 7.10 (1H, br dt, J=7.6, 1.2 Hz), 5.82 (1H, br s), 3.70-3.67 (6H, m), 3.64-3.61 (4H, m), 3.47-3.43 (5H, m), 3.02 (1H, s).

Reference Example 14

Production of 1-(3-ethynylphenyl)-3-(2,5,8,11-tetraoxatridecane-13-yl)urea

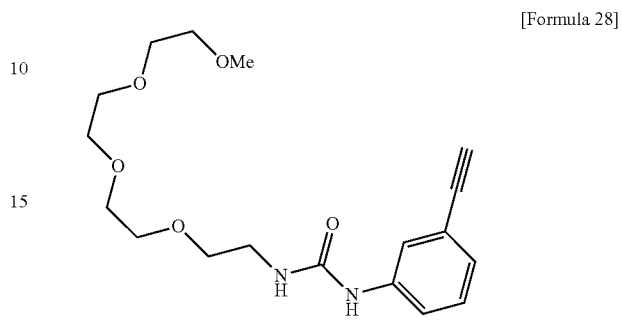

[Formula 28]

4-Nitrophenyl chloroformate (516.0 mg, 2.6 mmol), dichloromethane (25 mL), 3-ethynylaniline (288 μL, 2.6 mmol), pyridine (228 μL, 2.8 mmol) and 2,5,8,11-tetraoxatridecane-13-amine (884.5 mg, 4.3 mmol) were used as raw materials and treated in the same way as Reference Example 11 to obtain the title compound (393.0 mg, 44%) as a pale yellow oily matter.

$^1$H NMR (400 MHz, CDCl$_3$) δ 7.73 (1H, br s), 7.54-7.52 (2H, m), 7.19 (1H, br t, J=7.1 Hz), 7.09 (1H, br d, J=7.1 Hz), 5.95 (1H, br s), 3.74-3.72 (4H, m), 3.68-3.65 (4H, m), 3.62-3.58 (6H, m), 3.45-3.41 (2H, m), 3.32 (3H, s), 3.01 (1H, s).

Reference Example 15

Production of 1-(3-ethynylphenyl)-3-(2,5,8,11,14-pentaoxahexadecane-16-yl)urea

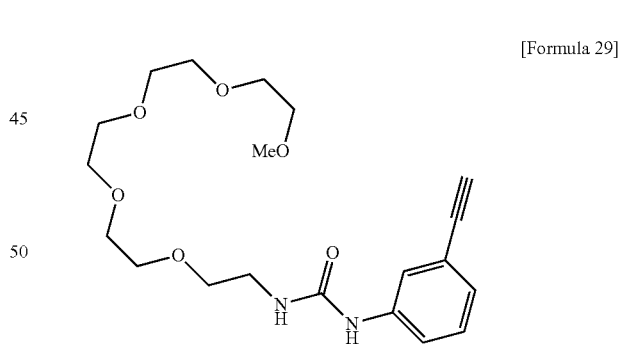

[Formula 29]

4-Nitrophenyl chloroformate (516.0 mg, 2.6 mmol), dichloromethane (25 mL), 3-ethynylaniline (288 μL, 2.6 mmol), pyridine (228 μL, 2.8 mmol) and 2,5,8,11,14-pentaoxahexadecane-16-amine (1.00 g, 4.3 mmol) were used as raw materials and treated in the same way as Reference Example 11 to obtain the title compound (965 mg, 96%) as a pale yellow oily matter.

$^1$H NMR (400 MHz, CDCl$_3$) δ 7.80 (1H, br s), 7.55 (1H, s), 7.54 (1H, d, J=7.7 Hz), 7.19 (1H, br t, J=7.7 Hz), 7.08 (1H, br d, J=7.7 Hz), 6.05 (1H, br s), 3.75-3.72 (4H, m), 3.70-3.64 (6H, m), 3.62-3.59 (6H, m), 3.48-3.43 (4H, m), 3.28 (3H, s), 3.01 (1H, s).

Reference Example 16

Production of 1-(5-ethynylpyridine-3-yl)-3-{2-[2-(2-methoxyethoxy)ethoxy]ethyl}urea

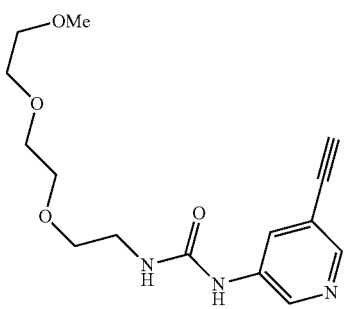

[Formula 30]

5-Ethynylpyridine-3-amine (236.3 mg, 2.0 mmol) was added to a solution of 4-nitrophenyl chloroformate (403.1 mg, 2.0 mmol) in tetrahydrofuran (20 mL), stirred at room temperature for 1 hour, and then the solvent was distilled away under a reduced pressure. To a solution of the resulting crude product in 1,4-dioxane (20 mL), 2-[2-(2-methoxyethoxy)ethoxy]ethane-1-amine (359.1 mg, 2.2 mmol) and triethylamine (0.62 mL, 4.4 mmol) were added, stirred under heat reflux overnight, and then the solvent was distilled away under a reduced pressure. The residue was purified by silica gel column chromatography (dichloromethane/methanol (v/v)=91/9) to obtain the title compound (447.7 mg, 73%) as a brown oily matter.

$^1$H NMR (400 MHz, CDCl$_3$) δ 8.40 (1H, d, J=2.8 Hz), 8.30 (1H, d, J=2.0 Hz), 8.22 (1H, br dd, J=2.8, 2.0 Hz), 7.96 (1H, br s), 6.01 (1H, br s), 3.72-3.62 (10H, m), 3.46-3.43 (5H, m), 3.15 (1H, s).

Reference Example 17

Production of 1-(5-ethynylpyridine-3-yl)-3-(2,5,8,11,14-pentaoxahexadecane-16-yl)urea

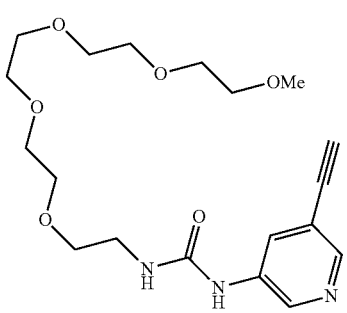

[Formula 31]

4-Nitrophenyl chloroformate (201.6 mg, 1.0 mmol), tetrahydrofuran (10 mL), 5-ethynylpyridine-3-amine (118.2 mg, 1.0 mmol), 1,4-dioxane (10 mL), 2,5,8,11,14-pentaoxahexadecane-16-amine (276.5 mg, 1.1 mmol) and triethylamine (0.31 mL, 2.2 mmol) were used as raw materials and treated in the same way as Reference Example 16 to obtain the title compound (249.5 mg, 63%) as a brown oily matter.

$^1$H NMR (400 MHz, CDCl$_3$) δ 8.48 (1H, d, J=2.8 Hz), 8.29 (1H, d, J=1.6 Hz), 8.23 (1H, br dd, J=2.8, 1.6 Hz), 8.06 (1H, br s), 6.02 (1H, br s), 3.78-3.75 (4H, m), 3.72-3.59 (12H, m), 3.45-3.43 (4H, m), 3.27 (s, 3H), 3.14 (1H, s).

Reference Example 18

Production of 1-(4-ethynylphenyl)-3-(2-methoxyethyl)urea

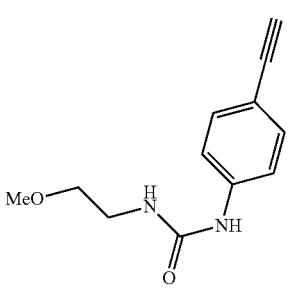

[Formula 32]

Pyridine (0.42 mL, 5.2 mmol) and 4-ethynylaniline (502.3 mg, 4.3 mmol) were added to a solution of 4-nitrophenyl chloroformate (873.4 mg, 4.3 mmol) in dichloromethane (30 mL) and stirred at room temperature for 45 minutes. To this solution, a solution of 2-methoxyethylamine (664.4 mg, 8.8 mmol) in dichloromethane (5 mL) was added, stirred at room temperature for 1 hour, then diluted with dichloromethane, and washed with a 10% citric acid aqueous solution and saturated saline. The organic layer was dried with anhydrous magnesium sulfate, and the solvent was distilled away under a reduced pressure. The residue was purified by silica gel column chromatography (hexane/ethyl acetate (v/v)=1/2) to obtain the title compound (759.7 mg, 81%) as a pale orange solid.

$^1$H NMR (400 MHz, CDCl$_3$) δ 7.41 (2H, d, J=8.4 Hz), 7.28 (2H, d, J=8.4 Hz), 7.14 (1H, br s), 5.31 (1H, br s), 3.52 (2H, br t, J=4.8 Hz), 3.46-3.42 (2H, m), 3.39 (3H, s), 3.02 (1H, s).

Reference Example 19

Production of 1-(4-ethynylphenyl)-3-[2-(2-methoxyethoxy)ethyl]urea

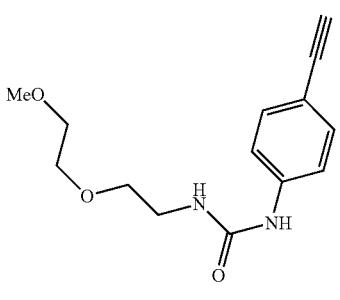

[Formula 33]

4-Nitrophenyl chloroformate (622.2 mg, 3.1 mmol), dichloromethane (12 mL), pyridine (0.25 mL, 3.1 mmol), 4-ethynylaniline (300 mg, 2.6 mmol) and 2-(2-methoxyethoxy)ethane-1-amine (613.2 mg, 5.1 mmol) were used as raw materials and treated in the same way as Reference Example 18 to obtain the title compound (485.3 mg, 72%) as an orange oily matter.

$^1$H NMR (400 MHz, CDCl$_3$) δ 7.38-7.31 (5H, m), 5.54 (1H, br s), 3.65-3.64 (2H, m), 3.61 (2H, t, J=5.2 Hz), 3.57-3.54 (2H, m), 3.46-3.42 (2H, m), 3.37 (3H, s), 3.00 (1H, s).

Reference Example 20

Production of 1-(4-ethynylphenyl)-3-{2-[2-(2-methoxyethoxy)ethoxy]ethyl}urea

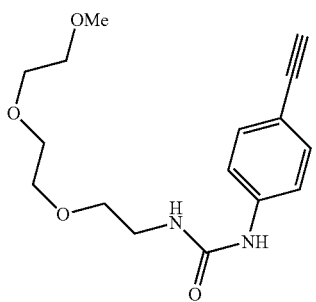

[Formula 34]

4-Nitrophenyl chloroformate (3.43 g, 17.0 mmol), dichloromethane (130 mL), pyridine (1.54 mL, 19.0 mmol), 4-ethynylaniline (2.0 g, 17.0 mmol) and 2-[2-(2-methoxyethoxy)ethoxy]ethane-1-amine (3.60 g, 22.1 mmol) were used as raw materials and treated in the same way as Reference Example 18 to obtain the title compound (3.87 g, 74%) as an orange oily matter.

$^1$H NMR (400 MHz, CDCl$_3$) δ 7.73 (1H, br s), 7.38 (4H, m), 5.87 (1H, br s), 3.69 (6H, br m), 3.63-3.61 (4H, m), 3.46-3.45 (5H, m), 2.99 (1H, s).

Reference Example 21

Production of 1-(4-ethynylphenyl)-3-(2,5,8,11-tetraoxatridecane-13-yl)urea

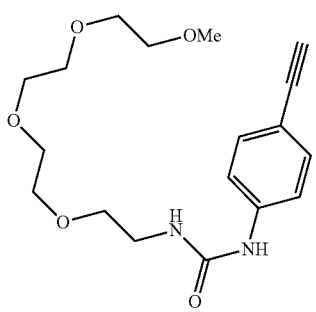

[Formula 35]

4-Nitrophenyl chloroformate (253.9 mg, 1.3 mmol), dichloromethane (4 mL), pyridine (0.12 mL, 1.5 mmol), 4-ethynylaniline (120.5 mg, 1.0 mmol) and 2,5,8,11-tetraoxatridecane-13-amine (417.9 mg, 2.0 mmol) were used as raw materials and treated in the same way as Reference Example 18 to obtain the title compound (348.5 mg, 97%) as an orange oily matter.

$^1$H NMR (400 MHz, CDCl$_3$) δ 7.82 (1H, br s), 7.43 (2H, br d, J=8.8 Hz), 7.37 (2H, br d, J=8.8 Hz), 5.90 (1H, br t, J=5.2 Hz), 3.77-3.74 (4H, m), 3.68-3.65 (4H, m), 3.63-3.58 (6H, m), 3.45-3.41 (2H, m), 3.30 (3H, s), 2.99 (1H, s).

Reference Example 22

Production of 1-(4-ethynylphenyl)-3-(2,5,8,11,14-pentaoxahexadecane-16-yl)urea

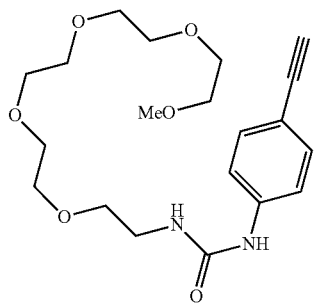

[Formula 36]

4-Nitrophenyl chloroformate (216.0 mg, 1.1 mmol), dichloromethane (4 mL), pyridine (0.10 mL, 1.2 mmol), 4-ethynylaniline (103.5 mg, 0.88 mmol) and 2,5,8,11,14-pentaoxahexadecane-16-amine (431.5 mg, 1.7 mmol) were used as raw materials and treated in the same way as Reference Example 18 to obtain the title compound (335.2 mg, 96%) as an orange oily matter.

$^1$H NMR (400 MHz, CDCl$_3$) δ 7.93 (1H, br s), 7.44 (2H, br d, J=8.8 Hz), 7.38 (2H, br d, J=8.8 Hz), 5.99 (1H, br t, J=4.4 Hz), 3.78-3.73 (4H, m), 3.71-3.68 (2H, m), 3.67-3.64 (4H, m), 3.63-3.58 (6H, m), 3.45-3.41 (4H, m), 3.27 (3H, s), 2.98 (1H, s).

Reference Example 23

Production of 1-(5-ethynylpyridine-2-yl)-3-{2-[2-(2-methoxyethoxy)ethoxy]ethyl}urea

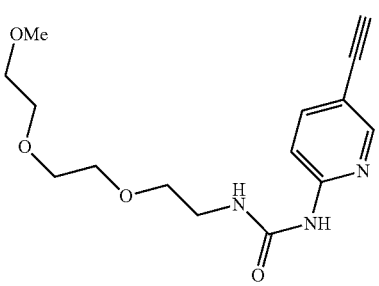

[Formula 37]

4-Nitrophenyl chloroformate (341.0 mg, 1.7 mmol), dichloromethane (18 mL), 5-ethynylpyridine-2-amine (200 mg, 1.7 mmol), 1,4-dioxane (15 mL), triethylamine (1.2 mL, 8.5 mmol) and 2-[2-(2-methoxyethoxy)ethoxy]ethane-1-amine (408.0 mg, 2.5 mmol) were used as raw materials and treated in the same way as Reference Example 16 to obtain the title compound (168.0 mg, 32%) as a pale yellow oily matter.

$^1$H NMR (400 MHz, CDCl$_3$) δ 8.31 (1H, d, J=1.8 Hz), 7.71 (1H, dd, J=8.8, 1.8 Hz), 7.11 (1H, d, J=8.8 Hz), 3.65-3.59 (8H, m), 3.52-3.47 (4H, m), 3.34 (4H, br s).

Reference Example 24

Production of 1-(5-ethynylpyridine-2-yl)-3-(2,5,8,11-tetraoxatridecane-13-yl)urea

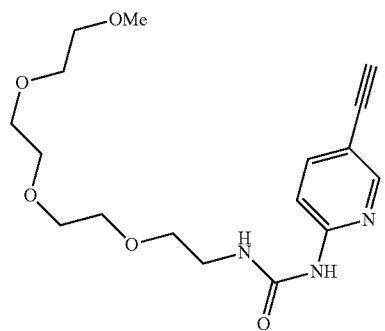

[Formula 38]

4-Nitrophenyl chloroformate (341.0 mg, 1.7 mmol), dichloromethane (18 mL), 5-ethynylpyridine-2-amine (200 mg, 1.7 mmol), 1,4-dioxane (15 mL), triethylamine (520 μL, 1.9 mmol) and 2,5,8,11-tetraoxatridecane-13-amine (526.0 mg, 2.5 mmol) were used as raw materials and treated in the same way as Reference Example 16 to obtain the title compound (284.0 mg, 48%) as a pale yellow oily matter.
$^1$H NMR (400 MHz, CDCl$_3$) δ 8.31 (1H, d, J=1.8 Hz), 7.72 (1H, dd, J=8.8, 1.8 Hz), 7.12 (1H, d, J=8.8 Hz), 3.67-3.59 (12H, m), 3.52-3.46 (4H, m), 3.35 (1H, s), 3.34 (3H, s).

Reference Example 25

Production of 1-(5-ethynylpyridine-2-yl)-3-(2,5,8,11,14-pentaoxahexadecane-16-yl)urea

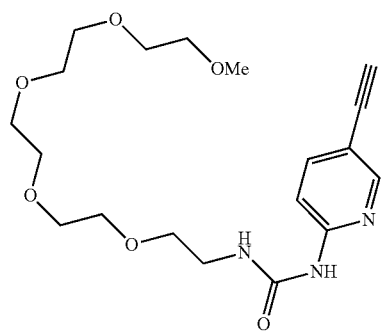

[Formula 39]

4-Nitrophenyl chloroformate (341.0 mg, 1.7 mmol), dichloromethane (20 mL), 5-ethynylpyridine-2-amine (200 mg, 1.7 mmol), 1,4-dioxane (15 mL), triethylamine (260 μL, 1.9 mmol) and 2,5,8,11,14-pentaoxahexadecane-16-amine (850.0 mg, 3.4 mmol) were used as raw materials and treated in the same way as Reference Example 16 to obtain the title compound (553.0 mg, 83%) as a yellow oily matter.

$^1$H NMR (400 MHz, CDCl$_3$) δ 8.31 (1H, d, J=1.8 Hz), 7.72 (1H, dd, J=8.8, 1.8 Hz), 7.12 (1H, d, J=8.8 Hz), 3.66-3.59 (16H, m), 3.53-3.46 (4H, m), 3.35 (1H, s), 3.34 (3H, s).

Reference Example 26

Production of 1-(6-ethynylpyridine-3-yl)-3-{2-[2-(2-methoxyethoxy)ethoxy]ethyl}urea

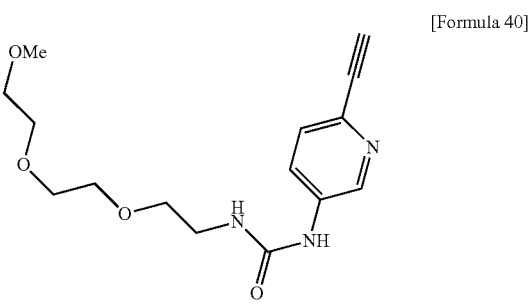 [SMILES: C#Cc1ccc(NC(=O)NCCOCCOCCOC)cn1]

[Formula 40]

4-Nitrophenyl chloroformate (341.0 mg, 1.7 mmol), tetrahydrofuran (18 mL), 6-ethynylpyridine-3-amine (200 mg, 1.7 mmol), 1,4-dioxane (15 mL), triethylamine (260 μL, 1.9 mmol) and 2-[2-(2-methoxyethoxy) ethoxy]ethane-1-amine (552.0 mg, 3.4 mmol) were used as raw materials and treated in the same way as Reference Example 16 to obtain the title compound (319.7 mg, 62%) as a pale orange oily matter.
$^1$H NMR (400 MHz, CDCl$_3$) δ 8.37 (1H, d, J=2.4 Hz), 8.33 (1H, s), 8.12 (1H, dd, J=8.6, 2.4 Hz), 7.40 (1H, d, J=8.6 Hz), 6.17 (1H, br s), 3.67-3.58 (10H, m), 3.44-3.43 (2H, m), 3.40 (3H, s), 3.13 (1H, s).

Reference Example 27

Production of 1-(6-ethynylpyridine-3-yl)-3-(2,5,8,11-tetraoxatridecane-13-yl)urea

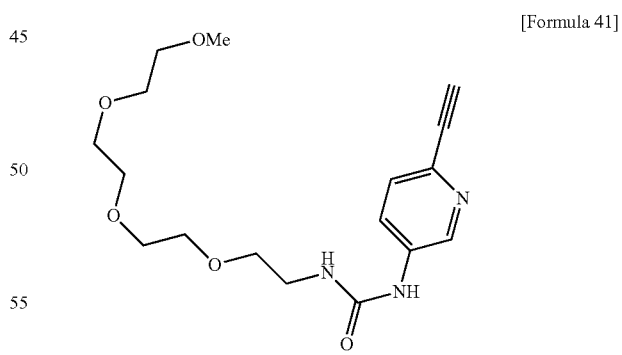

[Formula 41]

4-Nitrophenyl chloroformate (273.0 mg, 1.4 mmol), tetrahydrofuran (15 mL), 6-ethynylpyridine-3-amine (160 mg, 1.4 mmol), 1,4-dioxane (15 mL), triethylamine (260 μL, 1.9 mmol) and 2,5,8,11-tetraoxatridecane-13-amine (560.0 mg, 2.7 mmol) were used as raw materials and treated in the same way as Reference Example 16 to obtain the title compound (417.3 mg, 88%) as a brown oily matter.
$^1$H NMR (400 MHz, CDCl$_3$) δ 8.39 (1H, d, J=2.4 Hz), 8.17 (1H, dd, J=8.7, 2.4 Hz), 8.11 (1H, s), 7.39 (1H, d, J=8.7

Hz), 6.13 (1H, br s), 3.76-3.74 (4H, m), 3.68-3.66 (6H, m), 3.62-3.59 (4H, m), 3.46-3.42 (2H, m), 3.31 (3H, s), 3.05 (1H, s).

Reference Example 28

Production of 1-(6-ethynylpyridine-3-yl)-3-(2,5,8,11,14-pentaoxahexadecane-16-yl)urea

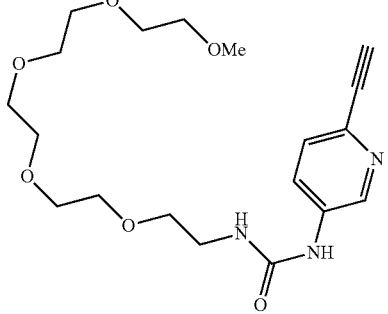

[Formula 42]

4-Nitrophenyl chloroformate (341.0 mg, 1.7 mmol), tetrahydrofuran (18 mL), 6-ethynylpyridine-3-amine (200.0 mg, 1.7 mmol), 1,4-dioxane (15 mL), triethylamine (260 μL, 1.9 mmol) and 2,5,8,11,14-pentaoxahexadecane-16-amine (850.0 mg, 3.4 mmol) were used as raw materials and treated in the same way as Reference Example 16 to obtain the title compound (585.0 mg, 88%) as a yellow oily matter.

$^1$H NMR (400 MHz, CDCl$_3$) δ 8.43 (1H, d, J=2.4 Hz), 8.17-8.16 (2H, m), 7.40 (1H, d, J=8.4 Hz), 6.13 (1H, br s), 3.77-3.58 (18H, m), 3.45-3.44 (2H, m), 3.26 (3H, s), 3.06 (1H, s).

Reference Example 29

Production of 2-methoxyethyl (3-ethynylphenyl)carbamate

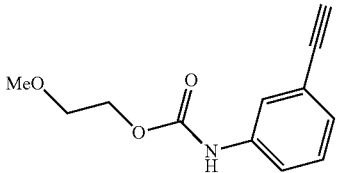

[Formula 43]

Di(N-succinimidyl)carbonate (1.34 g, 5.3 mmol) and triethylamine (1.39 mL, 10 mmol) were added to a solution of 2-methoxyethanol (0.39 mL, 5.0 mmol) in ethyl acetate (15 mL) while cooling in ice, stirred for 30 minutes, and then stirred at room temperature overnight. To the resulting solution, 3-ethynylaniline (0.62 mL, 5.5 mmol) was further added, and stirred under heat reflux for 5 hours. The solvent was distilled away under reduced pressure, and the residue was purified by silica gel column chromatography (hexane/ethyl acetate (v/v)=80/20→50/50) to obtain the title compound (771.0 mg, 70%) as a colorless oily matter.

$^1$H NMR (400 MHz, CDCl3) δ 7.50 (1H, br s), 7.39 (1H, br d, J=7.6 Hz), 7.25 (1H, br t, J=7.6 Hz), 7.19 (1H, br d, J=7.6 Hz), 6.74 (1H, br s), 4.33 (2H, br t, J=4.4 Hz), 3.64 (2H, br t, J=4.4 Hz), 3.42 (3H, s), 3.06 (1H, s).

Reference Example 30

Production of 2-(2-methoxyethoxy)ethyl (3-ethynylphenyl)carbamate

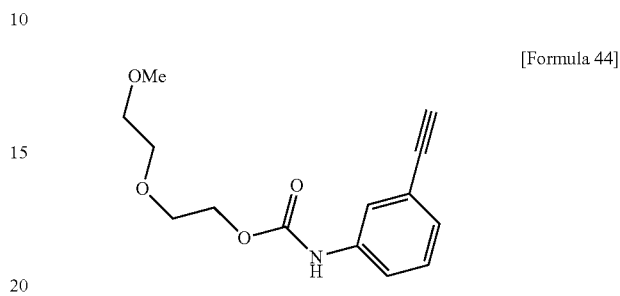

[Formula 44]

Diethyleneglycol monomethyl ether (0.59 mL, 5.0 mmol), ethyl acetate (15 mL), di(N-succinimidyl)carbonate (1.34 g, 5.3 mmol), triethylamine (1.39 mL, 10 mmol) and 3-ethynylaniline (0.62 mL, 5.5 mmol) were used as raw materials and treated in the same way as Reference Example 29 to obtain the title compound (757.5 mg, 57%) as a colorless oily matter.

$^1$H NMR (400 MHz, CDCl$_3$) δ 7.50 (1H, br s), 7.39 (1H, br d, J=7.6 Hz), 7.25 (1H, t, J=7.6 HZ), 7.18 (1H, br dt, J=7.6, 1.2 Hz), 6.75 (1H, br s), 4.34 (2H, br t, J=4.4 Hz), 3.75 (2H, br t, J=4.4 Hz), 3.68-3.66 (2H, m), 3.58-3.56 (2H, m), 3.39 (3H, s), 3.05 (1H, s).

Reference Example 31

Production of 2-[2-(2-methoxyethoxy)ethoxy]ethyl (3-ethynylphenyl)carbamate

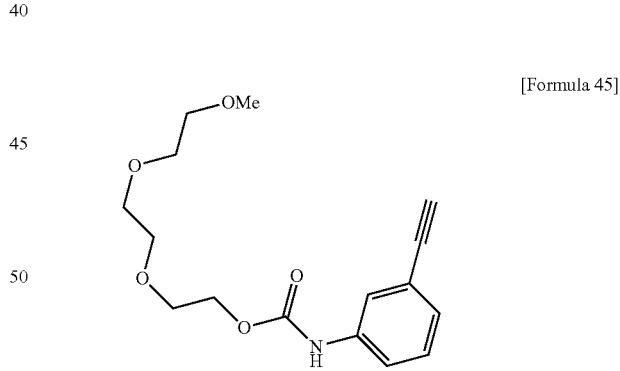

[Formula 45]

Triethyleneglycol monomethyl ether (0.78 mL, 5.0 mmol), ethyl acetate (15 mL), di(N-succinimidyl)carbonate (1.34 g, 5.3 mmol), triethylamine (1.39 mL, 10 mmol) and 3-ethynylaniline (0.62 mL, 5.5 mmol) were used as raw materials and treated in the same way as Reference Example 29 to obtain the title compound (1.00 g, 68%) as a pale yellow oily matter.

$^1$H NMR (400 MHz, CDCl$_3$) δ 7.51 (1H, br s), 7.40 (1H, br d, J=7.6 Hz), 7.25 (1H, t, J=7.6 Hz), 7.18 (1H, br dt, J=7.6, 1.2 Hz), 6.91 (1H, br s), 4.33 (2H, br t, J=4.4 Hz), 3.75 (2H, br t, J=4.4 Hz), 3.70-3.65 (6H, m), 3.57-3.55 (2H, m), 3.38 (3H, s), 3.05 (1H, s).

Reference Example 32

Production of 2-methoxyethyl (4-ethynylphenyl)carbamate

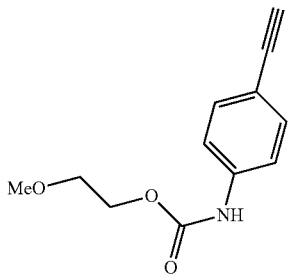

[Formula 46]

2-Methoxyethanol (385.9 mg, 5.1 mmol), ethyl acetate (4 mL), di(N-succinimidyl)carbonate (1.35 g, 5.3 mmol), triethylamine (2.0 mL, 14 mmol) and 4-ethynylaniline (704.2 mg, 6.0 mmol) were used as raw materials and treated in the same way as Reference Example 29 to obtain the title compound (913.7 mg, 82%) as an orange oily matter.

$^1$H NMR (400 MHz, CDCl$_3$) δ 7.43 (2H, br d, J=8.4 Hz), 7.34 (2H, br d, J=8.4 Hz), 6.79 (1H, br s), 4.34-4.32 (2H, br t, J=4.4 Hz), 3.65-3.62 (2H, br t, J=4.4 Hz), 3.41 (3H, s), 3.02 (1H, s).

Reference Example 33

Production of 2-(2-methoxyethoxy)ethyl (4-ethynylphenyl)carbamate

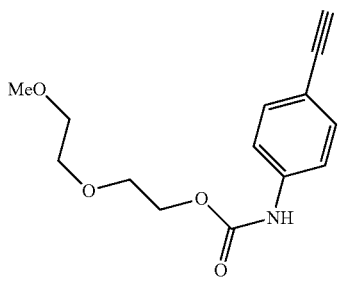

[Formula 47]

Diethyleneglycol monomethyl ether (600.6 mg, 5.0 mmol), ethyl acetate (4 mL), di(N-succinimidyl)carbonate (1.35 g, 5.3 mmol), triethylamine (2 mL, 14 mmol) and 4-ethynylaniline (709.7 mg, 6.1 mmol) were used as raw materials and treated in the same way as Reference Example 29 to obtain the title compound (1.06 g, 80%) as an orange oily matter.

$^1$H NMR (400 MHz, CDCl$_3$) δ 7.44 (2H, br d, J=8.8 Hz), 7.34 (2H, d, J=8.8 Hz), 6.77 (1H, br s), 4.34 (2H, br t, J=4.8 Hz), 3.74 (2H, br t, J=4.8 Hz), 3.68-3.66 (2H, m), 3.58-3.56 (2H, m), 3.39 (3H, s), 3.02 (1H, s).

Reference Example 34

Production of 2-[2-(2-methoxyethoxy)ethoxy]ethyl (4-ethynylphenyl)carbamate

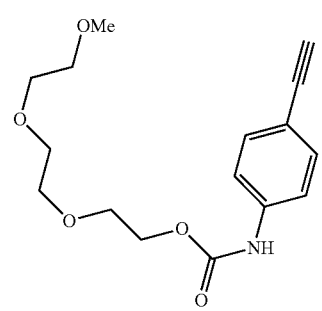

[Formula 48]

Triethyleneglycol monomethyl ether (824.3 mg, 5.0 mmol), ethyl acetate (4 mL), di(N-succinimidyl)carbonate (1.37 g, 5.3 mmol), triethylamine (2.0 mL, 14 mmol) and 4-ethynylaniline (744.2 mg, 6.4 mmol) were used as raw materials and treated in the same way as Reference Example 29 to obtain the title compound (1.21 g, 79%) as a yellow oily matter.

$^1$H NMR (400 MHz, CDCl$_3$) δ 7.43 (2H, br d, J=8.8 Hz), 7.35 (2H, br d, J=8.8 Hz), 6.93 (1H, br s), 4.33 (2H, br t, J=4.8 Hz), 3.74 (2H, br t, J=4.8 Hz), 3.71-3.69 (6H, m), 3.57-3.55 (2H, m), 3.38 (3H, s), 3.02 (1H, s).

Reference Example 35

Production of 2,5,8,11-tetraoxatridecane-13-yl (4-ethynylphenyl)carbamate

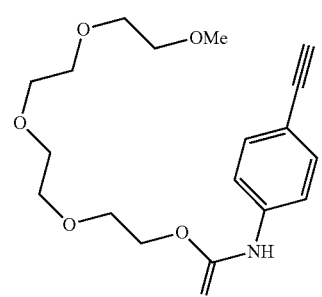

[Formula 49]

Tetraethyleneglycol monomethyl ether (1.53 g, 7.4 mmol), ethyl acetate (10 mL), di(N-succinimidyl)carbonate (2.11 g, 8.2 mmol), triethylamine (3.0 mL, 22 mmol) and 4-ethynylaniline (1.12 g, 9.5 mmol) were used as raw materials and treated in the same way as Reference Example 29 to obtain the title compound (1.54 g, 60%) as an orange oily matter.

$^1$H NMR (400 MHz, CDCl$_3$) δ 7.43 (2H, br d, J=8.8 Hzs), 7.36 (2H, br d, J=8.8 Hz), 7.10 (1H, br s), 4.33 (2H, br t, J=4.8 Hz), 3.74 (2H, br t, J=4.8 Hz), 3.68-3.64 (10H, m), 3.57-3.54 (2H, m), 3.37 (3H, s), 3.02 (1H, s).

Reference Example 36

Production of 2,5,8,11,14-pentaoxahexadecane-16-yl (4-ethynylphenyl)carbamate

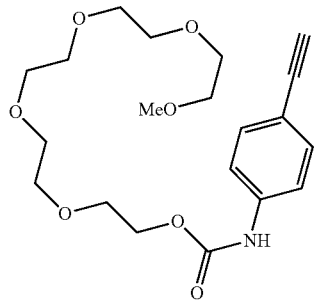

[Formula 50]

Pentaethyleneglycol monomethyl ether (1.54 g, 6.1 mmol), ethyl acetate (10 mL), di(N-succinimidyl)carbonate (1.77 g, 6.9 mmol), triethylamine (2.6 mL, 19 mmol), 4-ethynylaniline (962.2 mg, 8.2 mmol) and 4-dimethylaminopyridine (78.5 mg, 0.64 mmol) were used as raw materials and treated in the same way as Reference Example 29 to obtain the title compound (1.20 g, 50%) as an orange oily matter.

$^1$H NMR (400 MHz, CDCl$_3$) δ 7.43 (2H, br d, J=8.8 Hz), 7.37 (2H, br d, J=8.8 Hz), 7.14 (1H, br s), 4.33 (2H, br t, J=4.8 Hz), 3.74 (2H, br t, J=4.8 Hz), 3.67-3.63 (14H, m), 3.55-3.52 (2H, m), 3.36 (3H, s), 3.02 (1H, s).

Reference Example 37

Production of 3,6,9,12-tetraoxatridecanoic acid

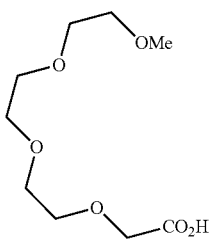

[Formula 51]

Tetraethyleneglycol monomethyl ether (3.04 g, 19 mmol) was added to a solution of 60% sodium hydride (1.37 g, 34 mmol) in tetrahydrofuran (10 mL) while cooling in ice and stirred for 20 minutes. To this solution, tert-butyl bromoacetate (4.31 g, 22 mmol) was dripped while cooling in ice, and stirred at room temperature for 13 hours. To this solution, lithium hydroxide (1.73 g, 72 mmol) and water (15 mL) were further added and stirred under heat reflux for 4 hours. The solution was diluted with water and washed with diethyl ether. The aqueous layer was adjusted to pH=1 with 6N hydrochloric acid, and extraction was carried out with dichloromethane/methanol (v/v)=10/1. The organic layers were combined, then dried with anhydrous sodium sulfate, and the solvent was distilled away under a reduced pressure to obtain the title compound (2.13 g, 52%) as an orange oily matter.

$^1$H NMR (400 MHz, CDCl$_3$) δ 4.16 (2H, s), 3.78-3.75 (2H, m), 3.70-3.63 (8H, m), 3.59-3.57 (2H, m), 3.39 (3H, s).

Reference Example 38

Production of 3,6,9,12,15-pentaoxahexadecanoic acid

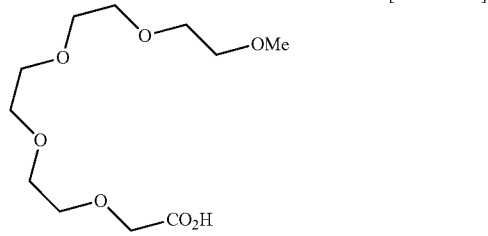

[Formula 52]

60% Sodium hydride (2.20 g, 54.6 mmol), tetrahydrofuran (29 mL), tetraethyleneglycol monomethyl ether (3.80 g, 18.2 mmol), tert-butyl bromoacetate (2.93 mL, 20.0 mmol), lithium hydroxide (1.30 g, 54.6 mmol) and water (3.6 mL) were used as raw materials and treated in the same way as Reference Example 37 to obtain the title compound (2.79 g, 58%) as a brown oily matter.

$^1$H NMR (400 MHz, CDCl$_3$) δ 4.16 (2H, s), 3.77-3.56 (16H, m), 3.39 (3H, s).

Reference Example 39

Production of 3,6,9,12,15,18-hexaoxanonadecanoic acid

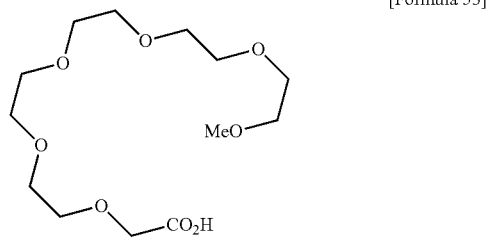

[Formula 53]

60% Sodium hydride (600 mg, 15 mmol), tetrahydrofuran (8 mL), pentaethyleneglycol monomethyl ether (1.26 g, 5.0 mmol), tert-butyl bromoacetate (0.81 mL, 5.5 mmol), lithium hydroxide (359.3 mg, 15 mmol) and water (1 mL) were used as raw materials and treated in the same way as Reference Example 37 to obtain the title compound (1.38 g, 89%) as a colourless oily matter.

$^1$H NMR (400 MHz, CDCl$_3$) δ 4.17 (2H, s), 3.75-3.55 (20H, m), 3.38 (3H, s).

Reference Example 40

Production of N-(3-ethynylphenyl)-2,5,8,11,14,17-hexaoxanonadecane-19-amide

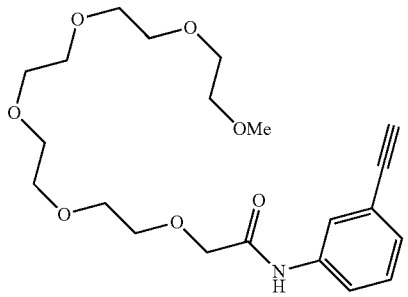

[Formula 54]

1-Ethyl-3-[3-(dimethylamino)propyl]carbodiimide hydrochloride (238.5 mg, 1.2 mmol), 4-dimethylaminopyridine (161.1 mg, 1.3 mmol) and 3-ethynylaniline (116.3 mg, 0.99 mmol) were added to a solution of 3,6,9,12,15,18-hexaoxanonadecanoic acid (214.4 mg, 0.70 mmol) in dichloromethane (3 mL) and stirred at room temperature for 3 hours. The reaction solution was diluted with ethyl acetate, washed with 1N hydrochloric acid, a saturated sodium bicarbonate aqueous solution and saturated saline, and then dried with anhydrous sodium sulfate. The solvent was distilled away under a reduced pressure to obtain the title compound (218.2 mg, 77%) as an orange oily matter.

$^1$H NMR (400 MHz, CDCl$_3$) δ 8.89 (1H, s), 7.74 (1H, t, J=1.6 Hz), 7.67 (1H, dt, J=8.0, 1.6 Hz), 7.28 (1H, dt, J=8.0 Hz), 7.24 (1H, dt, J=8.0, 1.6 Hz), 4.10 (2H, s), 3.77-3.75 (2H, m), 3.72-3.71 (4H, m), 3.69-3.67 (2H, m), 3.63-3.59 (10H, m), 3.53-3.51 (2H, m), 3.36 (3H, s), 3.10 (1H, s).

Reference Example 41

Production of N-(4-ethynylphenyl)-2,5,8,11-tetraoxatridecane-13-amide

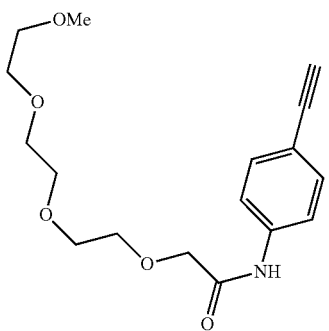

[Formula 55]

3,6,9,12-Tetraoxatridecanoic acid (488.9 mg, 2.2 mmol), dichloromethane (3 mL), 1-ethyl-3-[3-(dimethylamino)propyl]carbodiimide hydrochloride (766.8 mg, 4.0 mmol), 4-dimethylaminopyridine (366.4 mg, 6.0 mmol) and 4-ethynylaniline (234.3 mg, 2.0 mmol) were used as raw materials and treated in the same way as Reference Example 40 to obtain the title compound (257.8 mg, 40%) as a brown oily matter.

$^1$H NMR (400 MHz, CDCl$_3$) δ 8.88 (1H, br, s), 7.61 (2H, br d, J=8.4 Hz), 7.45 (2H, br d, J=8.4 Hz), 4.11 (2H, s), 3.77-3.60 (10H, m), 3.52-3.49 (2H, m), 3.34 (3H, s), 3.04 (1H, s).

Reference Example 42

Production of N-(4-ethynylphenyl)-2,5,8,11,14-pentaoxahexadecane-16-amide

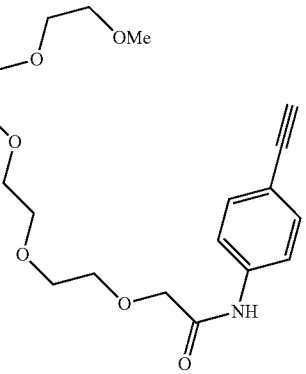

[Formula 56]

3,6,9,12,15-Pentaoxahexadecanoic acid (878.8 mg, 3.3 mmol), dichloromethane (5 mL), 1-ethyl-3-[3-(dimethylamino)propyl]carbodiimide hydrochloride (1.15 g, 6.0 mmol), 4-dimethylaminopyridine (1.47 g, 12 mmol) and 4-ethynylaniline (351.5 mg, 3.0 mmol) were used as raw materials and treated in the same way as Reference Example 40 to obtain the title compound (408.3 mg, 37%) as a brown oily matter.

$^1$H NMR (400 MHz, CDCl$_3$) δ 8.88 (1H, br, s), 7.61 (2H, br d, J=8.4 Hz), 7.45 (2H, br d, J=8.4 Hz), 4.11 (2H, s), 3.77-3.59 (14H, m), 3.52-3.50 (2H, m), 3.36 (3H, s), 3.04 (1H, s).

Reference Example 43

Production of N-(4-ethynylphenyl)-2,5,8,11,14,17-hexaoxanonadecane-19-amide

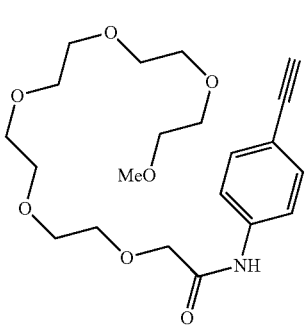

[Formula 57]

3,6,9,12,15,18-Hexaoxanonadecanoic acid (220.3 mg, 0.71 mmol), dichloromethane (3 mL), 4-ethynylaniline (109.8 mg, 0.94 mmol), 1-ethyl-3-[3-(dimethylamino)propyl]carbodiimide hydrochloride (284.4 mg, 1.5 mmol) and 4-dimethylaminopyridine (173.5 mg, 1.4 mmol) were used as raw materials and treated in the same way as Reference Example 40 to obtain the title compound (199.6 mg, 69%) as a red oily matter.

¹H NMR (400 MHz, CDCl₃) δ 9.02 (1H, br, s), 7.64 (2H, br d, J=8.4 Hz), 7.44 (2H, br d, J=8.4 Hz), 4.10 (2H, s), 3.77-3.74 (2H, m), 3.72-3.70 (4H, m), 3.68-3.66 (2H, m), 3.62-3.59 (10H, m), 3.52-3.50 (2H, m), 3.35 (3H, s), 3.11 (1H, s).

Reference Example 44

Production of N-(5-ethynylpyridine-2-yl)-2,5,8,11-tetraoxatridecane-13-amide

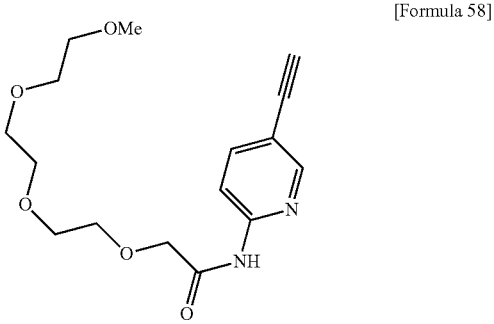 [SMILES: C#Cc1ccc(NC(=O)COCCOCCOCCOC)nc1]

[Formula 58]

1-Ethyl-3-[3-(dimethylamino)propyl]carbodiimide hydrochloride (526.1 mg, 2.7 mmol), 4-dimethylaminopyridine (664.6 mg, 5.4 mmol), dichloromethane (5 mL) and 5-ethynylpyridine-2-amine (239.6 mg, 2.0 mmol) were added to 3,6,9,12-tetraoxatridecanoic acid (320.1 mg, 1.4 mmol), and stirred at room temperature overnight. The reaction solution was diluted with ethyl acetate, washed with a 10% citric acid aqueous solution, dried with anhydrous sodium sulfate, and then the solvent was distilled away under a reduced pressure. The residue was purified by silica gel column chromatography (hexane/ethyl acetate (v/v)=1/4) to obtain the title compound (199.4 mg, 43%) as a brown oily matter.

¹H NMR (400 MHz, CDCl₃) δ 9.24 (1H, br, s), 8.42 (1H, br d, J=2.4 Hz), 8.23 (1H, d, J=8.8 Hz), 7.79 (1H, dd, J=8.8, 2.4 Hz), 4.16 (2H, s), 3.79-3.77 (2H, m), 3.74-3.72 (6H, m), 3.66-3.63 (2H, m), 3.55-3.52 (2H, m), 3.37 (3H, s), 3.16 (1H, s).

Reference Example 45

Production of N-(5-ethynylpyridine-2-yl)-2,5,8,11,14-pentaoxahexadecane-16-amide

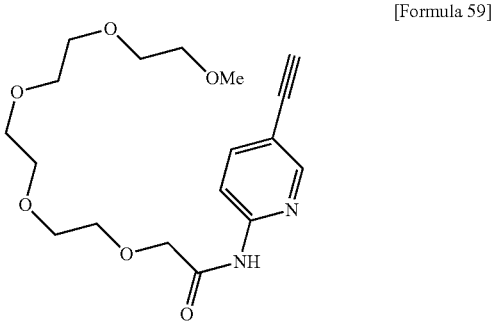 [SMILES: C#Cc1ccc(NC(=O)COCCOCCOCCOCCOC)nc1]

[Formula 59]

3,6,9,12,15-Pentaoxanhexadecanoic acid (427.8 mg, 1.6 mmol), N,N-dimethylformamide (5 mL), O-(7-azabenzotriazol-1-yl)-N,N,N',N'-tetramethyluronium hexafluorophosphate (1.24 g, 3.3 mmol), N,N-diisopropylethylamine (1.2 mL, 6.9 mmol) and 5-ethynylpyridine-2-amine (181 mg, 1.5 mmol) were used as raw materials and treated in the same way as Reference Example 44 to obtain the title compound (140.2 mg, 25%) as a red oily matter.

¹H NMR (400 MHz, CDCl₃) δ 9.28 (1H, br, s), 8.41 (1H, s), 8.21 (1H, d, J=8.4 Hz), 7.78 (1H, br d, J=8.4 Hz), 4.18 (2H, s), 3.79-3.77 (2H, m), 3.74-3.71 (6H, m), 3.66-3.63 (6H, m), 3.55-3.52 (2H, m), 3.36 (3H, s), 3.22 (1H, s).

Reference Example 46

Production of N-(5-ethynylpyridine-2-yl)-2,5,8,11,14,17-hexaoxanonadecane-19-amide

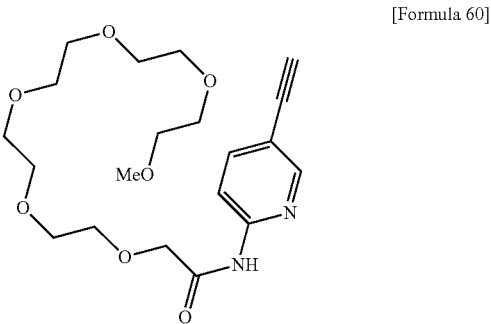 [SMILES: C#Cc1ccc(NC(=O)COCCOCCOCCOCCOCCOC)nc1]

[Formula 60]

3,6,9,12,15,18-Hexaoxanonadecanoic acid (315.0 mg, 1.0 mmol), dichloromethane (1 mL), N,N-dimethylformamide (3 mL), 1-ethyl-3-[3-(dimethylamino)propyl]carbodiimide hydrochloride (413.0 mg, 2.2 mmol), 4-dimethylaminopyridine (497.0 mg, 4.1 mmol) and 5-ethynylpyridine-2-amine (239.0 mg, 2.0 mmol) were used as raw materials and treated in the same way as Reference Example 44 to obtain the title compound (266.6 mg, 64%) as an orange solid.

¹H NMR (400 MHz, CDCl₃) δ 9.27 (1H, br, s), 8.41 (1H, br d, J=2.0 Hz), 8.23 (1H, br d, J=8.8 Hz), 7.79 (1H, dd, J=8.8, 2.0 Hz), 4.16 (2H, s), 3.78-3.63 (18H, m), 3.55-3.54 (2H, m), 3.37 (3H, s), 3.16 (1H, s).

Reference Example 47

Production of N-(6-ethynylpyridine-3-yl)-2,5,8,11-tetraoxatridecane-13-amide

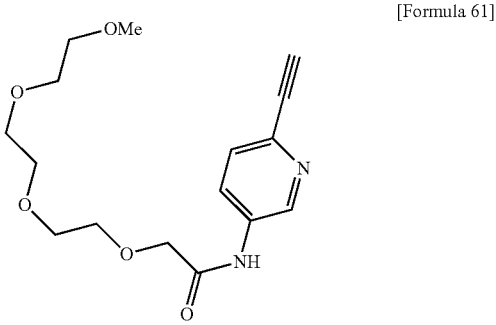 [SMILES: C#Cc1ccc(NC(=O)COCCOCCOCCOC)cn1]

[Formula 61]

3,6,9,12-Tetraoxatridecanoic acid (446.5 mg, 2.0 mmol), 1-ethyl-3-[3-(dimethylamino)propyl]carbodiimide hydrochloride (776.0 mg, 4.0 mmol), dichloromethane (10 mL), triethylamine (1.1 mL, 7.9 mmol), 6-ethynylpyridine-3-amine (255.2 mg, 2.2 mmol) and 4-dimethylaminopyridine (30.5 mg, 0.25 mmol) were used as raw materials and treated in the same way as Reference Example 44 to obtain the title compound (96.7 mg, 15%) as a brown oily matter.

$^1$H NMR (400 MHz, CDCl$_3$) δ 9.16 (1H, br, s), 8.66 (1H, br s), 8.28 (1H, dd, J=8.4, 2.4 Hz), 7.47 (1H, br d, J=8.4 Hz), 4.14 (2H, s), 3.77-3.63 (10H, m), 3.51-3.49 (2H, m), 3.32 (3H, s), 3.14 (1H, s).

Reference Example 48

Production of 2-[2-(2-methoxyethoxy)ethoxy]ethyl-4-methylbenzenesulfonate

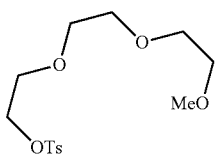

[Formula 62]

Triethylamine (1.27 mL, 9.15 mmol) and triethylene glycol monomethyl ether (525 μL, 3.05 mmol) were added to a solution of p-toluenesulfonyl chloride (872.2 mg, 4.58 mmol) in dichloromethane (3 mL), and stirred at room temperature overnight. To this solution, methanol (0.5 mL) was further added, stirred at room temperature for 1 hour, and the solvent was distilled away under a reduced pressure. Diethyl ether was added to the residue, and insolubles were filtered off and washed with diethyl ether and isopropanol. The filtrate was concentrated under a reduced pressure, water was added to the residue, and extraction was carried out with dichloromethane. The organic layers were combined, then dried with anhydrous sodium sulfate, and the solvent was distilled away under a reduced pressure to obtain the title compound (796.9 mg, 82%) as a brown oily matter.

$^1$H NMR (400 MHz, CDCl$_3$) δ 7.80 (2H, d, J=8.2 Hz), 7.34 (2H, d, J=8.2 Hz), 4.16 (2H, br t, J=4.8 Hz), 3.70-3.68 (2H, m), 3.62-3.59 (6H, m), 3.54-3.52 (2H, m), 3.37 (3H, s), 2.45 (3H, s).

Reference Example 49

Production of 2,5,8,11-tetraoxatridecane-13-yl 4-methylbenzenesulfonate

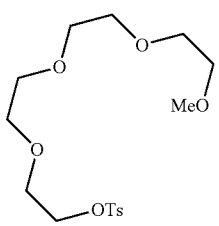

[Formula 63]

p-Toluenesulfonyl chloride (7.19 g, 37.7 mmol), dichloromethane (25 mL), triethylamine (10.5 mL, 75.3 mmol) and tetraethylene glycol monomethyl ether (5 mL, 25.1 mmol) were used as raw materials and treated in the same way as Reference Example 48 to obtain the title compound (8.24 g, 90%) as a brown oily matter.

$^1$H NMR (400 MHz, CDCl$_3$) δ 7.80 (2H, d, J=8.2 Hz), 7.34 (2H, d, J=8.2 Hz), 4.16 (2H, br t, J=5.0 Hz), 3.70-3.68 (2H, m), 3.65-3.62 (6H, m), 3.59-3.57 (4H, m), 3.55-3.53 (2H, m), 3.37 (3H, s), 2.45 (3H, s).

Reference Example 50

Production of 2,5,8,11,14-pentaoxahexadecane-16-yl 4-methylbenzenesulfonate

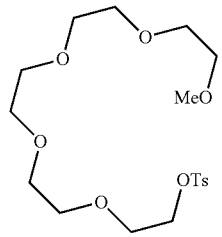

[Formula 64]

p-Toluenesulfonyl chloride (3.06 g, 16.1 mmol), dichloromethane (12 mL), triethylamine (4.5 mL, 32.1 mmol), and pentaethylene glycol monomethyl ether (2.5 mL, 10.7 mmol) were used as raw materials and treated in the same way as Reference Example 48 to obtain the title compound (3.14 g, 72%) as a brown oily matter.

$^1$H NMR (400 MHz, CDCl$_3$) δ 7.80 (2H, d, J=8.2 Hz), 7.34 (2H, d, J=8.2 Hz), 4.16 (2H, br t, J=4.4 Hz), 3.70-3.58 (16H, m), 3.55-3.54 (2H, m), 3.37 (3H, br s), 2.45 (3H, s).

Reference Example 51

Production of 3-ethynyl-N-(2-methoxyethyl)aniline

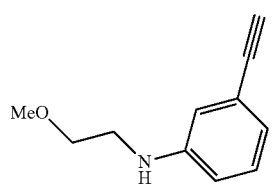

[Formula 65]

3-Ethynylaniline (288 μL, 2.6 mmol) and 1-bromo-2-methoxyethane (360 μL, 3.8 mmol) were added to a solution of cesium carbonate (1.37 g, 4.2 mmol) and potassium iodide (84.0 mg, 0.52 mmol) in N,N-dimethylformamide (8 mL), and stirred at 100° C. overnight. The solution was diluted with water, extraction was carried out with ethyl acetate. The organic layer was washed with water, dried with anhydrous sodium sulfate, and then the solvent was distilled away under a reduced pressure. The residue was purified by silica gel column chromatography (hexane→hexane/ethyl acetate (v/v)=96/4) to obtain the title compound (132.2 mg, 29%) as a brown oily matter.

¹H NMR (400 MHz, CDCl₃) δ 7.11 (1H, t, J=7.5 Hz), 6.85 (1H, br d, J=7.5 Hz), 6.74 (1H, t, J=2.2 Hz), 6.62 (1H, t, J=7.5, 2.2 Hz), 4.06 (1H, br s), 3.59 (2H, t, J=5.2 Hz), 3.38 (3H, s), 3.27 (2H, t, J=5.2 Hz), 3.00 (1H, s).

Reference Example 52

Production of 3-ethynyl-N-[2-(2-methoxyethoxy)ethyl]aniline

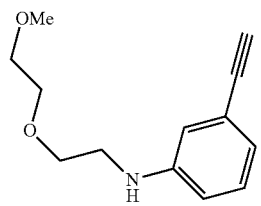

[Formula 66]

Cesium carbonate (1.37 g, 4.2 mmol), potassium iodide (84.0 mg, 0.52 mmol), N,N-dimethylformamide (8 mL), 3-ethynylaniline (288 μL, 2.6 mmol) and 1-bromo-2-(2-methoxyethoxy)ethane (517 μL, 3.8 mmol) were used as raw materials and treated in the same way as Reference Example 51 to obtain the title compound (155.0 mg, 28%) as a brown oily matter.

¹H NMR (400 MHz, CDCl₃) δ 7.10 (1H, t, J=7.6 Hz), 6.84 (1H, br d, J=7.6 Hz), 6.74 (1H, t, J=2.2 Hz), 6.62 (1H, br dd, J=7.6, 2.2 Hz), 4.16 (1H, br s), 3.70 (2H, t, J 5.2 Hz), 3.65-3.63 (2H, m), 3.57-3.54 (2H, m), 3.40 (3H, s), 3.31-3.27 (2H, m), 3.00 (1H, s).

Reference Example 53

Production of 3-ethynyl-N-{2-[2-(2-methoxyethoxy)ethoxy]ethyl}aniline

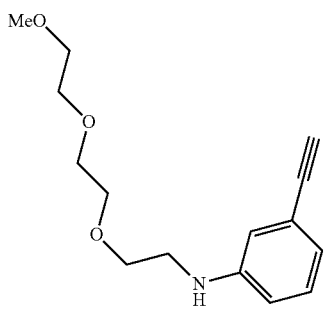

[Formula 67]

Potassium carbonate (194.0 mg, 1.4 mmol), potassium iodide (29.0 mg, 0.18 mmol) and 3-ethynylaniline (96 μL, 0.85 mmol) were added to a solution of 2-[2-(2-methoxyethoxy)ethoxy]ethyl-4-methylbenzenesulfonate (223.0 mg, 0.7 mmol) in acetonitrile (4 mL), and stirred under heat reflux overnight. Insolubles were filtered off from the resulting solution, and then the filtrate was concentrated under a reduced pressure. The residue was purified by silica gel column chromatography (hexane/ethyl acetate (v/v)=60/40→40/60) to obtain the title compound (100.2 mg, 54%) as a pale yellow oily matter.

¹H NMR (400 MHz, CDCl₃) δ 7.10 (1H, t, J=7.9 Hz), 6.84 (1H, br d, J=7.9 Hz), 6.74 (1H, t, J=2.2 Hz), 6.62 (1H, br dd, J=7.9, 2.2 Hz), 4.20 (1H, br s), 3.70 (2H, t, J=5.2 Hz), 3.67-3.64 (6H, m), 3.57-3.55 (2H, m), 3.39 (3H, s), 3.28 (2H, br m), 3.00 (1H, s).

Reference Example 54

Production of 4-ethynyl-N-[2-(2-methoxyethoxy)ethyl]aniline

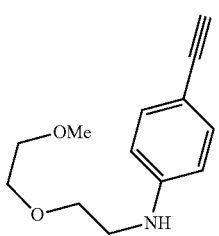

[Formula 68]

Cesium carbonate (1.37 g, 4.2 mmol), potassium iodide (84.0 mg, 0.52 mmol), N,N-dimethylformamide (8 mL), 4-ethynylaniline (300.0 mg, 2.6 mmol) and 1-bromo-2-(2-methoxyethoxy)ethane (777 μL, 5.8 mmol) were used as raw materials and treated in the same way as Reference Example 51 to obtain the title compound (100.0 mg, 18%) as a pale yellow oily matter.

¹H NMR (400 MHz, CDCl₃) δ 7.30 (2H, d, J=8.8 Hz), 6.52 (1H, br s=8.8 Hz), 4.33 (1H, br s), 3.69 (2H, t, J=5.2 Hz), 3.64-3.62 (2H, m), 3.56-3.54 (2H, m), 3.39 (3H, s), 3.30-3.29 (2H, m), 2.95 (1H, s).

Reference Example 55

Production of 4-ethynyl-N-{2-[2-(2-methoxyethoxy)ethoxy]ethyl}aniline

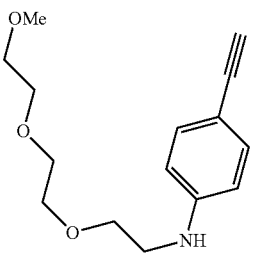

[Formula 69]

2-[2-(2-Methoxyethoxy)ethoxy]ethyl 4-methylbenzenesulfonate (669.0 mg, 2.1 mmol), acetonitrile (12 mL), potassium carbonate (582.0 mg, 4.2 mmol), potassium iodide (87.0 mg, 0.52 mmol) and 4-ethynylaniline (300.0 mg, 2.6 mmol) were used as raw materials and treated in the same way as Reference Example 53 to obtain the title compound (224.9 mg, 40%) as a brown oily matter.

¹H NMR (400 MHz, CDCl₃) δ 7.30 (2H, d, J=8.8 Hz), 6.53 (1H, br s=8.8 Hz), 4.36 (1H, br s), 3.70 (2H, t, J=5.2 Hz), 3.65-3.64 (6H, m), 3.57-3.54 (2H, m), 3.38 (3H, s), 3.32-3.28 (2H, m), 2.95 (1H, s).

Reference Example 56

Production of N-(4-ethynylphenyl)-2,5,8,11-tetraoxatridecane-13-amine

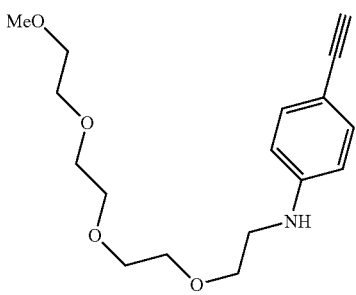

[Formula 70]

2,5,8,11-Tetraoxatridecane-13-yl 4-methylbenzensulfonate (1.00 g, 2.8 mmol), acetonitrile (20 mL), potassium carbonate (1.40 g, 10 mmol), potassium iodide (227 mg, 1.4 mmol) and 4-ethynylaniline (800.0 mg, 6.8 mmol) were used as raw materials and treated in the same way as Reference Example 53 to obtain the title compound (446.0 mg, 53%) as a yellow oily matter.
$^1$H NMR (400 MHz, CDCl$_3$) δ 7.30 (2H, d, J=8.8 Hz), 6.53 (1H, d, J=8.8 Hz), 4.36 (1H, br s), 3.70 (2H, t, J=5.2 Hz), 3.66-3.63 (10H, m), 3.55-3.53 (2H, m), 3.37 (3H, s), 3.32-3.28 (2H, m), 2.95 (1H, s).

Reference Example 57

Production of N-(4-ethynylphenyl)-2,5,8,11,14-pentaoxahexadecane-16-amine

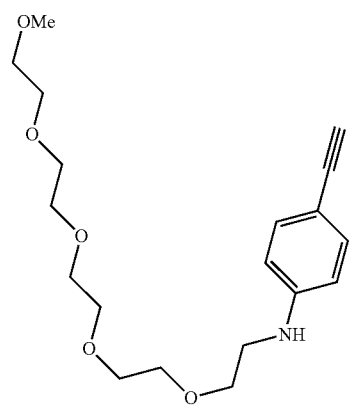

[Formula 71]

2,5,8,11,14-Pentaoxahexadecane-16-yl 4-methylbenzensulfonate (694.3 mg, 1.7 mmol), acetonitrile (12 mL), potassium carbonate (885.0 mg, 6.4 mmol), potassium iodide (141.8 mg, 0.85 mmol) and 4-ethynylaniline (500.0 mg, 4.3 mmol) were used as raw materials and treated in the same way as Reference Example 53 to obtain the title compound (104.0 mg, 17%) as a yellow oily matter.
$^1$H NMR (400 MHz, CDCl$_3$) δ 7.30 (2H, d, J=8.8 Hz), 6.53 (2H, d, J=8.8 Hz), 4.39 (1H, br s), 3.70 (2H, t, J=5.2 Hz), 3.66-3.62 (14H, m), 3.55-3.52 (2H, m), 3.37 (3H, s), 3.31-3.28 (2H, m), 2.95 (1H, s).

Reference Example 58

Production of 2,2'-dithiosalicylic dichloride

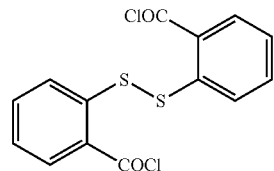

[Formula 72]

Oxalyl chloride (25 mL, 291.5 mmol) and N,N-dimethylformamide (150 μL, 1.94 mmol) were added to a solution of 2,2'-dithiosalicylic acid (25.0 g, 81.6 mmol) in dichloromethane (220 mL), and stirred at room temperature for 18 hours. The resulting solution was further stirred at 50° C. for 24 hours, and then the solvent was distilled away under a reduced pressure. The resulting solid was washed with hexane at 0° C. and dried to obtain the title compound (24.9 g, 89%) as a pale yellow solid.
$^1$H NMR (400 MHz, CDCl$_3$) δ 8.40 (2H, dd, J=8.0, 1.4 Hz), 7.77 (2H, dd, J=8.0, 1.1 Hz), 7.55 (2H, td, J=8.0, 1.4 Hz), 7.24 (2H, td, J=8.0, 1.1 Hz).

Reference Example 59

Production of 2,2'-dithiobis(N-methylbenzamide)

[Formula 73]

Methylamine (2M tetrahydrofuran solution) (80 mL, 160.2 mmol) was added to a solution of 2,2'-dithiosalicylic dichloride (12.5 g, 36.4 mmol) in tetrahydrofuran (56 mL) at 0° C. and stirred at room temperature for 16 hours. Water was added to this solution, stirred for 30 minutes, and then the solvent was distilled away under a reduced pressure. The resulting solid was washed with water and dried to obtain the title compound (11.7 g, 96%) as a pale yellow solid.
$^1$H NMR (400 MHz, CDCl$_3$) δ 7.75 (2H, br d, J=7.6 Hz), 7.47 (2H, dd, J=7.6, 1.2 Hz), 7.36 (2H, td, J=7.6, 1.2 Hz), 7.24 (2H, td, J=7.6, 1.2 Hz), 6.13 (2H, br m), 2.97 (6H, d, J=4.8 Hz).

Reference Example 60

Production of 2-mercapto-N-methylbenzamide

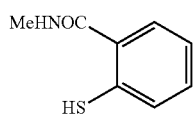

[Formula 74]

Sodium borohydride (3.05 g, 80.7 mmol) was added to a solution of 2,2'-dithiobis(N-methylbenzamide) (11.7 g, 35.1 mmol) in ethanol (110 mL) at 0° C. and stirred at room temperature for 16 hours. The solution was diluted with water, adjusted to pH=1 with 2N hydrochloric acid, and then the solvent was distilled away under a reduced pressure. Water was added to the residue, and extraction was carried out with ethyl acetate. The organic layer was dried with anhydrous magnesium sulfate, the solvent was distilled away under a reduced pressure to obtain the title compound (7.72 g, 66%) as a pale yellow solid.

$^1$H NMR (400 MHz, CDCl$_3$) δ 7.42 (1H, dd, J=7.8, 1.5 Hz), 7.32 (1H, dd, J=7.8, 1.3 Hz), 7.25 (1H, td, J=7.8, 1.5 Hz), 7.13 (1H, td, J=7.8, 1.3 Hz), 6.12 (1H, br m), 4.77 (1H, s), 2.99 (3H, d, J=4.8 Hz).

Reference Example 61

Production of 6-iodo-1H-indazole

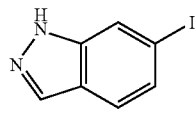

[Formula 75]

A concentrated hydrochloric acid (35 mL, 420 mmol) and an aqueous solution (30 mL) of sodium nitrite (6.64 g, 96 mmol) were added to a suspension prepared by adding water (30 mL) to 6-aminoindazole (10.4 g, 78 mmol) at 0° C. and stirred at 0° C. for 30 minutes. Subsequently, to this solution, an aqueous solution (30 mL) of potassium iodide (15.91 g, 96 mmol) was added at 0° C., stirred at room temperature for 30 minutes, to which dichloromethane (80 mL) was then added, and stirred at 40° C. for 2 hours. The reaction mixture was cooled down to 0° C., then adjusted to pH=14 with a 3N sodium hydroxide aqueous solution, and the precipitate was taken by filtration. The resulting precipitate was washed with 10% sodium thiosulfate, dissolved in tetrahydrofuran, and then silica gel was added. After stirring at room temperature for 1 hour, hexane (600 mL) was added and filtered. The residue was washed twice with a THF/hexane (1/3 (v/v)) solution, then the solvent was distilled away under a reduced pressure to obtain the title compound (15.23 g, 80%) as an orange powder.

$^1$H NMR (400 MHz, CDCl$_3$) δ 10.24 (1H, br, s), 8.04 (1H, br s), 7.92 (1H, br s), 7.51 (1H, br d, J=8.4 Hz), 7.46 (1H, dd, J=8.4, 1.2 Hz).

Reference Example 62

Production of 2-{(1H-indazol-6-yl)thio}-N-methylbenzamide

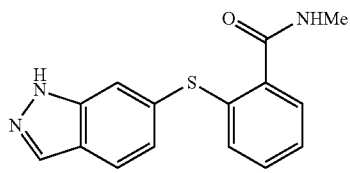

[Formula 76]

N,N-Dimethylformamide (25 mL) was added to 6-iodo-1H-indazole (5.51 g, 22 mmol), 2-mercapto-N-methylbenzamide (5.16 g, 31 mmol), Pd$_2$(dba)$_3$ (1.02 g, 1.1 mmol), 4,5-bis(diphenylphosphino)-9,9-dimethylxanthene (1.46 g, 2.5 mmol) and cesium hydroxide monohydrate (5.67 g, 33 mmol) and stirred under an argon atmosphere at 100° C. for 4.5 hours. The solvent was distilled away from the reaction solution under a reduced pressure, the residue was dissolved in ethyl acetate and washed with water and saturated saline. The organic layer was dried with anhydrous sodium sulfate, and the solvent was distilled away under a reduced pressure. The residue was purified by silica gel column chromatography (hexane/ethyl acetate (v/v)=1/3) to obtain the title compound (6.14 g, 96%) as a pale orange solid.

$^1$H NMR (400 MHz, DMSO-d$_6$) δ 13.13 (1H, br s), 8.36 (1H, br q, J=4.4 Hz), 8.10 (1H, s), 7.78 (1H, br d, J=8.4 Hz), 7.59 (1H, br s), 7.48-7.46 (1H, m), 7.29 (1H, td, J=7.6, 1.6 Hz), 7.25 (1H, td, J=7.6, 1.6 Hz), 7.08 (1H, dd, J=8.4, 1.6 Hz), 6.99-6.97 (1H, m), 2.76 (3H, d, J=4.4 Hz).

Reference Example 63

Production of 2-{(3-iodo-1H-indazol-6-yl)thio}-N-methylbenzamide

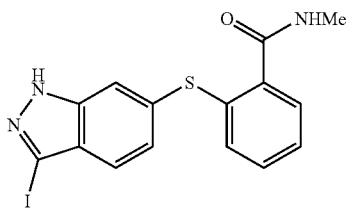

[Formula 77]

A solution of iodine (11.09 g, 46 mmol) in N,N-dimethylformamide (20 mL) was added to a solution of 2-{(1H-indazol-6-yl)thio}-N-methylbenzamide (7.32 g, 26 mmol) and potassium carbonate (7.36 g, 53 mmol) in N,N-dimethylformamide (30 mL) at 0° C. for 30 minutes, and stirred at room temperature for 3.5 hours. The solvent was distilled away from the reaction liquid under a reduced pressure, then the residue was dissolved in ethyl acetate, and washed with a 10% sodium thiosulfate aqueous solution, a saturated sodium bicarbonate aqueous solution and saturated saline. The organic layer was dried with anhydrous sodium sulfate, and the solvent was distilled away under a reduced pressure. The resulting solid was washed with a hexane/ethyl acetate (1/1 (v/v)) solution and dried to obtain the title compound (7.60 g, 72%) as a pale yellow solid.

$^1$H NMR (400 MHz, DMSO-d$_6$) δ 13.55 (1H, br s), 8.37 (1H, br q, J=4.4 Hz), 7.56 (1H, br s), 7.49-7.47 (1H, m), 7.44 (1H, br d, J=8.8 Hz), 7.31 (1H, td, J=7.6, 2.0 Hz), 7.28 (1H, td, J=7.6, 2.0 Hz), 7.14 (1H, dd, J=8.8, 1.6 Hz), 7.04-7.02 (1H, m), 2.76 (3H, d, J=4.4 Hz).

Reference Example 64

Production of triethylene glycol mono-tert-butyldimethylsilyl ether

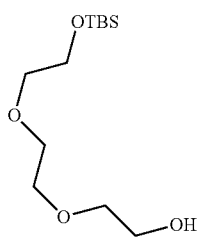

[Formula 78]

Triethylene glycol (2.2 mL, 16.5 mmol) was added to a solution of 60% sodium hydride (713 mg, 17.8 mmol) in tetrahydrofuran (88 mL) at 0° C. and stilled at room temperature for 40 minutes. To this solution, tert-butyldimethylchlorosilane (2.74 g, 18.2 mmol) was added, stirred at room temperature for 23 hours, then water was added, and extraction was carried out with dichloromethane. The organic layer was dried with anhydrous sodium sulfate, then the solvent was distilled away under a reduced pressure to obtain the title compound (4.19 g, quant.) as a pale yellow oily matter.

$^1$H NMR (400 MHz, CDCl$_3$) δ 3.79-3.72 (4H, m), 3.67-3.54 (8H, m), 0.90 (9H, s), 0.07 (6H, s).

Reference Example 65

Production of 2-(2,2,3,3-tetramethyl-4,7,10-trioxa-3-siladodecan-12-yl)isoindoline-1,3-dione

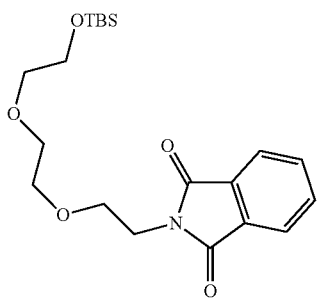

[Formula 79]

Triethyleneglycol mono-tert-butyldimethylsilyl ether (1.3 g, 4.92 mmol) and diethylazodicarboxylate (2.2 mol/L, toluene solution) (2.4 mL, 5.3 mmol) were added to a solution of phthalimide (1.15 g, 7.82 mmol) and triphenylphosphine (2.06 g, 7.85 mmol) in tetrahydrofuran (50 mL) at room temperature, and stirred overnight. Further ethanol (20 mL) was added, stirred at room temperature for 30 minutes, and then the solvent was distilled away under a reduced pressure. To the residue, ethyl acetate (12.5 mL) and hexane (12.5 mL) were added, and insolubles were filtered off. The filtrate was concentrated under a reduced pressure, and then the residue was purified by silica gel column chromatography (hexane/ethyl acetate (v/v)=5/95→0/100) to obtain the title compound (822 mg, 42%) as a colorless oily matter.

$^1$H NMR (400 MHz, CDCl$_3$) δ 7.84 (2H, dd, J=5.2, 3.2 Hz), 7.71 (2H, dd, J=5.2, 3.2 Hz), 3.90 (2H, t, J=6.0 Hz), 3.74 (2H, t, J=6.0 Hz), 3.70 (2H, t, J=5.6 Hz), 3.65-3.59 (4H, m), 3.50 (2H, t, J=5.6 Hz), 0.87 (s, 9H), 0.04 (s, 6H).

Reference Example 66

Production of 2-[2-(2-aminoethoxy)ethoxy]ethanol

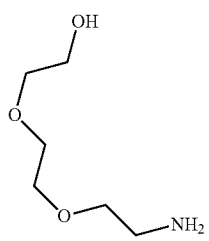

[Formula 80]

Hydrazine monohydrate (322.6 μL, 9.2 mmol) was added to a solution of 2-(2,2,3,3-tetramethyl-4,7,10-trioxa-3-siladodecan-12-yl)isoindoline-1,3-dione (822 mg, 2.09 mmol) in ethanol (120 mL), and stirred under heat reflux overnight. After cooling to room temperature, concentrated hydrochloric acid (2 mL) was added and stirred under heat reflux for 2 hours. This solution was cooled to room temperature, then the insolubles were filtered off, and the filtrate was concentrated under a reduced pressure. Water was added to the residue, which was washed with ethyl acetate. The aqueous layer was adjusted to pH=9 with a 3N sodium hydroxide aqueous solution and washed with dichloromethane/methanol (v/v)=10/1. The solvent in the aqueous layer was distilled away under a reduced pressure, and then dichloromethane was added to the residue. The insolubles were filtered off, and then the solvent was distilled away under a reduced pressure to obtain the title compound (239.1 mg, 77%) as a pale yellow oily matter.

$^1$H NMR (400 MHz, CDCl$_3$) δ 3.73 (2H, t, J=4.4 Hz), 3.69-3.64 (6H, m), 3.59 (2H, t, J=4.4 Hz), 3.03 (2H, br t, J=4.4 Hz).

Reference Example 67

Production of 1-(4-ethynylphenyl)-3-{2-[2-(2-hydroxyethoxy)ethoxy]ethyl}urea

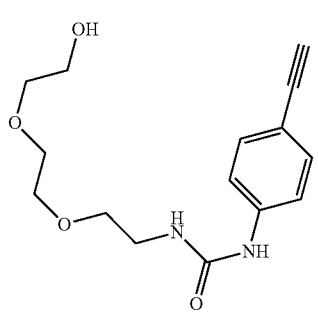

[Formula 81]

4-Ethynylaniline (170.4 mg, 1.5 mmol) was added to a solution of 4-nitrophenyl chloroformate (289.3 mg, 1.4 mmol) in tetrahydrofuran (6.8 mL), stirred at room temperature for 3 hours, and then the solvent was distilled away under a reduced pressure. To a solution of the resulting crude product in dichloromethane (4 mL), a solution of 2-[2-(2-aminoethoxy)ethoxy]ethanol (239 mg, 1.6 mmol) in dichloromethane (4 mL) and triethylamine (303 µL, 2.2 mmol) were added, stirred at room temperature overnight, and then the solvent was distilled away under a reduced pressure. The residue was purified by silica gel column chromatography (ethyl acetate/methanol (v/v)=100/0→90/10) to obtain the title compound (325.4 mg, 77%) as a pale yellow oily matter.

$^1$H NMR (400 MHz, CDCl$_3$) δ 8.30 (1H, br s), 7.32 (4H, m), 6.22 (1H, br t, J=4.4 Hz), 4.37 (1H, br s), 3.72 (2H, br t, J=4.4 Hz), 3.55-3.53 (6H, m), 3.49 (2H, t, J=4.4 Hz), 3.36-3.34 (2H, m), 3.05 (1H, s).

Reference Example 68

Production of 1-{2-[2-(2-aminoethoxy)ethoxy]ethyl}-3-(4-ethynylphenyl)urea

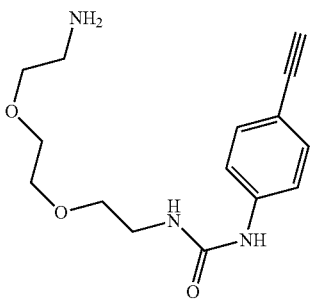

[Formula 82]

4-Ethynylaniline (200 mg, 1.7 mmol) was added to a solution of 4-nitrophenyl chloroformate (341 mg, 1.7 mmol) in tetrahydrofuran (7.5 mL), stirred at room temperature for 3 hours, and then the solvent was distilled away under a reduced pressure. A solution of the resulting crude product in dichloromethane (10 mL) was dripped into a solution of 2,2'-[1,2-ethane-diyl-bis(oxy)]bis-ethaneamine (496 µL, 3.4 mmol) in dichloromethane (20 mL) at 0° C., stirred at room temperature for 3 hours, and then the solvent was distilled away under a reduced pressure. The residue was purified by silica gel column chromatography (dichloromethane/methanol (v/v)=99/1→90/10) to obtain the title compound (417 mg, 84%) as a pale yellow oily matter.

$^1$H NMR (400 MHz, CDCl$_3$) δ 8.71 (1H, br s), 7.37 (4H, m), 5.85 (1H, br s), 3.68-3.58 (8H, m), 3.49-3.46 (2H, m), 3.00-2.98 (3H, m), 1.73 (2H, br s).

Reference Example 69

Production of tert-butyl N-{2-[2-(2-aminoethoxy)ethoxy]ethyl}carbamate

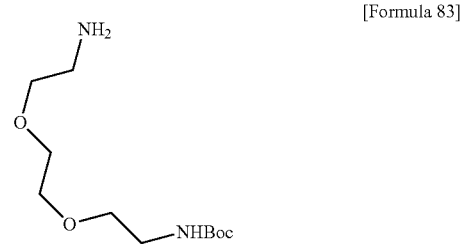 [SMILES: CC(C)(C)OC(=O)NCCOCCOCCN]

[Formula 83]

2,2'-[1,2-Ethane-diyl-bis(oxy)]bis-ethaneamine (2 mL, 13.6 mmol) and diisopropylethylamine (2.4 mL, 13.8 mmol) were added to a solution of di-tert-butyl dicarbonate (30% tetrahydrofuran solution) (5.1 mL, 6.2 mmol) in dichloromethane (29 mL), stirred at room temperature for 4 hours, and then the solvent was distilled away under a reduced pressure. The residue was purified by silica gel column chromatography (dichloromethane/methanol/triethylamine (v/v/v)=18/1/1) to obtain the title compound (810 mg, 53%) as a pale yellow oily matter.

$^1$H NMR (400 MHz, CDCl$_3$) δ 5.13 (1H, br s), 3.62-3.49 (10H, m), 3.33 (2H, br s), 2.88 (2H, t, J=5.2 Hz), 1.45 (9H, s).

Reference Example 70

Production of tert-butyl (2-{2-[2-(dimethylamino)ethoxy]ethoxy}ethyl)carbamate

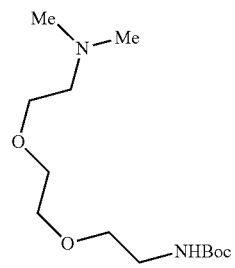

[Formula 84]

Sodium triacetoxyborohydride (1.04 g, 4.9 mmol) was added to a solution of tert-butyl {2-[2-(2-aminoethoxy)ethoxy]ethyl}carbamate (810 mg, 3.3 mmol), formaldehyde (37% aqueous solution) (8 mL, 98.6 mmol) and acetic acid (5.6 mL, 97.9 mmol) in methanol (20 mL) at 0° C., stirred at room temperature for 3 hours, and then a saturated potassium carbonate aqueous solution was added. This solution was extracted with dichloromethane/methanol (v/v)=10/1, the organic layer was dried with anhydrous sodium sulfate, and then the solvent was distilled away under a reduced pressure. The residue was purified by silica gel column chromatography (dichloromethane/methanol (v/v)=4/1) to obtain the title compound (277.5 mg, 31%) as a pale yellow oily matter.

¹H NMR (400 MHz, CDCl₃) δ 5.22 (1H, br s), 3.63-3.61 (6H, m), 3.54 (2H, br t, J=4.8 Hz), 3.32-3.29 (2H, m), 2.60 (2H, br t, J=5.6 Hz), 2.33 (6H, s), 1.44 (9H, 9s).

Reference Example 71

Production of 2-[2-(2-aminoethoxy)ethoxy]-N,N-dimethylethanamine

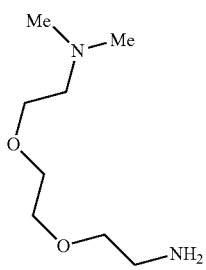

[Formula 85]

Trifluoroacetic acid (2.5 mL, 14.7 mmol) was added to a solution of tert-butyl (2-{2-[2-(dimethylamino)ethoxy]ethoxy}ethyl)carbamate (236 mg, 0.85 mmol) in dichloromethane (2.5 mL), stirred at room temperature for 1 hour, and then the solvent was distilled away under a reduced pressure. The residue was dissolved in methanol, and prepared to be basic with a 3N sodium hydroxide aqueous solution. This solution was extracted with dichloromethane/methanol (v/v)=10/1, the organic layer was dried with anhydrous sodium sulfate, and then the solvent was distilled away under reduced pressure to obtain the title compound (137.2 mg, 91%) as a pale yellow oily matter.

¹H NMR (400 MHz, CDCl₃) δ 3.63-3.60 (4H, m), 3.58 (2H, t, J=5.6 Hz), 3.51 (2H, t, J=5.2 Hz), 2.87-2.86 (2H, m), 2.52 (2H, t, J=5.6 Hz), 2.26 (s, 6H).

Reference Example 72

Production of 1-(2-{2-[2-(dimethylamino)ethoxy]ethoxy}ethyl)-3-(4-ethynylphenyl)urea

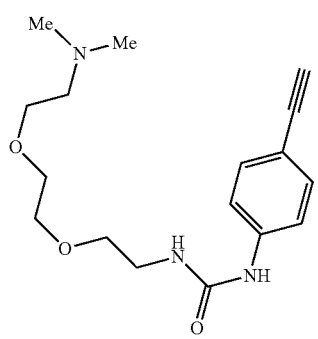

[Formula 86]

4-Nitrophenyl chloroformate (516 mg, 2.6 mmol), dichloromethane (25 mL), 4-ethynylaniline (300 mg, 2.6 mmol) and pyridine (206 μL, 2.6 mmol) were added, stirred at room temperature for 3 hours, and then the solvent was distilled away under a reduced pressure. To a solution of the resulting crude product in dichloromethane (4 mL), a solution of 2-[2-(2-aminoethoxy)ethoxy]-N,N-dimethylethanamine (600 mg, 3.4 mmol) in dichloromethane (25 mL) and triethylamine (356.8 μL, 2.6 mmol) were added, stirred at room temperature for 3 hours, and then the solvent was distilled away under a reduced pressure. The residue was purified by silica gel column chromatography (dichloromethane/methanol (v/v)=99/1-90/10) to obtain the title compound (201 mg, 26%) as a white solid.

¹H NMR (400 MHz, CDCl₃) δ 9.17 (1H, br s), 7.55 (2H, br d, J=8.4 Hz), 7.35 (2H, br d, J=8.4 Hz), 6.70 (1H, br t, J=4.8 Hz), 4.01-3.99 (2H, m), 3.68-3.66 (2H, m), 3.63-3.61 (2H, m), 3.58 (2H, br t, J=4.8 Hz), 3.47-3.43 (2H, m), 3.27-3.25 (2H, m), 2.99 (1H, s), 2.88 (6H, s).

Reference Example 73

Production of N-[2-(2-{2-[3-(4-ethynylphenyl)ureido]ethoxy}ethoxy)ethyl]acetamide

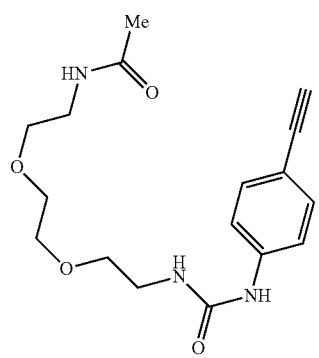

[Formula 87]

Anhydrous acetic acid (48.2 μL, 0.51 mmol) and 4-dimethylaminopyridine (8.3 mg, 0.068 mmol) were added to a solution of 1-{2-[2-(2-aminoethoxy)ethoxy]ethyl}-3-(4-ethynylphenyl)urea (100 mg, 0.34 mmol) in acetonitrile (2 mL), stirred at room temperature for 8 hours, and then the solvent was distilled away under a reduced pressure. The residue was purified by silica gel column chromatography (dichloromethane/methanol (v/v)=98/2→90/10) to obtain the title compound (75.2 mg, 66%) as a pale yellow oily matter.

¹H NMR (400 MHz, CDCl₃) δ 8.51 (1H, br s), 7.43 (2H, br d, J=8.8 Hz), 7.38 (2H, br d, J=8.8 Hz), 5.94 (1H, br s), 5.69 (1H, br s), 3.68-3.55 (8H, m), 3.49-3.46 (4H, m), 2.99 (1H, s), 2.04 (3H, s).

Reference Example 74

Production of oxybis(ethane-2,1-diyl) bis(4-methylbenzenesulfonate)

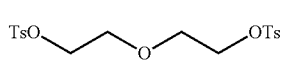

[Formula 88]

Diethylene glycol (980 μL, 9.4 mmol) and p-toluenesulfonyl chloride (3.58 g, 18.8 mmol) were added to a solution of potassium hydroxide (4.23 g, 75.4 mmol) in dichloromethane (20 mL) at 0° C., and stirred at 0° C. for 3 hours. The solution was diluted with water and extraction was carried out with dichloromethane. The organic layer was washed with water, then dried with anhydrous sodium sulfate, and the solvent was distilled away under a reduced pressure to obtain the title compound (3.38 g, 87%) as a white solid.

$^1$H NMR (400 MHz, CDCl$_3$) δ 7.78 (4H, d, J=8.4 Hz), 7.35 (4H, d, J=8.4 Hz), 4.09 (4H, t, J=4.8 Hz), 3.61 (4H, t, J=4.8 Hz), 2.45 (6H, s).

Reference Example 75

Production of 1-(4-ethynylphenyl)-3-{2-[2-(2-morpholinoethoxy)ethoxy]ethyl}urea

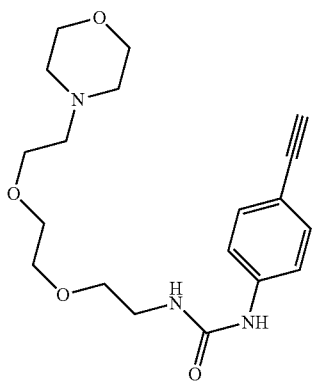

[Formula 89]

Oxybis(ethane-2,1-diyl) bis(4-methylbenzenesulfonate) (233.8 mg, 0.56 mmol) and potassium carbonate (97.4 mg, 0.71 mmol) were added to a solution of 1-{2-[2-(2-aminoethoxy)ethoxy]ethyl}-3-(4-ethynylphenyl)urea (136 mg, 0.47 mmol) in acetonitrile (5 mL), stirred under heat reflux for 16 hours, and then the solvent was distilled away under a reduced pressure. Water was added to the residue, and extraction was carried out with a dichloromethane/methanol (v/v)=10/1 solution. The organic layer was dried with anhydrous sodium sulfate, and the solvent was distilled away under a reduced pressure. The residue was purified by silica gel column chromatography (dichloromethane/methanol (v/v)=99/1→90/10) to obtain the title compound (116.1 mg, 68%) as a colorless oily matter.

$^1$H NMR (400 MHz, CDCl$_3$) δ 7.89 (1H, br s), 7.38 (2H, br d, J=8.8 Hz), 7.34 (2H, d, J=8.8 Hz), 5.90 (1H, br s), 3.71-3.69 (4H, m), 3.62-3.60 (6H, m), 3.55 (2H, t, J=4.4 Hz), 3.42-3.41 (2H, m), 3.01 (1H, s), 2.62-2.60 (2H, m), 2.53-2.52 (4H, m).

Example 1

Production of 2-{[3-({3-[3-(2-methoxyethyl)ureido]phenyl}ethynyl)-1H-indazol-6-yl]thio}-N-methylbenzamide (Compound 1)

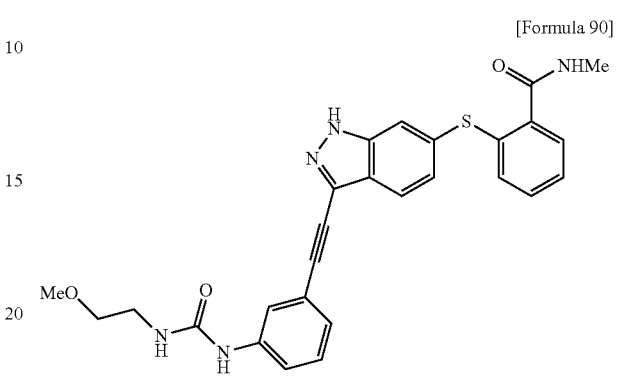

[Formula 90]

N,N-Diisopropylethylamine (0.13 mL, 0.72 mmol) was added to a solution of 2-{(3-iodo-1H-indazol-6-yl)thio}-N-methylbenzamide (100.0 mg, 0.24 mmol), 1-(3-ethynylphenyl)-3-(2-methoxyethyl)urea (63.3 mg, 0.29 mmol), PdCl$_2$(PPh$_3$)$_2$ (8.4 mg, 0.012 mmol) and CuI (4.6 mg, 0.024 mmol) in N,N-dimethylformamide (2 mL) at room temperature, stirred for 5 minutes, and then stirred 80° C. for 2 hours. The solution was diluted with ethyl acetate, washed with saturated saline, dried with anhydrous sodium sulfate, and the solvent was distilled away under a reduced pressure. The residue was purified by silica gel column chromatography (dichloromethane/methanol (v/v)=95/5→90/10) to obtain the title compound (74.3 mg, 61%) as a brown powder.

$^1$H NMR (400 MHz, CD$_3$OD) δ 7.78 (1H, br d, J=8.4 Hz), 7.69 (1H, t, J=1.6 Hz), 7.59 (1H, br s), 7.48-7.46 (1H, m), 7.40-7.19 (7H, m), 3.49 (2H, t, J=5.6 Hz), 3.40-3.37 (5H, m), 2.85 (3H, s).

Example 2

Production of 2-({3-[(3-{3-[2-(2-methoxyethoxy)ethyl]ureido}phenyl)ethynyl]-1H-indazol-6-yl}thio)-N-methylbenzamide (Compound 2)

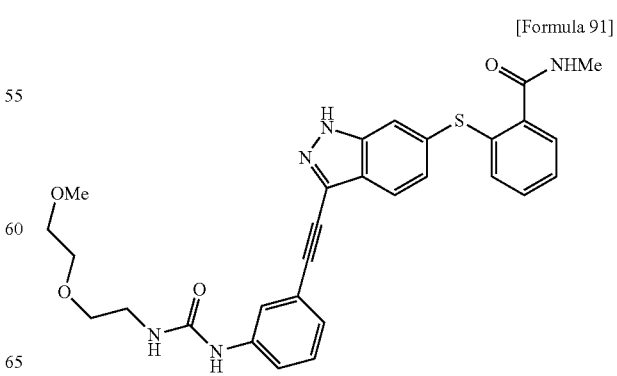

[Formula 91]

2-{(3-Iodo-1H-indazol-6-yl)thio}-N-methylbenzamide (100.0 mg, 0.24 mmol), 1-(3-ethynylphenyl)-3-[2-(2-methoxyethoxy)ethyl]urea (76.1 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (72.6 mg, 55%) as a pale orange powder.

$^1$H NMR (400 MHz, DMSO-d$_6$) δ 13.55 (1H, br s), 8.73 (1H, br s), 8.36 (1H, br q, J=4.8 Hz), 7.81 (1H, br d, J=8.4 Hz), 7.78 (1H, br s), 7.61 (1H, br s), 7.49 (1H, dd, J=7.6, 2.0 Hz), 7.37-7.27 (4H, m), 7.21-7.17 (2H, m), 7.05 (1H, br dd, J=7.6, 2.0 Hz), 6.25 (1H, br t, J=5.2 Hz), 3.56-3.53 (2H, m), 3.48-3.45 (4H, m), 3.28-3.24 (5H, m), 2.76 (3H, d, J=4.8 Hz).

Example 3

Production of 2-[(3-{[3-(3-{2-[2-(2-methoxyethoxy)ethoxy]ethyl}ureido)phenyl]ethynyl}-1H-indazol-6-yl)thio]-N-methylbenzamide (Compound 3)

[Formula 92]

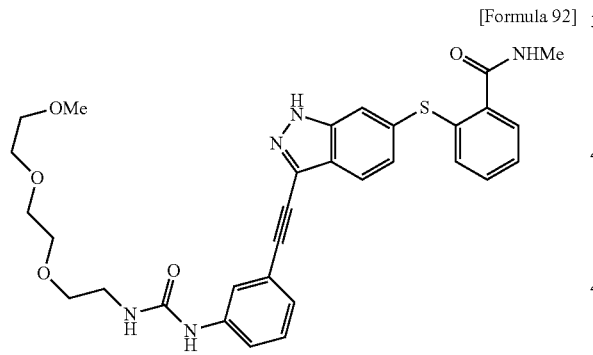

2-{(3-Iodo-1H-indazol-6-yl)thio}-N-methylbenzamide (100.0 mg, 0.24 mmol), 1-(3-ethynylphenyl)-3-{2-[2-(2-methoxyethoxy)ethoxy]ethyl}urea (88.8 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (58.5 mg, 41%) as a white powder.

$^1$H NMR (400 MHz, DMSO-d$_6$) δ 13.55 (1H, br s), 8.72 (1H, br s), 8.35 (1H, br q, J=4.8 Hz), 7.81 (1H, br d, J=8.4 Hz), 7.78 (1H, br s), 7.61 (1H, br s), 7.49 (1H, dd, J=7.6, 2.0 Hz), 7.37-7.27 (4H, m), 7.21-7.17 (2H, m), 7.05 (1H, dd, J=7.6, 2.0 Hz), 6.25 (1H, br t, J=5.2 Hz), 3.54-3.51 (6H, m), 3.47-3.43 (4H, m), 3.29-3.24 (5H, m), 2.76 (3H, d, J=4.8 Hz).

Example 4

Production of 2-{[(3-({3-[3-(2,5,8,11-tetraoxatridecane-13-yl)ureido]phenyl}ethynyl)-1H-indazol-6-yl]thio}-N-methylbenzamide (Compound 4)

[Formula 93]

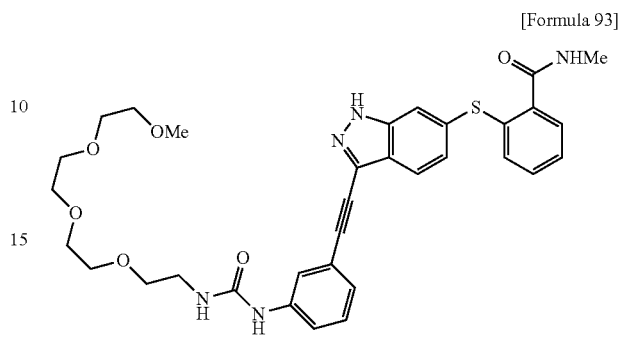

2-{(3-Iodo-1H-indazol-6-yl)thio}-N-methylbenzamide (100.0 mg, 0.24 mmol), 1-(3-ethynylphenyl)-3-(2,5,8,11-tetraoxatridecane-13-yl)urea (102.6 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (29.5 mg, 19%) as a pale yellow solid.

$^1$H NMR (400 MHz, CD$_3$OD) δ 7.78 (1H, d, J=8.8 Hz), 7.70 (1H, br s), 7.59 (1H, br s), 7.47 (1H, br d, J=7.2 Hz), 7.40 (1H, br d, J=8.0 Hz), 7.35-7.23 (6H, m), 3.65-3.58 (12H, m), 3.54-3.51 (2H, m), 3.39 (2H, t, J=5.2 Hz), 3.33 (3H, s), 2.85 (3H, s).

Example 5

Production of 2-{[3-({3-[3-(2,5,8,11,14-pentaoxahexadecane-16-yl)ureido]phenyl}ethynyl)-1H-indazol-6-yl]thio}-N-methylbenzamide (Compound 5)

[Formula 94]

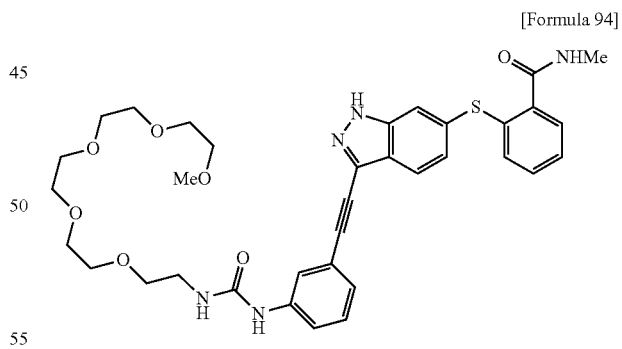

2-{(3-Iodo-1H-indazol-6-yl)thio}-N-methylbenzamide (150.0 mg, 0.37 mmol), 1-(3-ethynylphenyl)-3-(2,5,8,11,14-pentaoxahexadecane-16-yl)urea (173.0 mg, 0.44 mmol), PdCl$_2$(PPh$_3$)$_2$ (13.0 mg, 0.019 mmol), CuI (6.9 mg, 0.036 mmol), N,N-dimethylformamide (2 mL) and N,N-diisopropylethylamine (0.19 mL, 1.1 mmol) were used as raw materials, and treated in the same way as Example 1 to obtain the title compound (43.6 mg, 18%) as a pale yellow solid.

$^1$H NMR (400 MHz, CDCl$_3$) δ 10.48 (1H, br s), 7.83 (1H, br, s), 7.81 (1H, d, J=8.4 Hz), 7.69 (1H, br s), 7.65-7.63 (1H, m), 7.56 (1H, dt, J=8.0, 1.8 Hz), 7.51 (1H, br s), 7.32-7.19 (6H, m), 6.34 (1H, br m), 6.02 (1H, br s), 3.77-3.74 (4H, m), 3.70-3.63 (6H, m), 3.61-3.59 (6H, m), 3.50-3.44 (4H, m), 3.27 (3H, s), 2.95 (3H, d, J=4.8 Hz).

Example 6

Production of 2-{[3-({4-[3-(2-methoxyethyl)ureido] phenyl}ethynyl)-1H-indazol-6-yl]thio}-N-methylbenzamide (Compound 6)

[Formula 95]

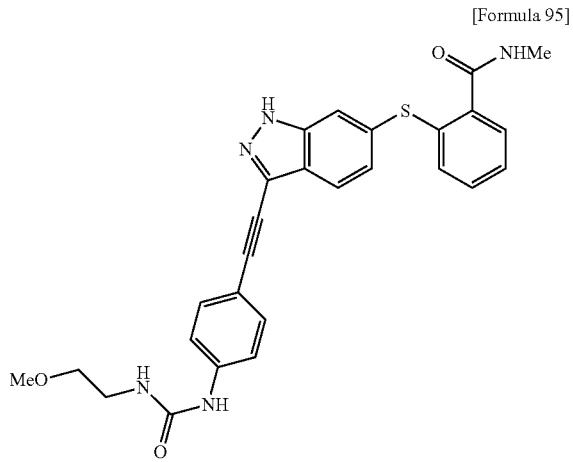 [SMILES: CNC(=O)c1ccccc1Sc1ccc2c(C#Cc3ccc(NC(=O)NCCOC)cc3)n[nH]c2c1]

2-{(3-Iodo-1H-indazol-6-yl)thio}-N-methylbenzamide (104.6 mg, 0.26 mmol), 1-(4-ethynylphenyl)-3-(2-methoxyethyl)urea (108.5 mg, 0.50 mmol), PdCl$_2$(PPh$_3$)$_2$ (5.8 mg, 0.0083 mmol), CuI (2.7 mg, 0.014 mmol), N,N-dimethylformamide (1 mL) and N,N-diisopropylethylamine (0.15 mL, 0.86 mmol) were used as raw materials, and treated in the same way as Example 1 to obtain the title compound (77.8 mg, 61%) as a white powder.

$^1$H NMR (400 MHz, DMSO-d$_6$) δ 13.46 (1H, br s), 8.82 (1H, s), 8.36 (1H, q, J=4.8 Hz), 7.82 (1H, d, J=8.8 HZ), 7.60 (1H, br s), 7.51 (2H, br d, J=8.8 Hz), 7.49-7.46 (3H, m), 7.32 (1H, td, J=7.2, 1.6 Hz), 7.29 (1H, td, J=7.2, 1.6 Hz), 7.18 (1H, dd, J=8.8, 1.6 Hz), 7.05 (1H, dd, J=7.2, 1.6 Hz), 6.30 (1H, t, J=5.6 Hz), 3.39 (2H, t, J=5.6 Hz), 3.29 (3H, s), 3.26 (2H, m), 2.76 (3H, d, J=4.8 Hz).

Example 7

Production of 2-({3-[(4-{3-[2-(2-methoxyethoxy) ethyl]ureido}phenyl)ethynyl]-1H-indazol-6-yl}thio)-N-methylbenzamide (Compound 7)

[Formula 96]

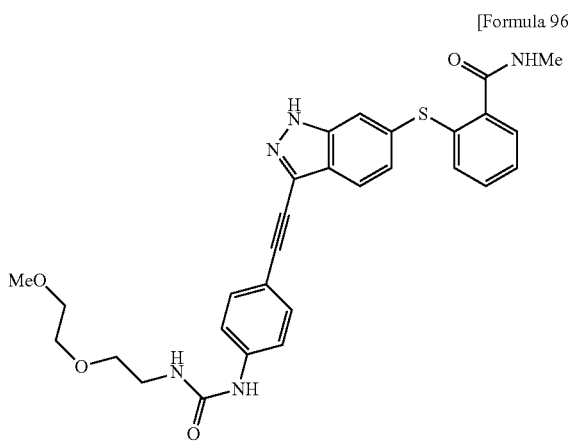 [SMILES: CNC(=O)c1ccccc1Sc1ccc2c(C#Cc3ccc(NC(=O)NCCOCCOC)cc3)n[nH]c2c1]

2-{(3-Iodo-1H-indazol-6-yl)thio}-N-methylbenzamide (102.5 mg, 0.25 mmol), 1-(4-ethynylphenyl)-3-[2-(2-methoxyethoxy)ethyl]urea (132.5 mg, 0.51 mmol), PdCl$_2$(PPh$_3$)$_2$ (5.3 mg, 0.0076 mmol), CuI (3.1 mg, 0.016 mmol), N,N-dimethylformamide (0.8 mL) and N,N-diisopropylethylamine (0.15 mL, 0.086 mmol) were used as raw materials, and treated in the same way as Example 1 to obtain the title compound (51.2 mg, 38%) as a white powder.

$^1$H NMR (400 MHz, DMSO-d$_6$) δ 13.47 (1H, br s), 8.86 (1H, s), 8.36 (1H, q, J=4.8 Hz), 7.82 (1H, d, J=8.4 HZ), 7.60 (1H, br s), 7.53-7.44 (5H, m), 7.32 (1H, td, J=7.6, 1.2 Hz), 7.29 (1H, td, J=7.6, 1.2 Hz), 7.18 (1H, dd, J=8.4, 1.2 Hz), 7.05 (1H, dd, J=7.6, 1.2 Hz), 6.29 (1H, t, J=5.6 Hz), 3.56-3.54 (2H, m), 3.48-3.45 (4H, m), 3.27 (2H, m), 3.26 (3H, s), 2.76 (3H, d, J=4.8 Hz).

Example 8

Production of 2-[(3-{[4-(3-{2-[2-(2-methoxyethoxy) ethoxy]ethyl}ureido)phenyl]ethynyl}-1H-indazol-6-yl)thio]-N-methylbenzamide (Compound 8)

[Formula 97]

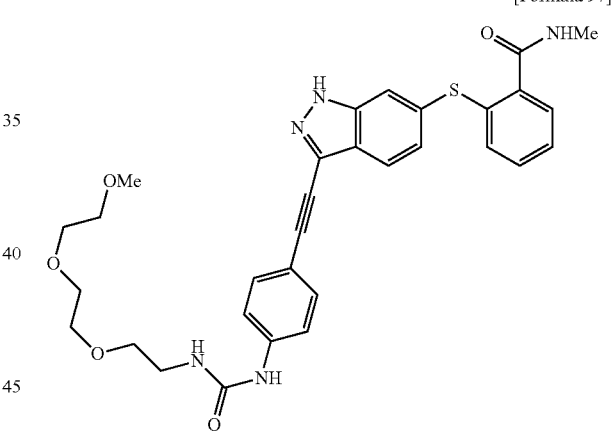

2-{(3-Iodo-1H-indazol-6-yl)thio}-N-methylbenzamide (104.4 mg, 0.26 mmol), 1-(4-ethynylphenyl)-3-{2-[2-(2-methoxyethoxy)ethoxy]ethyl}urea (118.6 mg, 0.39 mmol), PdCl$_2$(PPh$_3$)$_2$ (5.6 mg, 0.0080 mmol), CuI (3.0 mg, 0.016 mmol), N,N-dimethylformamide (0.8 mL) and N,N-diisopropylethylamine (0.15 mL, 0.86 mmol) were used as raw materials, and treated in the same way as Example 1 to obtain the title compound (49.9 mg, 33%) as a white powder.

Melting point: 95-96° C.

$^1$H NMR (400 MHz, DMSO-d$_6$) δ 13.46 (1H, br s), 8.83 (1H, s), 8.36 (1H, br q, J=4.4 Hz), 7.81 (1H, d, J=8.4 HZ), 7.60 (1H, br s), 7.52-7.47 (5H, m), 7.32 (1H, td, J=7.6, 1.6 Hz), 7.29 (1H, td, J=7.6, 1.6 Hz), 7.18 (1H, dd, J=8.4, 1.2 Hz), 7.05 (1H, dd, J=7.6, 1.6 Hz), 6.28 (1H, t, J=5.6 Hz), 3.54-3.52 (6H, m), 3.47 (2H, t, J=5.6 Hz), 3.45-3.42 (2H, m), 3.26 (2H, m), 3.24 (3H, s), 2.76 (3H, d, J=4.4 Hz).

Example 9

Production of 2-{[3-({4-[3-(2,5,8,11-tetraoxatridecane-13-yl)ureido]phenyl}ethynyl)-1H-indazol-6-yl]thio}-N-methylbenzamide (Compound 9)

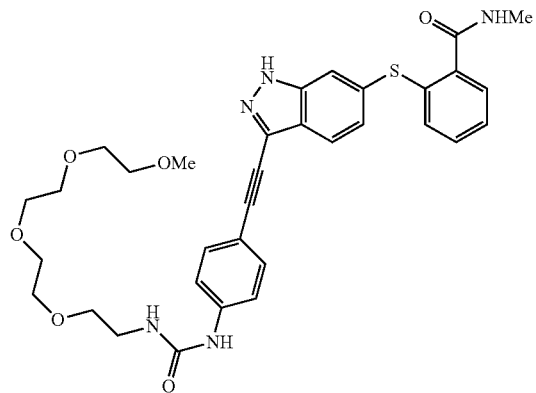

[Formula 98]

2-{(3-Iodo-1H-indazol-6-yl)thio}-N-methylbenzamide (103.8 mg, 0.25 mmol), 1-(4-ethynylphenyl)-3-(2,5,8,11-tetraoxatridecane-13-yl)urea (125.3 mg, 0.32 mmol), PdCl$_2$(PPh$_3$)$_2$ (5.6 mg, 0.0080 mmol), CuI (2.8 mg, 0.015 mmol), N,N-dimethylformamide (0.8 mL) and N,N-diisopropylethylamine (0.15 mL, 0.86 mmol) were used as raw materials, and treated in the same way as Example 1 to obtain the title compound (54.8 mg, 34%) as a pale yellow solid.

$^1$H NMR (400 MHz, DMSO-d$_6$) δ 13.46 (1H, br s), 8.83 (1H, s), 8.36 (1H, q, J=4.4 Hz), 7.82 (1H, d, J=8.4 Hz), 7.60 (1H, br s), 7.53-7.47 (5H, m), 7.32 (1H, td, J=7.6, 1.6 Hz), 7.27 (1H, td, J=7.6, 1.6 Hz), 7.17 (1H, dd, J=8.4, 1.2 Hz), 7.05 (1H, dd, J=7.6, 1.6 Hz), 6.28 (1H, t, J=5.6 Hz), 3.55-3.50 (10H, m), 3.47 (2H, br t, J=5.6 Hz), 3.43-3.41 (2H, m), 3.26 (2H, m), 3.23 (3H, s), 2.76 (3H, d, J=4.4 Hz).

Example 10

Production of 2-{[3-({4-[3-(2,5,8,11,14-pentaoxahexadecane-16-yl)ureido]phenyl}ethynyl)-1H-indazol-6-yl]thio}-N-methylbenzamide (Compound 10)

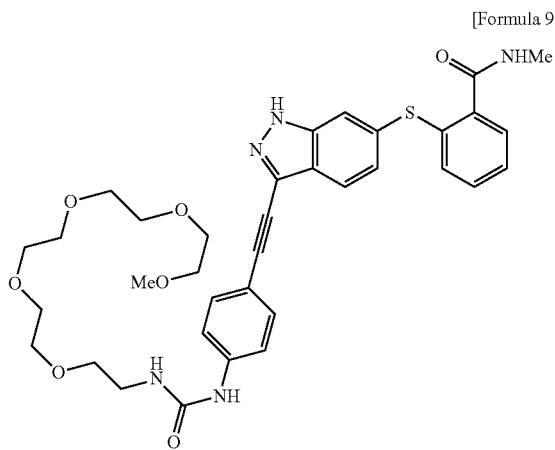

[Formula 99]

2-{(3-Iodo-1H-indazol-6-yl)thio}-N-methylbenzamide (101.7 mg, 0.25 mmol), 1-(4-ethynylphenyl)-3-(2,5,8,11,14-pentaoxahexadecane-16-yl)urea (114.4 mg, 0.33 mmol), PdCl$_2$(PPh$_3$)$_2$ (5.8 mg, 0.0083 mmol), CuI (2.8 mg, 0.015 mmol), N,N-dimethylformamide (0.8 mL) and N,N-diisopropylethylamine (0.15 mL, 0.86 mmol) were used as raw materials, and treated in the same way as Example 1 to obtain the title compound (48.2 mg, 29%) as an orange solid.

$^1$H NMR (400 MHz, DMSO-d$_6$) δ 13.46 (1H, br s), 8.83 (1H, s), 8.36 (1H, q, J=4.8 Hz), 7.82 (1H, d, J=8.4 Hz), 7.60 (1H, br s), 7.52-7.47 (5H, m), 7.31 (1H, td, J=7.6, 1.6 Hz), 7.29 (1H, td, J=7.6, 1.6 Hz), 7.18 (1H, dd, J=8.4, 1.2 Hz), 7.05 (1H, dd, J=7.6, 1.6 Hz), 6.28 (1H, t, J=5.6 Hz), 3.55-3.45 (16H, m), 3.43-3.41 (2H, m), 3.27 (2H, m), 3.23 (3H, s), 2.76 (3H, d, J=4.8 Hz).

Example 11

Production of 2-methoxyethyl {3-[(6-{[2-(methylcarbamoyl)phenyl]thio}-1H-indazol-3-yl)ethynyl]phenyl}carbamate (Compound 11)

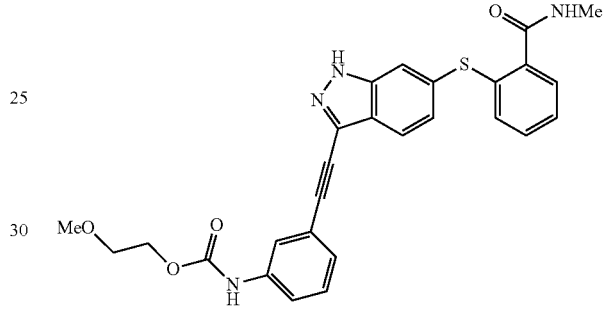

[Formula 100]

2-{(3-Iodo-1H-indazol-6-yl)thio}-N-methylbenzamide (100.0 mg, 0.24 mmol), 2-methoxyethyl (3-ethynylphenyl)carbamate (63.6 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (72.8 mg, 60%) as a white powder.

$^1$H NMR (400 MHz, CDCl$_3$) δ 11.39 (1H, br s), 7.85 (1H, br s), 7.78 (1H, d, J=8.4 Hz), 7.69-7.53 (5H, m), 7.48-7.46 (1H, m), 7.31-7.25 (2H, m), 7.21-7.17 (2H, m), 6.35 (1H, br q, J=4.8 Hz), 4.36 (2H, br t, J=4.4 Hz), 3.69 (2H, br t, J=4.4 Hz), 3.44 (3H, s), 2.96 (3H, br d, J=4.8 Hz).

Example 12

Production of 2-(2-methoxyethoxy)ethyl {3-[(6-{[2-(methylcarbamoyl)phenyl]thio}-1H-indazol-3-yl)ethynyl] phenyl}carbamate (Compound 12)

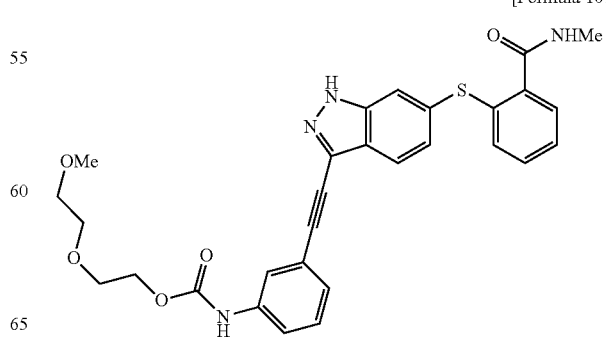

[Formula 101]

2-{(3-Iodo-1H-indazol-6-yl)thio}-N-methylbenzamide (100.0 mg, 0.24 mmol), 2-(2-methoxyethoxy)ethyl (3-ethynylphenyl)carbamate (76.4 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (70.1 mg, 53%) as a white powder.

$^1$H NMR (400 MHz, CDCl$_3$) δ 10.97 (1H, br s), 7.78 (1H, d, J=8.4 Hz), 7.64-7.52 (5H, m), 7.31-7.18 (6H, m), 6.33 (1H, br m), 4.34 (2H, br t, J=4.4 Hz), 3.78 (2H, br t, J=4.4 Hz), 3.72-3.69 (2H, m), 3.59-3.57 (2H, m), 3.36 (3H, s), 2.96 (3H, br d, J=4.8 Hz).

Example 13

Production of 2-[2-(2-methoxyethoxy)ethoxy]ethyl {3-[(6-{[2-(methylcarbamoyl)phenyl]thio}-1H-indazol-3-yl)ethynyl] phenyl}carbamate (Compound 13)

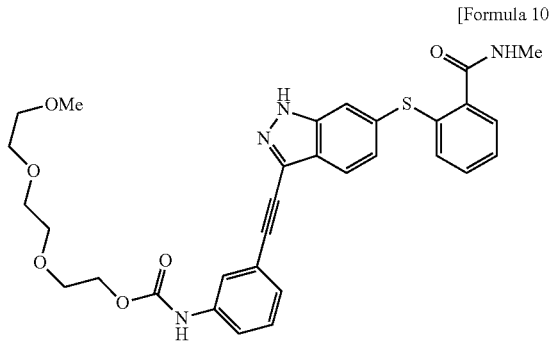

[Formula 102]

2-{(3-Iodo-1H-indazol-6-yl)thio}-N-methylbenzamide (100.0 mg, 0.24 mmol), 2-[2-(2-methoxyethoxy)ethoxy]ethyl (3-ethynylphenyl)carbamate (89.1 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (57.7 mg, 40%) as a pale yellow powder.

$^1$H NMR (400 MHz, CDCl$_3$) δ 11.62 (1H, br s), 7.97 (1H, br s), 7.75 (1H, br d, J=8.4 Hz), 7.62-7.59 (4H, m), 7.28-7.16 (6H, m), 6.43 (1H, br m), 4.31 (2H, br t, J=4.4 Hz), 3.76 (2H, br t, J=4.4 Hz), 3.72-3.70 (2H, m), 3.68-3.66 (2H, m), 3.62-3.60 (2H, m), 3.49-3.47 (2H, m), 3.29 (3H, s), 2.96 (3H, br d, J=4.8 Hz).

Example 14

Production of 2-methoxyethyl {4-[(6-{[2-(methylcarbamoyl)phenyl]thio}-1H-indazol-3-yl)ethynyl]phenyl}carbamate (Compound 14)

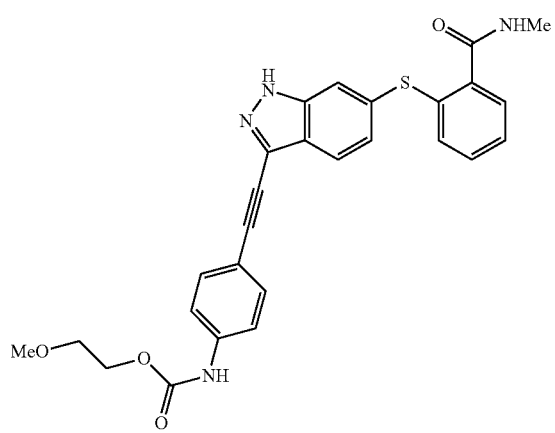

[Formula 103]

2-{(3-Iodo-1H-indazol-6-yl)thio}-N-methylbenzamide (101.2 mg, 0.25 mmol), 2-methoxyethyl (4-ethynylphenyl)carbamate (88.8 mg, 0.41 mmol), PdCl$_2$(PPh$_3$)$_2$ (5.9 mg, 0.0084 mmol), CuI (2.7 mg, 0.014 mmol), N,N-dimethylformamide (0.8 mL) and N,N-diisopropylethylamine (0.15 mL, 0.86 mmol) were used as raw materials, and treated in the same way as Example 1 to obtain the title compound (69.8 mg, 56%) as a pale yellow powder.

$^1$H NMR (400 MHz, DMSO-d$_6$) δ 13.49 (1H, br s), 10.02 (1H, s), 8.36 (1H, q, J=4.8 Hz), 7.82 (1H, d, J=8.4 Hz), 7.60-7.55 (5H, m), 7.49-7.48 (1H, m), 7.32 (1H, td, J=7.6, 1.6 Hz), 7.29 (1H, td, J=7.6, 1.6 Hz), 7.18 (1H, dd, J=8.4, 1.6 Hz), 7.05 (1H, dd, J=7.6, 1.6 Hz), 4.23 (2H, br t, J=4.8 Hz), 3.58 (2H, br t, J=4.8 Hz), 3.29 (3H, s), 2.76 (3H, d, J=4.8 Hz).

Example 15

Production of 2-(2-methoxyethoxy)ethyl {4-[(6-{[2-(methylcarbamoyl)phenyl]thio}-1H-indazol-3-yl)ethynyl]phenyl}carbamate (Compound 15)

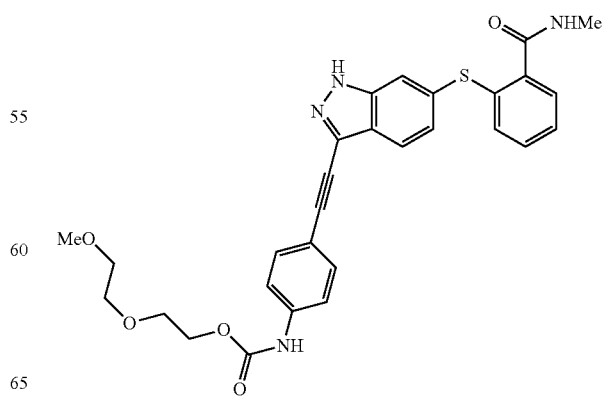

[Formula 104]

2-{(3-Iodo-1H-indazol-6-yl)thio}-N-methylbenzamide (101.2 mg, 0.25 mmol), 2-(2-methoxyethoxy)ethyl (4-ethynylphenyl)carbamate (102.4 mg, 0.39 mmol), PdCl$_2$(PPh$_3$)$_2$ (5.3 mg, 0.0076 mmol), CuI (2.8 mg, 0.015 mmol), N,N-dimethylformamide (1.0 mL) and N,N-diisopropylethylamine (0.15 mL, 0.86 mmol) were used as raw materials, and treated in the same way as Example 1 to obtain the title compound (79.4 mg, 59%) as a white powder.

$^1$H NMR (400 MHz, DMSO-d$_6$) δ 13.48 (1H, br s), 10.01 (1H, s), 8.35 (1H, q, J=4.4 Hz), 7.81 (1H, d, J=8.4 Hz), 7.59-7.54 (5H, m), 7.49-7.46 (1H, m), 7.32 (1H, td, J=7.6, 1.6 Hz), 7.27 (1H, td, J=7.6, 1.6 Hz), 7.17 (1H, dd, J=8.4, 1.2 Hz), 7.04 (1H, dd, J=7.6, 1.6 Hz), 4.22 (2H, br t, J=4.8 Hz), 3.65 (2H, br t, J=4.8 Hz), 3.57-3.54 (2H, m), 3.46-3.43 (2H, m), 3.24 (3H, s), 2.75 (3H, d, J=4.4 Hz).

Example 16

Production of 2-[2-(2-methoxyethoxy)ethoxy]ethyl {4-[(6-{[2-(methylcarbamoyl)phenyl]thio}-1H-indazol-3-yl)ethynyl]phenyl}carbamate (Compound 16)

[Formula 105]

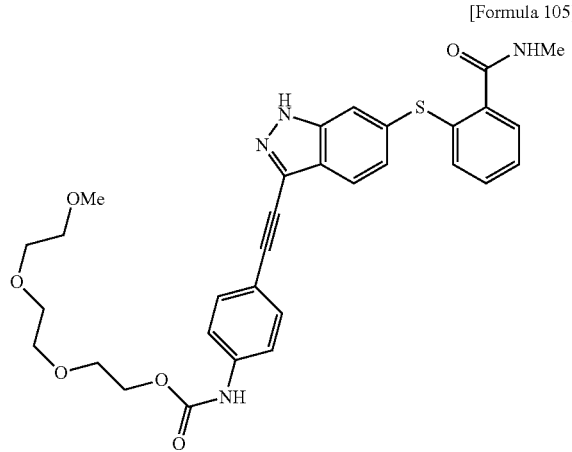

2-{(3-Iodo-1H-indazol-6-yl)thio}-N-methylbenzamide (101.5 mg, 0.25 mmol), 2-[2-(2-methoxyethoxy)ethoxy]ethyl (4-ethynylphenyl)carbamate (122.7 mg, 0.40 mmol), PdCl$_2$(PPh$_3$)$_2$ (5.7 mg, 0.0081 mmol), CuI (2.9 mg, 0.015 mmol), N,N-dimethylformamide (1.0 mL) and N,N-diisopropylethylamine (0.15 mL, 0.86 mmol) were used as raw materials, and treated in the same way as Example 1 to obtain the title compound (90.9 mg, 62%) as a white powder.

Melting point: 103-104° C.

$^1$H NMR (400 MHz, DMSO-d$_6$) δ 13.48 (1H, br s), 10.02 (1H, s), 8.35 (1H, q, J=4.8 Hz), 7.81 (1H, d, J=8.4 Hz), 7.59 (1H, br s), 7.56 (4H, br m), 7.48 (1H, dd, J=7.6, 1.6 Hz), 7.31 (1H, td, J=7.6, 1.6 Hz), 7.27 (1H, td, J=7.6. 1.6 Hz), 7.17 (1H, dd, J=8.4, 1.2 Hz), 7.04 (1H, dd, J=7.6, 1.6 Hz), 4.22 (2H, br t, J=4.4 Hz), 3.65 (2H, br t, J=4.4 Hz), 3.57-3.49 (6H, m), 3.42-3.39 (2H, m), 3.22 (3H, s), 2.75 (3H, d, J=4.8 Hz).

Example 17

Production of 2,5,8,11-tetraoxatridecane-13-yl {4-[(6-{[2-(methylcarbamoyl)phenyl]thio}-1H-indazol-3-yl)ethynyl]phenyl}carbamate (Compound 17)

[Formula 106]

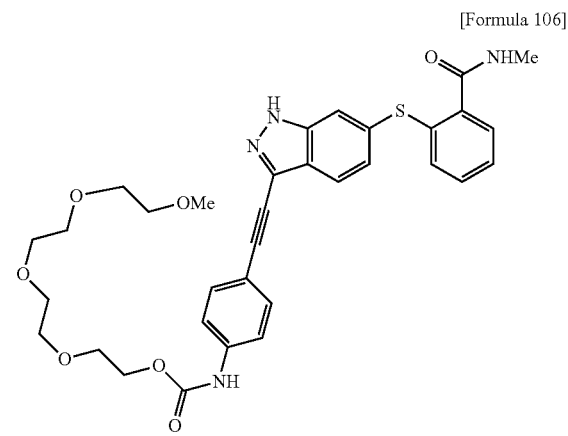 [SMILES: CNC(=O)c1ccccc1Sc1ccc2c(C#Cc3ccc(NC(=O)OCCOCCOCCOCCOC)cc3)n[nH]c2c1]

2-{(3-Iodo-1H-indazol-6-yl)thio}-N-methylbenzamide (103.1 mg, 0.25 mmol), 2,5,8,11-tetraoxatridecane-13-yl (4-ethynylphenyl)carbamate (129.8 mg, 0.37 mmol), PdCl$_2$(PPh$_3$)$_2$ (5.6 mg, 0.0080 mmol), CuI (3.1 mg, 0.016 mmol), N,N-dimethylformamide (0.8 mL) and N,N-diisopropylethylamine (0.15 mL, 0.86 mmol) were used as raw materials, and treated in the same way as Example 1 to obtain the title compound (77.6 mg, 48%) as an orange solid.

$^1$H NMR (400 MHz, DMSO-d$_6$) δ 13.49 (1H, br s), 10.04 (1H, s), 8.36 (1H, q, J=4.8 Hz), 7.82 (1H, br d, J=8.4 Hz), 7.60 (1H, br s), 7.57 (4H, m), 7.50-7.48 (1H, m), 7.35-7.27 (2H, m), 7.18 (1H, dd, J=8.4, 1.2 Hz), 7.05 (1H, dd, J=7.6, 1.6 Hz), 4.24-4.22 (2H, m), 3.68-3.66 (2H, m), 3.57-3.49 (10H, m), 3.43-3.40 (2H, m), 3.23 (3H, s), 2.76 (3H, d, J 4.8 Hz).

Example 18

Production of 2,5,8,11,14-pentaoxahexadecane-16-yl {4-[(6-{[2-(methylcarbamoyl)phenyl]thio}-1H-indazol-3-yl)ethynyl]phenyl}carbamate (Compound 18)

[Formula 107]

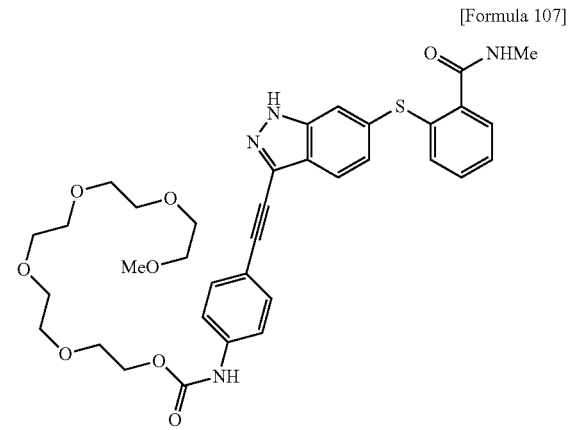 [SMILES: CNC(=O)c1ccccc1Sc1ccc2c(C#Cc3ccc(NC(=O)OCCOCCOCCOCCOCCOC)cc3)n[nH]c2c1]

2-{(3-Iodo-1H-indazol-6-yl)thio}-N-methylbenzamide (107.0 mg, 0.26 mmol), 2,5,8,11,14-pentaoxahexadecane-16-yl (4-ethynylphenyl)carbamate (160.4 mg, 0.41 mmol), PdCl$_2$(PPh$_3$)$_2$ (5.2 mg, 0.0074 mmol), CuI (3.1 mg, 0.016 mmol), N,N-dimethylformamide (0.8 mL) and N,N-diisopropylethylamine (0.15 mL, 0.86 mmol) were used as raw materials, and treated in the same way as Example 1 to obtain the title compound (77.9 mg, 44%) as an orange solid.

$^1$H NMR (400 MHz, DMSO-d$_6$) δ 13.49 (1H, br s), 10.04 (1H, s), 8.36 (1H, q, J=4.8 Hz), 7.82 (1H, d, J=8.4 Hz), 7.60 (1H, br s), 7.57 (4H, m), 7.49-7.48 (1H, m), 7.32 (1H, td, J=7.6, 2.0 Hz), 7.29 (1H, td, J=7.6, 2.0 Hz), 7.18 (1H, dd, J=8.4, 1.6 Hz), 7.05 (1H, dd, J=7.6, 2.0 Hz), 4.23 (2H, br t, J=4.4 Hz), 3.67 (2H, br t, J=4.4 Hz), 3.58-3.48 (14H, m), 3.43-3.40 (2H, m), 3.23 (3H, s), 2.76 (3H, d, J=4.8 Hz).

Example 19

Production of N-{3-[(6-{[2-(methylcarbamoyl)phenyl]thio}-1H-indazol-3-yl)ethynyl]phenyl}-2,5,8,11,14,17-hexaoxanonadecane-19-amide (Compound 19)

[Formula 108]

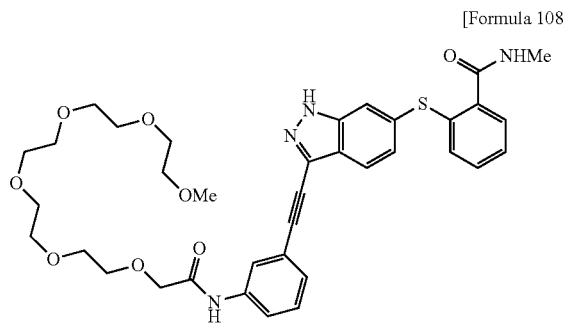 [SMILES: CNC(=O)c1ccccc1Sc1ccc2c(C#Cc3cccc(NC(=O)COCCOCCOCCOCCOCCOC)c3)n[nH]c2c1]

2-{(3-Iodo-1H-indazol-6-yl)thio}-N-methylbenzamide (100.5 mg, 0.25 mmol), PdCl$_2$(PPh$_3$)$_2$ (5.2 mg, 0.0074 mmol), CuI (2.6 mg, 0.014 mmol), N,N-dimethylformamide (1.7 mL), N-(3-ethynylphenyl)-2,5,8,11,14,17-hexaoxanonadecane-19-amide (140.1 mg, 0.34 mmol) and N,N-diisopropylethylamine (0.15 mL, 0.86 mmol) were used as raw materials, and treated in the same way as Example 1 to obtain the title compound (33.0 mg, 19%) as an orange solid.

$^1$H NMR (400 MHz, DMSO-d$_6$) δ 13.58 (1H, br s), 9.77 (1H, s), 8.37 (1H, q, J=4.4 Hz), 7.99 (1H, br t, J=1.6 Hz), 7.82 (1H, d, J=8.4 Hz), 7.70 (1H, dt, J=7.6, 1.6 Hz), 7.62 (1H, br s), 7.50-7.48 (1H, m), 7.42 (1H, t, J=7.6 Hz), 7.38 (1H, dt, J=7.6, 1.6 Hz), 7.33 (1H, td, J=7.6, 1.6 Hz), 7.29 (1H, td, J=7.6, 1.6 Hz), 7.20 (1H, dd, J=8.4, 1.6 Hz), 7.07-7.05 (1H, m), 4.11 (2H, s), 3.70-3.68 (2H, m), 3.64-3.62 (2H, m), 3.58-3.54 (4H, m), 3.51-3.47 (10H, m), 3.41-3.39 (2H, m), 3.22 (3H, s), 2.76 (3H, d, J=4.4 Hz).

Example 20

Production of N-{4-[(6-{[2-(methylcarbamoyl)phenyl]thio}-1H-indazol-3-yl)ethynyl]phenyl}-2,5,8,11-tetraoxatridecane-13-amide (Compound 20)

[Formula 109]

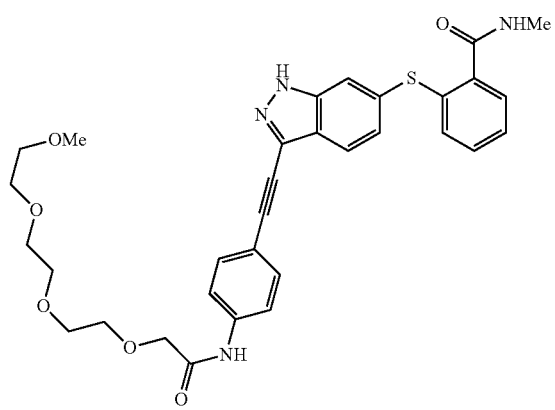

2-{(3-Iodo-1H-indazol-6-yl)thio}-N-methylbenzamide (100.0 mg, 0.24 mmol), N-(4-ethynylphenyl)-2,5,8,11-tetraoxatridecane-13-amide (93.2 mg, 0.29 mmol), PdCl$_2$(PPh$_3$)$_2$ (8.4 mg, 0.012 mmol), CuI (4.6 mg, 0.024 mmol), acetonitrile (1 mL) and triethylamine (1 mL) were used as raw materials, and treated in the same way as Example 1 to obtain the title compound (91.1 mg, 62%) as an orange solid.

$^1$H NMR (400 MHz, DMSO-d$_6$) δ 13.50 (1H, s), 9.84 (1H, s), 8.35 (1H, br q, J=4.4 Hz), 7.83 (1H, d, J=8.4 Hz), 7.75 (2H, br d, J=8.8 Hz), 7.61 (2H, br d, J=8.8 Hz), 7.60 (1H, br s), 7.48 (1H, dd, J=7.2, 2.0 Hz), 7.34-7.26 (2H, m), 7.18 (1H, dd, J=8.4, 1.6 Hz), 7.05 (1H, br d, J=7.2 Hz), 4.11 (2H, s), 3.70-3.67 (2H, m), 3.63-3.61 (2H, m), 3.57-3.51 (6H, m), 3.43-3.41 (2H, m), 3.23 (3H, s), 2.76 (3H, br d, J=4.4 Hz).

Example 21

Production of N-{4-[(6-{[2-(methylcarbamoyl)phenyl]thio}-1H-indazol-3-yl)ethynyl]phenyl}-2,5,8,11,14-pentaoxahexadecane-16-amide (Compound 21)

[Formula 110]

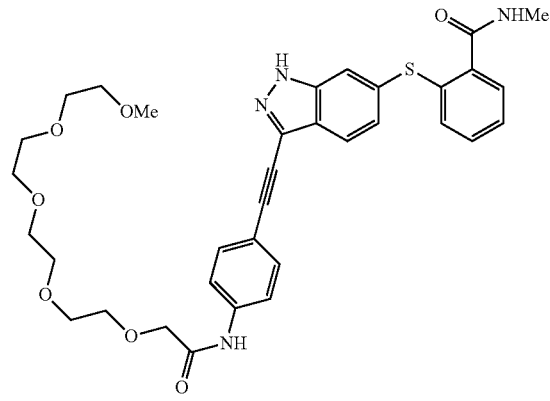

2-{(3-Iodo-1H-indazol-6-yl)thio}-N-methylbenzamide (100.0 mg, 0.24 mmol), N-(4-ethynylphenyl)-2,5,8,11,14-pentaoxahexadecane-16-amide (105.9 mg, 0.29 mmol), PdCl$_2$(PPh$_3$)$_2$ (8.4 mg, 0.012 mmol), CuI (4.6 mg, 0.024 mmol), acetonitrile (1 mL) and triethylamine (1 mL) were used as raw materials, and treated in the same way as Example 1 to obtain the title compound (75.0 mg, 47%) as an orange solid.

$^1$H NMR (400 MHz, DMSO-d$_6$) δ 13.50 (1H, s), 9.83 (1H, s), 8.35 (1H, br q, J=4.4 Hz), 7.83 (1H, br d, J=8.4 Hz), 7.75 (2H, br d, J=8.8 Hz), 7.61 (2H, br d, J=8.8 Hz), 7.60 (1H, br s), 7.49 (1H, dd, J=7.2, 2.0 Hz), 7.34-7.26 (2H, m), 7.18 (1H, dd, J=8.4, 1.6 Hz), 7.05 (1H, br d, J=7.2 Hz), 4.11 (2H, s), 3.70-3.67 (2H, m), 3.64-3.61 (2H, m), 3.57-3.49 (10H, m), 3.42-3.40 (2H, m), 3.22 (3H, s), 2.76 (3H, br d, J=4.4 Hz).

Example 22

Production of N-{4-[(6-{[2-(methylcarbamoyl)phenyl]thio}-1H-indazol-3-yl)ethynyl]phenyl}-2,5,8,11,14,17-hexaoxanonadecane-19-amide (Compound 22)

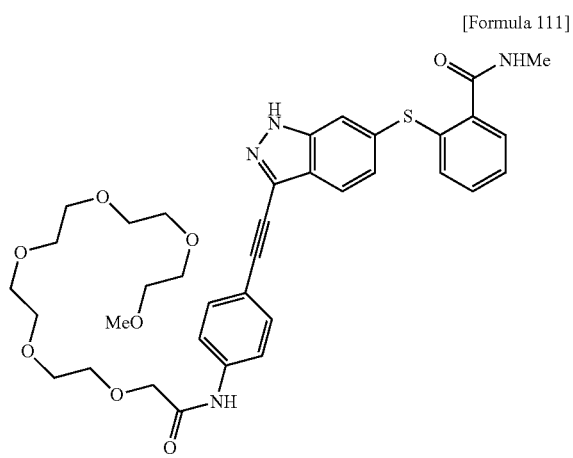 [SMILES: CNC(=O)c1ccccc1Sc1ccc2c(C#Cc3ccc(NC(=O)COCCOCCOCCOCCOCCOC)cc3)n[nH]c2c1]

[Formula 111]

2-{(3-Iodo-1H-indazol-6-yl)thio}-N-methylbenzamide (100.6 mg, 0.25 mmol), PdCl$_2$(PPh$_3$)$_2$ (5.4 mg, 0.0077 mmol), CuI (2.5 mg, 0.013 mmol), N,N-dimethylformamide (0.8 mL), N-(4-ethynylphenyl)-2,5,8,11,14,17-hexaoxanonadecane-19-amide (142.1 mg, 0.35 mmol) and N,N-diisopropylethylamine (0.15 mL, 0.86 mmol) were used as raw materials, and treated in the same way as Example 1 to obtain the title compound (54.7 mg, 32%) as a pale brown solid.

$^1$H NMR (400 MHz, DMSO-d$_6$) δ 13.51 (1H, br s), 9.84 (1H, s), 8.36 (1H, q, J=4.8 Hz), 7.83 (1H, d, J=8.4 Hz), 7.76 (2H, br d, J=8.8 Hz), 7.62-7.60 (3H, m), 7.50-7.48 (1H, m), 7.32 (1H, td, J=7.6, 1.6 Hz), 7.29 (1H, td, J=7.6, 1.6 Hz), 7.18 (1H, dd, J=8.4, 1.6 Hz), 7.06-7.04 (1H, m), 4.11 (2H, s), 3.69-3.67 (2H, m), 3.63-3.61 (2H, m), 3.58-3.53 (4H, m), 3.51-3.48 (10H, m), 3.42-3.39 (2H, m), 3.22 (3H, s), 2.76 (3H, d, J=4.8 Hz).

Example 23

Production of 2-{[3-({3-[(2-methoxyethyl)amino]phenyl}ethynyl)-1H-indazol-6-yl]thio}-N-methylbenzamide (Compound 23)

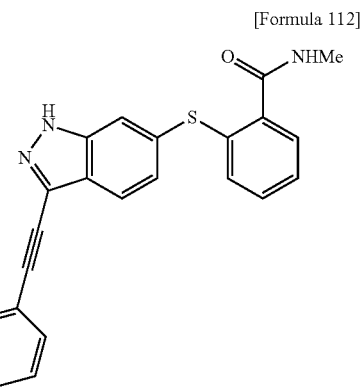

[Formula 112]

2-{(3-Iodo-1H-indazol-6-yl)thio}-N-methylbenzamide (100.0 mg, 0.24 mmol), 3-ethynyl-N-(2-methoxyethyl)aniline (50.8 mg, 0.29 mg), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (15 mg, 10%) as a white powder.

$^1$H NMR (400 MHz, CDCl$_3$) δ 10.08 (1H, br s), 7.82 (1H, d, J=8.4 Hz), 7.66-7.64 (1H, m), 7.48 (1H, br s), 7.33-7.31 (3H, m), 7.22 (1H, dd, J=8.4, 1.6 Hz), 7.17 (1H, t, J=8.0 Hz), 6.99 (1H, br d, J=8.0 Hz), 6.88 (1H, t, J=2.0 Hz), 6.66 (1H, dd, J=8.0, 2.0 Hz), 6.29 (1H, br m), 4.11 (1H, br m), 3.62 (2H, t, J=5.6 Hz), 3.40 (3H, s), 3.34-3.33 (2H, m), 2.95 (3H, d, J=4.8 Hz).

Example 24

Production of 2-({3-[(3-{[2-(2-methoxyethoxy)ethyl]amino}phenyl)ethynyl]-1H-indazol-6-yl}thio)-N-methylbenzamide (Compound 24)

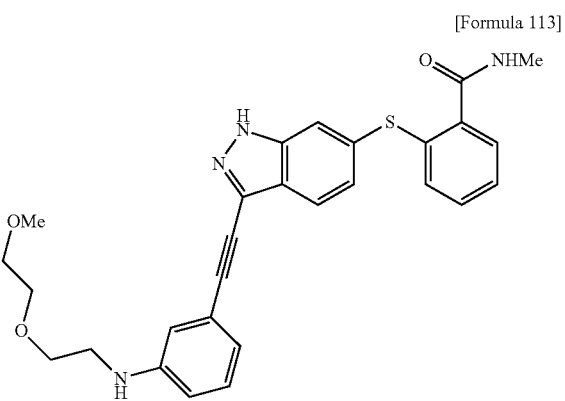 [SMILES: CNC(=O)c1ccccc1Sc1ccc2c(C#Cc3cccc(NCCOCCOC)c3)n[nH]c2c1]

[Formula 113]

2-{(3-Iodo-1H-indazol-6-yl)thio}-N-methylbenzamide (100.0 mg, 0.24 mmol), 3-ethynyl-N-[2-(2-methoxyethoxy)ethyl]aniline (64.2 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (51.4 mg, 42%) as a pale yellow powder.

$^1$H NMR (400 MHz, CDCl$_3$) δ 10.14 (1H, br s), 7.82 (1H, d, J=8.4 Hz), 7.66-7.64 (1H, m), 7.49 (1H, br s), 7.33-7.30 (3H, m), 7.22 (1H, dd, J=8.4, 1.2 Hz), 7.17 (1H, t, J=8.0 Hz), 6.98 (1H, d, J=8.0 Hz), 6.88 (1H, t, J=2.0 Hz), 6.66 (1H, br d, J=8.0 Hz), 6.30 (1H, br m), 4.22 (1H, br m), 3.73 (2H, t, J=5.2 Hz), 3.67-3.65 (2H, m), 3.58-3.56 (2H, m), 3.41 (3H, s), 3.34-3.33 (2H, m), 2.95 (3H, d, J=5.2 Hz).

Example 25

Production of 2-[(3-{[3-({2-[2-(2-methoxyethoxy)ethyl]amino)phenyl]ethynyl}-1H-indazol-6-yl)thio]-N-methylbenzamide (Compound 25)

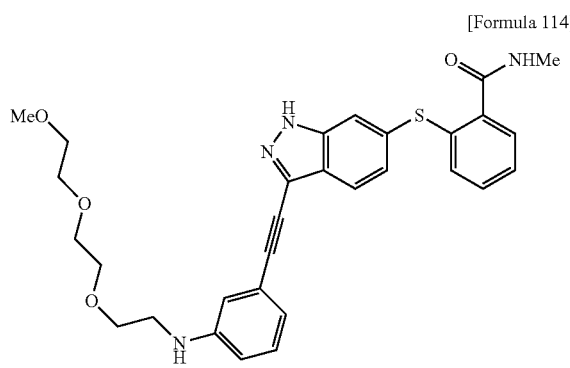 [SMILES: CNC(=O)c1ccccc1Sc1ccc2c(C#Cc3cccc(NCCOCCOCCOC)c3)n[nH]c2c1]

[Formula 114]

2-{(3-Iodo-1H-indazol-6-yl)thio}-N-methylbenzamide (100.0 mg, 0.24 mmol), 3-ethynyl-N-{2-[2-(2-methoxyethoxy)ethoxy]ethyl}aniline (76.4 mg, 0.29 mg), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (47.3 mg, 36%) as a pale yellow solid.

$^1$H NMR (400 MHz, CDCl$_3$) δ 10.70 (1H, br s), 7.81 (1H, d, J=8.4 Hz), 7.63-7.61 (1H, m), 7.59 (1H, br s), 7.29-7.26 (3H, m), 7.22-7.19 (1H, m), 7.16 (1H, t, J=8.0 Hz), 6.97 (1H, d, J=8.0 Hz), 6.87 (1H, t, J=2.0 Hz), 6.65 (1H, dd, J=8.0, 2.0 Hz), 6.32 (1H, br m), 4.26 (1H, br m), 3.72 (2H, d, J=5.2 Hz), 3.67-3.66 (6H, m), 3.57-3.55 (2H, m), 3.38 (3H, s), 3.32-3.31 (2H, m), 2.96 (3H, d, J=4.8 Hz).

Example 26

Production of 2-({3-[(4-{[2-(2-methoxyethoxy)ethyl]amino}phenyl)ethynyl]-1H-indazol-6-yl}thio)-N-methylbenzamide (Compound 26)

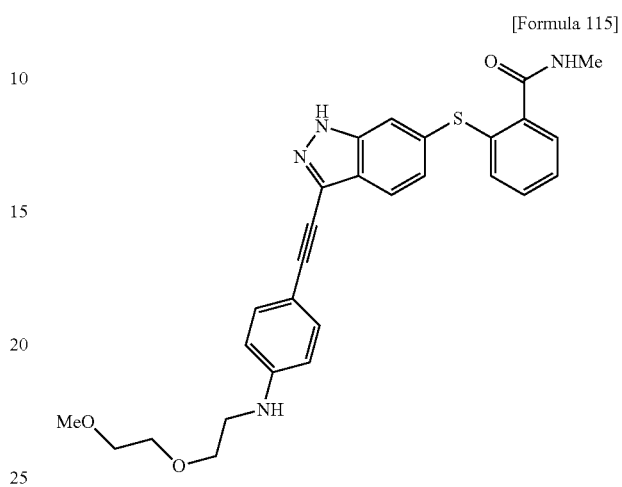

[Formula 115]

2-{(3-Iodo-1H-indazol-6-yl)thio}-N-methylbenzamide (120.0 mg, 0.29 mmol), 4-ethynyl-N-[2-(2-methoxyethoxy)ethyl]aniline (77.0 mg, 0.35 mg), PdCl$_2$(PPh$_3$)$_2$ (10.3 mg, 0.015 mmol), CuI (5.5 mg, 0.029 mmol), N,N-dimethylformamide (2 mL) and N,N-diisopropylethylamine (0.15 mL, 0.88 mmol) were used as raw materials, and treated in the same way as Example 1 to obtain the title compound (11.5 mg, 8%) as a pale yellow powder.

$^1$H NMR (400 MHz, CDCl$_3$) δ 10.36 (1H, br s), 7.81 (1H, br d, J=8.4 Hz), 7.64-7.62 (1H, m), 7.52 (1H, br s), 7.44 (2H, br d, J=8.4 Hz), 7.30-7.28 (2H, m), 7.22-7.18 (2H, m), 6.59 (2H, br d, J=8.4 Hz), 6.31 (1H, br m), 4.40 (1H, br m), 3.72 (2H, t, J=5.2 Hz), 3.67-3.65 (2H, m), 3.58-3.56 (2H, m), 3.41 (3H, s), 3.36-3.34 (2H, m), 2.95 (3H, d, J=4.8 Hz).

Example 27

Production of 2-[(3-{[4-({2-[2-(2-methoxyethoxy)ethyl]amino)phenyl]ethynyl}-1H-indazol-6-yl)thio]-N-methylbenzamide (Compound 27)

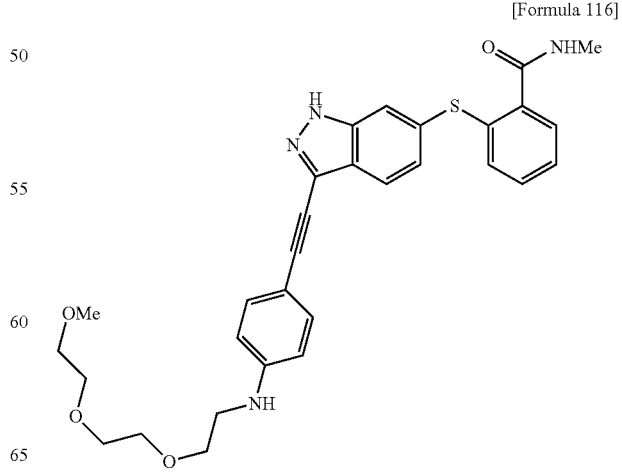

[Formula 116]

2-{(3-Iodo-1H-indazol-6-yl)thio}-N-methylbenzamide (100.0 mg, 0.24 mmol), 4-ethynyl-N-{2-[2-(2-methoxyethoxy)ethoxy]ethyl}aniline (77.0 mg, 0.29 mg), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (41.6 mg, 31%) as a pale yellow solid.

Melting point: 66-67° C.

$^1$H NMR (400 MHz, CDCl$_3$) δ 10.12 (1H, br s), 7.81 (1H, br d, J=8.4 Hz), 7.65-7.63 (1H, m), 7.48 (1H, br s), 7.44 (2H, br d, J=8.8 Hz), 7.32-7.29 (2H, m), 7.24-7.22 (1H, m), 7.20 (1H, dd, J=8.4, 1.2 Hz), 6.60 (2H, br d, J=8.8 Hz), 6.30 (1H, br m), 4.44 (1H, br m), 3.72 (2H, t, J=5.2 Hz), 3.67-3.65 (6H, m), 3.58-3.56 (2H, m), 3.40 (3H, s), 3.35-3.31 (2H, m), 2.95 (3H, d, J=4.8 Hz).

Example 28

Production of 2-{[3-({4-[(2,5,8,11-tetraoxatridecane-13-yl)amino]phenyl}ethynyl)-1H-indazol-6-yl]thio}-N-methylbenzamide (Compound 28)

[Formula 117]

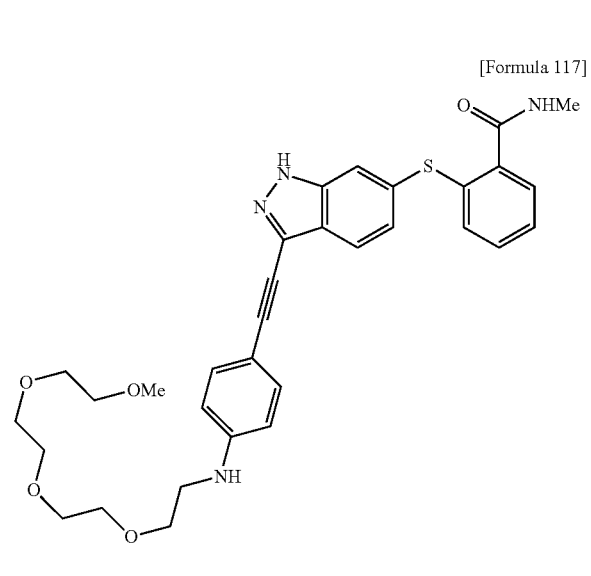 [SMILES: CNC(=O)c1ccccc1Sc1ccc2c(C#Cc3ccc(NCCOCCOCCOCCOC)cc3)n[nH]c2c1]

2-{(3-Iodo-1H-indazol-6-yl)thio}-N-methylbenzamide (100.0 mg, 0.24 mmol), N-(4-ethynylphenyl)-2,5,8,11-tetraoxatridecane-13-amine (100.0 mg, 0.33 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (25.4 mg, 18%) as a brown solid.

$^1$H NMR (400 MHz, CDCl$_3$) δ 11.36 (1H, br s), 7.80 (1H, br d, J=8.4 Hz), 7.68 (1H, br s), 7.59-7.57 (1H, m), 7.42 (2H, br d, J=8.6 Hz), 7.25-7.22 (2H, m), 7.18 (1H, dd, J=8.4, 1.2 Hz), 7.13-7.11 (1H, m), 6.57 (2H, br d, J=8.6 Hz), 6.38 (1H, br m), 4.48 (1H, br m), 3.70 (2H, t, J=5.2 Hz), 3.68-3.63 (10H, m), 3.55-3.53 (2H, m), 3.36 (3H, s), 3.31 (2H, m), 2.97 (3H, d, J=4.8 Hz).

Example 29

Production of 2-{[3-({4-[(2,5,8,11,14-pentaoxahexadecane-16-yl)amino]phenyl}ethynyl)-1H-indazol-6-yl]thio}-N-methylbenzamide (Compound 29)

[Formula 118]

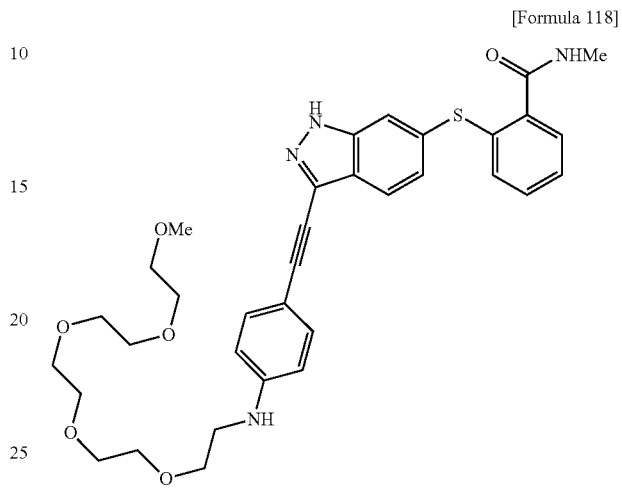

2-{(3-Iodo-1H-indazol-6-yl)thio}-N-methylbenzamide (100.0 mg, 0.24 mmol), N-(4-ethynylphenyl)-2,5,8,11,14-pentaoxahexadecane-16-amine (100.0 mg, 0.28 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (13.8 mg, 9%) as a brown solid.

$^1$H NMR (400 MHz, CDCl$_3$) δ 11.77 (1H, br s), 7.78 (1H, br d, J=8.4 Hz), 7.72 (1H, br s), 7.57-7.54 (1H, m), 7.41 (2H, br d, J=8.6 Hz), 7.23-7.17 (2H, m), 7.16 (1H, dd, J=8.4, 1.6 Hz), 7.09-7.07 (1H, m), 6.56 (2H, br d, J=8.6 Hz), 6.46 (1H, q, J=4.8 Hz), 4.49 (1H, br m), 3.69 (2H, t, J 5.2 Hz), 3.66-3.60 (14H, m), 3.53-3.51 (2H, m), 3.35 (3H, s), 3.30-3.28 (2H, m), 2.96 (3H, d, J=4.8 Hz).

Example 30

Production of 2-[(3-{[5-(3-{2-[2-(2-methoxyethoxy)ethoxy]ethyl}ureido)pyridine-3-yl]ethynyl}-1H-indazol-6-yl)thio]-N-methylbenzamide (Compound 30)

[Formula 119]

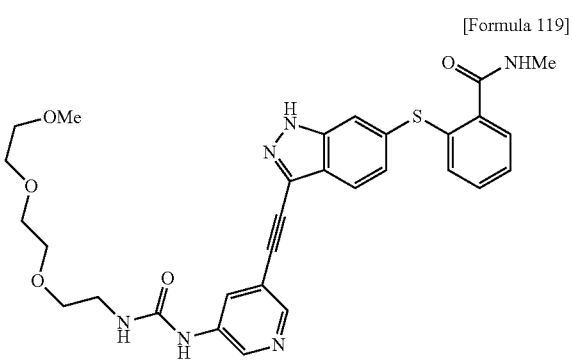 [SMILES: CNC(=O)c1ccccc1Sc1ccc2c(C#Cc3cncc(NC(=O)NCCOCCOCCOC)c3)n[nH]c2c1]

2-{(3-Iodo-1H-indazol-6-yl)thio}-N-methylbenzamide (100.0 mg, 0.24 mmol), 1-(5-ethynylpyridine-3-yl)-3-{2-[2-(2-methoxyethoxy)ethoxy]ethyl}urea (89.1 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (40.1 mg, 28%) as a white powder.

$^1$H NMR (400 MHz, DMSO-d$_6$) δ 13.63 (1H, br s), 8.94 (1H, br s), 8.51 (1H, d, J=2.4 Hz), 8.39 (1H, d, J=2.4 Hz), 8.35 (1H, br q, J=4.4 Hz), 8.21 (1H, br d, J=2.4 Hz), 7.86 (1H, d, J=8.4 Hz), 7.63 (1H, s), 7.49 (1H, dd, J=7.4, 1.6 Hz), 7.35-7.28 (2H, m), 7.21 (1H, br d, J=8.4 Hz), 7.07 (1H, br d, J=7.4 Hz), 6.44 (1H, br t, J=5.2 Hz), 3.54-3.42 (10H, m), 3.30-3.28 (2H, m), 3.24 (3H, s), 2.76 (3H, d, J=4.4 Hz).

Example 31

Production of 2-{[3-({5-[3-(2,5,8,11,14-pentaoxa-hexadecane-16-yl)ureido]pyridine-3-yl}ethynyl)-1H-indazol-6-yl]thio}-N-methylbenzamide (Compound 31)

[Formula 120]

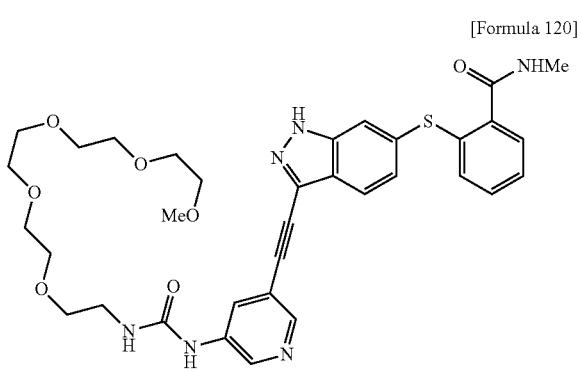 [SMILES: CNC(=O)c1ccccc1Sc1ccc2c(C#Cc3cncc(NC(=O)NCCOCCOCCOCCOCCOC)c3)n[nH]c2c1]

2-{(3-Iodo-1H-indazol-6-yl)thio}-N-methylbenzamide (100.0 mg, 0.24 mmol), 1-(5-ethynylpyridine-3-yl)-3-(2,5,8,11,14-pentaoxahexadecane-16-yl)urea (114.7 mg, 0.29 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (83.8 mg, 51%) as a brown solid.

$^1$H NMR (400 MHz, CD$_3$OD) δ 8.54 (1H, br s), 8.36 (1H, br s), 8.19 (1H, t, J=2.0 Hz), 7.90 (1H, d, J=8.4 Hz), 7.59 (1H, s), 7.49-7.47 (1H, m), 7.37-7.30 (2H, m), 7.27-7.24 (1H, m), 7.21 (1H, dd, J=8.4, 1.6 Hz), 3.65-3.58 (16H, m), 3.51-3.49 (2H, m), 3.41 (2H, br t, J=5.2 Hz), 3.31 (3H, s), 2.85 (3H, s).

Example 32

Production of 2-[(3-{[6-(3-{2-[2-(2-methoxyethoxy)ethoxy] ethyl}ureido)pyridine-3-yl]ethynyl}-1H-indazol-6-yl)thio]-N-methylbenzamide (Compound 32)

[Formula 121]

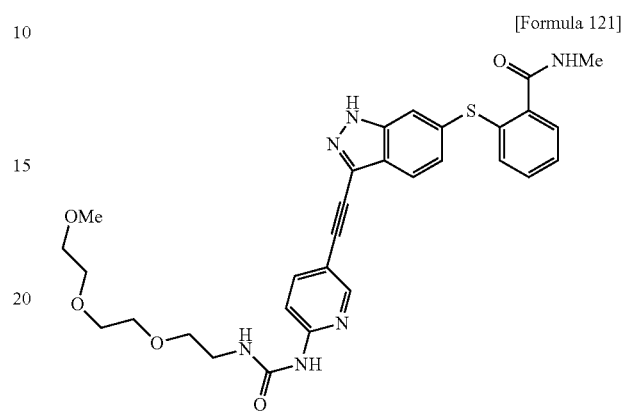

2-{(3-Iodo-1H-indazol-6-yl)thio}-N-methylbenzamide (100.0 mg, 0.24 mmol), 1-(5-ethynylpyridine-2-yl)-3-{2-[2-(2-methoxyethoxy)ethoxy]ethyl}urea (82.4 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (52.9 mg, 37%) as a white powder.

$^1$H NMR (400 MHz, CDCl$_3$) δ 11.24 (1H, br s), 8.85 (1H, br s), 8.40 (1H, d, J=2.0 Hz), 8.16 (1H, br s), 7.75 (1H, d, J=8.4 Hz), 7.73 (1H, dd, J=8.4, 2.0 Hz), 7.63-7.61 (1H, m), 7.57 (1H, br s), 7.31-7.29 (2H, m), 7.24-7.22 (1H, m), 7.19 (1H, dd, J=8.4, 1.4 Hz), 6.99 (1H, br d, J=8.4 Hz), 6.52-6.51 (1H, br m), 3.70-3.66 (8H, m), 3.58-3.55 (4H, m), 3.37 (3H, s), 2.98 (3H, d, J=4.8 Hz).

Example 33

Production of 2-{[3-({6-[3-(2,5,8,11-tetraoxatride-cane-13-yl)ureido]pyridine-3-yl}ethynyl)-1H-inda-zol-6-yl]thio}-N-methylbenzamide (Compound 33)

[Formula 122]

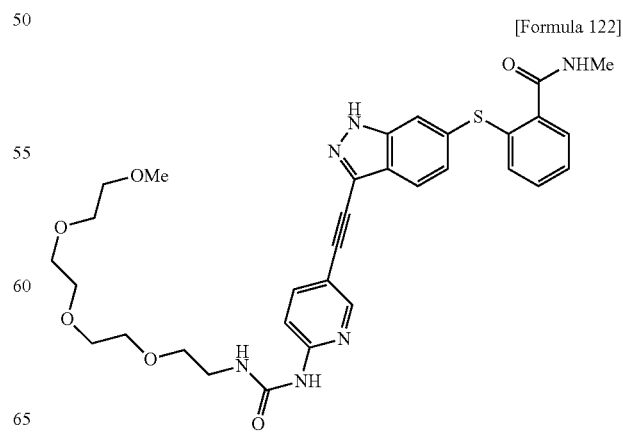

2-{(3-Iodo-1H-indazol-6-yl)thio}-N-methylbenzamide (100.0 mg, 0.24 mmol), 1-(5-ethynylpyridine-2-yl)-3-(2,5,8,11-tetraoxatridecane-13-yl)urea (94.2 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (23.3 mg, 15%) as a pale yellow solid.

$^1$H NMR (400 MHz, CD$_3$OD) δ 8.44 (1H, br d, J=2.4 Hz), 7.84 (1H, dd, J=8.8, 2.4 Hz), 7.76 (1H, br d, J=8.4 Hz), 7.57 (1H, br s), 7.48-7.46 (1H, m), 7.34-7.31 (2H, m), 7.25-7.22 (1H, m), 7.18 (1H, dd, J=8.4, 1.6 Hz), 7.17 (1H, d, J=8.8 Hz), 3.65-3.57 (12H, m), 3.50-3.47 (4H, m), 3.29 (3H, m), 2.85 (3H, s).

Example 34

Production of 2-{[3-({6-[3-(2,5,8,11,14-pentaoxahexadecane-16-yl)ureido]pyridine-3-yl}ethynyl)-1H-indazol-6-yl]thio}-N-methylbenzamide (Compound 34)

[Formula 123]

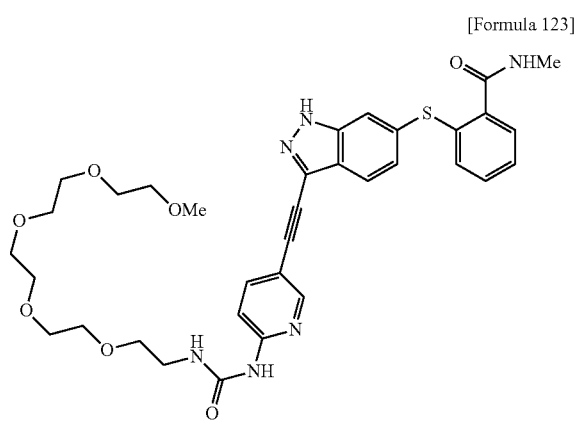 [SMILES: CNC(=O)c1ccccc1Sc1ccc2c(C#Cc3ccc(NC(=O)NCCOCCOCCOCCOCCOC)nc3)n[nH]c2c1]

2-{(3-Iodo-1H-indazol-6-yl)thio}-N-methylbenzamide (100.0 mg, 0.24 mmol), 1-(5-ethynylpyridine-2-yl)-3-(2,5,8,11,14-pentaoxahexadecane-16-yl)urea (106.0 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (16.9 mg, 10%) as a pale yellow solid.

$^1$H NMR (400 MHz, CDCl$_3$) δ 11.93 (1H, s), 8.95 (1H, br s), 8.75 (1H, s), 8.38 (1H, d, J=2.0 Hz), 7.74 (1H, d, J=8.0 Hz), 7.71 (1H, dd, J=8.8, 2.0 Hz), 7.65 (1H, br s), 7.59-7.57 (1H, m), 7.26-7.23 (2H, m), 7.18-7.16 (2H, m), 7.03 (1H, d, J=8.8 Hz), 6.54 (1H, br q, J=4.8 Hz), 3.64-3.56 (18H, m), 3.52-3.50 (2H, m), 3.33 (3H, m), 2.98 (3H, d, J=4.8 Hz).

Example 35

Production of 2-[(3-{[5-(3-{2-[2-(2-methoxyethoxy)ethoxy]ethyl}ureido)pyridine-2-yl]ethynyl}-1H-indazol-6-yl)thio]-N-methylbenzamide (Compound 35)

[Formula 124]

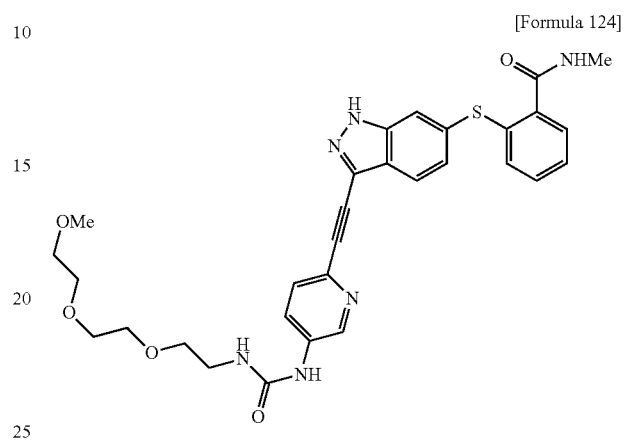

2-{(3-Iodo-1H-indazol-6-yl)thio}-N-methylbenzamide (100.0 mg, 0.24 mmol), 1-(6-ethynylpyridine-3-yl)-3-{2-[2-(2-methoxyethoxy)ethoxy]ethyl}urea (82.4 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (18.3 mg, 13%) as a pale yellow solid.

$^1$H NMR (400 MHz, CDCl$_3$) δ 12.47 (1H, br s), 8.39 (1H, br s), 8.33 (1H, br s), 8.04 (1H, br dd, J=8.4, 2.0 Hz), 7.70 (1H, br d, J=8.4 Hz), 7.63 (1H, br s), 7.51-7.49 (1H, m), 7.38 (1H, br d, J=8.4 Hz), 7.13-7.08 (3H, br m), 7.03-7.01 (1H, m), 6.97-6.96 (1H, br m), 6.21-6.20 (1H, br m), 3.65-3.58 (10H, m), 3.44-3.43 (2H, m), 3.36 (3H, s), 2.92 (3H, br d, J=4.8 Hz).

Example 36

Production of 2-{[3-({5-[3-(2,5,8,11-tetraoxatridecane-13-yl)ureido]pyridine-2-yl}ethynyl)-1H-indazol-6-yl]thio}-N-methylbenzamide (Compound 36)

[Formula 125]

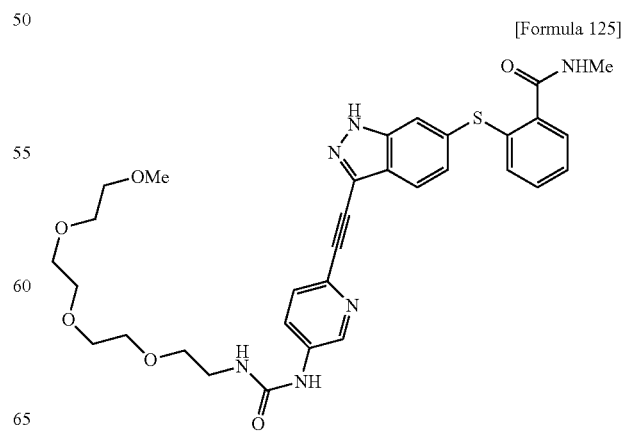

2-{(3-Iodo-1H-indazol-6-yl)thio}-N-methylbenzamide (100.0 mg, 0.24 mmol), 1-(6-ethynylpyridine-3-yl)-3-(2,5,8,11-tetraoxatridecane-13-yl)urea (94.2 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (27.9 mg, 18%) as a pale yellow solid.

$^1$H NMR (400 MHz, CD$_3$OD) δ 8.57 (1H, br d, J=2.4 Hz), 8.00 (1H, dd, J=8.8, 2.4 Hz), 7.82 (1H, br d, J=8.4 Hz), 7.60 (1H, d, J=8.8 Hz), 7.59 (1H, br s), 7.48-7.46 (1H, m), 7.35-7.29 (2H, m), 7.24-7.22 (1H, m), 7.19 (1H, dd, J=8.4, 1.2 Hz), 3.64-3.57 (12H, m), 3.53-3.51 (2H, m), 3.40 (2H, t, J=5.2 Hz), 3.32 (3H, s), 2.92 (3H, s).

Example 37

Production of 2-{[3-({5-[3-(2,5,8,11,14-pentaoxahexadecane-16-yl)ureido]pyridine-2-yl}ethynyl)-1H-indazol-6-yl]thio}-N-methylbenzamide (Compound 37)

[Formula 126]

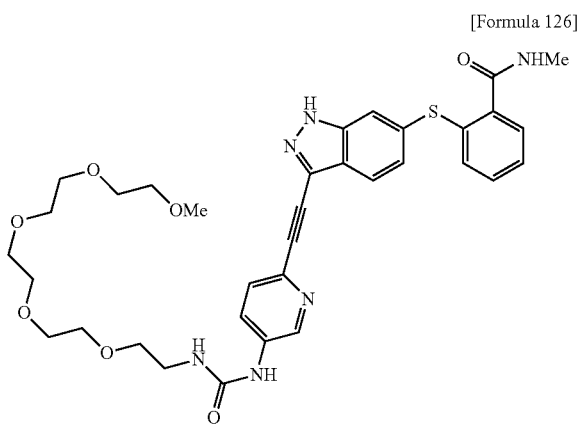 [SMILES: CNC(=O)c1ccccc1Sc1ccc2c(C#Cc3ccc(NC(=O)NCCOCCOCCOCCOCCOC)cn3)n[nH]c2c1]

2-{(3-Iodo-1H-indazol-6-yl)thio}-N-methylbenzamide (100.0 mg, 0.24 mmol), 1-(6-ethynylpyridine-3-yl)-3-(2,5,8,11,14-pentaoxahexadecane-16-yl)urea (106.0 mg, 0.27 mmol), PdCl$_2$(PPh$_3$)$_2$ (8.4 mg, 0.012 mmol), CuI (4.6 mg, 0.024 mmol), N,N-dimethylformamide (2 mL) and N,N-diisopropylethylamine (0.13 mL, 0.72 mmol) were used as raw materials, and treated in the same way as Example 1 to obtain the title compound (33.5 mg, 20%) as a pale yellow solid.

Melting point: 77-78° C.

$^1$H NMR (400 MHz, CDCl$_3$) δ 12.00 (1H, br s), 8.50 (1H, d, J=2.4 Hz), 8.32 (1H, s), 8.12 (1H, dd, J=8.4, 2.4 Hz), 7.80 (1H, d, J=8.4 Hz), 7.67 (1H, br s), 7.58-7.55 (1H, m), 7.45 (1H, d, J=8.4 Hz), 7.22-7.19 (2H, m), 7.16 (1H, dd, J=8.4, 1.6 Hz), 7.11-7.10 (1H, m), 6.69 (1H, br q, J=4.8 Hz), 6.24 (1H, br m), 3.72-3.70 (4H, m), 3.68-3.64 (6H, m), 3.62-3.58 (6H, m), 3.47-3.45 (4H, m), 3.27 (3H, s), 2.96 (3H, d, J=4.8 Hz).

Example 38

Production of N-{5-[(6-{[2-(methylcarbamoyl)phenyl]thio}-1H-indazol-3-yl)ethynyl]pyridine-2-yl}-2,5,8,11-tetraoxatridecane-13-amide (Compound 38)

[Formula 127]

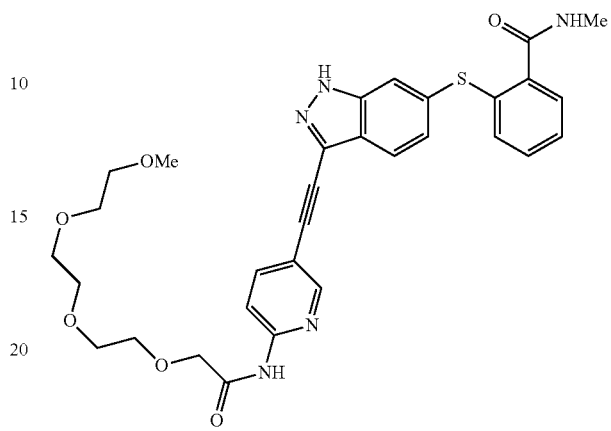

2-{(3-Iodo-1H-indazol-6-yl)thio}-N-methylbenzamide (120.5 mg, 0.29 mmol), N-(5-ethynylpyridine-2-yl)-2,5,8,11-tetraoxatridecane-13-amide (162.3 mg, 0.50 mmol), PdCl$_2$(PPh$_3$)$_2$ (6.5 mg, 0.0093 mmol), CuI (3.5 mg, 0.018 mmol), N,N-dimethylformamide (0.8 mL) and N,N-diisopropylamine (0.15 mL, 0.86 mmol) were used as raw materials, and treated in the same way as Example 1 to obtain the title compound (127.0 g, 71%) as a yellow powder.

$^1$H NMR (400 MHz, DMSO-d$_6$) δ 13.59 (1H, br s), 10.15 (1H, s), 8.63 (1H, dd, J=2.4, 0.8 Hz), 8.36 (1H, q, J=4.8 Hz), 8.18 (1H, dd, J=8.4, 0.8 Hz), 8.10 (1H, dd, J=8.4, 2.4 Hz), 7.87 (1H, dd, J=8.4, 0.8 Hz), 7.61 (1H, br s), 7.50-7.48 (1H, m), 7.33 (1H, td, J=7.6, 2.0 Hz), 7.30 (1H, td, J=7.6, 2.0 Hz), 7.20 (1H, dd, J=8.4, 1.2 Hz), 7.06 (1H, dd, J=7.6, 2.0 Hz), 4.19 (2H, s), 3.70-3.68 (2H, m), 3.62-3.59 (2H, m), 3.58-3.54 (4H, m), 3.53-3.51 (2H, m), 3.43-3.41 (2H, m), 3.23 (3H, s), 2.76 (3H, d, J=4.8 Hz).

Example 39

Production of N-{5-[(6-{[2-(methylcarbamoyl)phenyl]thio}-1H-indazol-3-yl)ethynyl]pyridine-2-yl}-2,5,8,11,14-pentaoxahexadecane-16-amide (Compound 39)

[Formula 128]

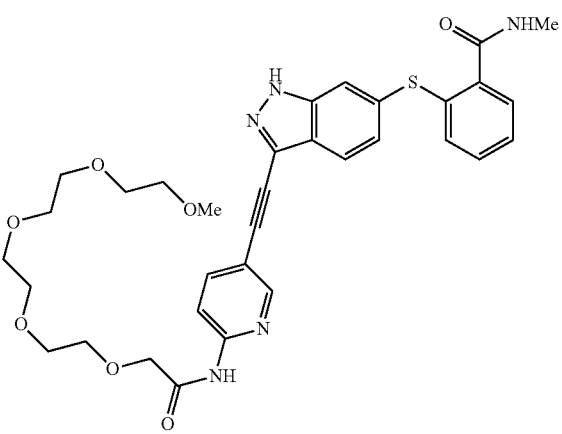

2-{(3-Iodo-1H-indazol-6-yl)thio}-N-methylbenzamide (119.7 mg, 0.29 mmol), N-(5-ethynylpyridine-2-yl)-2,5,8,11,14-pentaoxahexadecane-16-amide (140.2 mg, 0.38 mmol), PdCl$_2$(PPh$_3$)$_2$ (5.6 mg, 0.0080 mmol), CuI (3.0 mg, 0.016 mmol), N,N-dimethylformamide (0.8 mL) and N,N-diisopropylethylamine (0.15 mL, 0.86 mmol) were used as raw materials, and treated in the same way as Example 1 to obtain the title compound (95 mg, 50%) as a white powder.

$^1$H NMR (400 MHz, DMSO-d$_6$) δ 13.59 (1H, br s), 10.15 (1H, s), 8.64 (1H, dd, J=2.4, 0.8 Hz), 8.36 (1H, q, J=4.8 Hz), 8.18 (1H, dd, J=8.4, 0.8 Hz), 8.10 (1H, dd, J=8.4, 2.4 Hz), 7.88 (1H, br d, J=8.4 Hz), 7.62 (1H, br s), 7.51-7.48 (1H, m), 7.33 (1H, td, J=7.6, 1.6 Hz), 7.30 (1H, td, J=7.6, 1.6 Hz), 7.20 (1H, dd, J=8.4, 1.6 Hz), 7.06 (1H, dd, J=7.6, 1.6 Hz), 4.19 (2H, s), 3.71-3.68 (2H, m), 3.62-3.60 (2H, m), 3.59-3.56 (4H, m), 3.54-3.47 (6H, m), 3.43-3.41 (2H, m), 3.23 (3H, s), 2.76 (3H, d, J=4.8 Hz).

Example 40

Production of N-{5-[(6-{[2-(methylcarbamoyl)phenyl]thio}-1H-indazol-3-yl)ethynyl]pyridine-2-yl}-2,5,8,11,14,17-hexaoxanonadecane-19-amide (Compound 40)

[Formula 129]

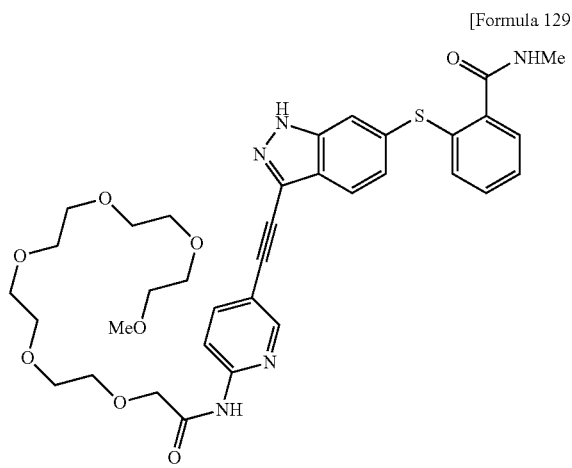 [SMILES: CNC(=O)c1ccccc1Sc1ccc2c(C#Cc3ccc(NC(=O)COCCOCCOCCOCCOCCOC)nc3)n[nH]c2c1]

2-{(3-Iodo-1H-indazol-6-yl)thio}-N-methylbenzamide (108.6 mg, 0.27 mmol), N-(5-ethynylpyridine-2-yl)-2,5,8,11,14,17-hexaoxanonadecane-19-amide (130.2 mg, 0.32 mmol), PdCl$_2$(PPh$_3$)$_2$ (5.4 mg, 0.0077 mmol), CuI (2.7 mg, 0.014 mmol), N,N-dimethylformamide (0.8 mL) and N,N-diisopropylethylamine (0.15 mL, 0.86 mmol) were used as raw materials, and treated in the same way as Example 1 to obtain the title compound (36.0 mg, 20%) as a pale brown powder.

$^1$H NMR (400 MHz, DMSO-d$_6$) δ 13.59 (1H, br s), 10.16 (1H, s), 8.64 (1H, dd, J=2.4, 0.8 Hz), 8.37 (1H, q, J=4.8 Hz), 8.18 (1H, dd, J=8.8, 0.8 Hz), 8.10 (1H, dd, J=8.8, 2.4 Hz), 7.88 (1H, br d, J=8.4 Hz), 7.61 (1H, br s), 7.50-7.48 (1H, m), 7.33 (1H, td, J=7.6, 1.6 Hz), 7.29 (1H, td, J=7.6, 1.6 Hz), 7.20 (1H, dd, J=8.4, 1.6 Hz), 7.07-7.05 (1H, m), 4.19 (2H, s), 3.70-3.68 (2H, m), 3.62-3.60 (2H, m), 3.58-3.55 (4H, m), 3.53-3.48 (10H, m), 3.42-3.40 (2H, m), 3.22 (3H, s), 2.76 (3H, d, J=4.8 Hz).

Example 41

Production of N-{6-[(6-{[2-(methylcarbamoyl)phenyl]thio}-1H-indazol-3-yl)ethynyl]pyridine-2-yl}-2,5,8,11-tetraoxatridecane-13-amide (Compound 41)

[Formula 130]

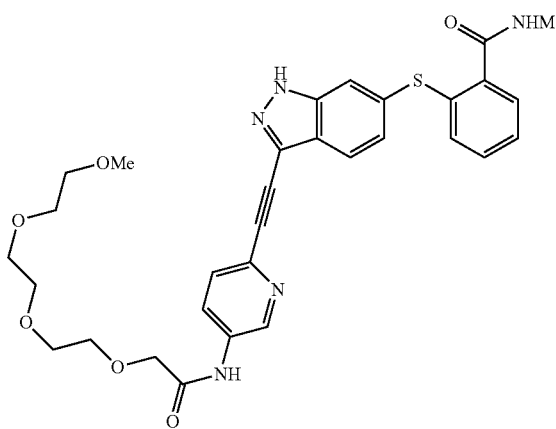

2-{(3-Iodo-1H-indazol-6-yl)thio}-N-methylbenzamide (122.4 mg, 0.30 mmol), N-(6-ethynylpyridine-3-yl)-2,5,8,11-tetraoxatridecane-13-amide (80 mg, 0.25 mmol), PdCl$_2$(PPh$_3$)$_2$ (6.7 mg, 0.0095 mmol), CuI (3.5 mg, 0.018 mmol), N,N-dimethylformamide (0.8 mL) and N,N-diisopropylethylamine (0.15 mL, 0.86 mmol) were used as raw materials, and treated in the same way as Example 1 to obtain the title compound (70.4 mg, 39%) as a pale brown powder.

$^1$H NMR (400 MHz, DMSO-d$_6$) δ 13.63 (1H, br s), 10.08 (1H, s), 8.80 (1H, br d, J=2.4 Hz), 8.36 (1H, q, J=4.8 Hz), 8.20 (1H, dd, J=8.8, 2.4 Hz), 7.83 (1H, dd, J=8.4, 2.4 Hz), 7.73 (1H, d, J=8.8 Hz), 7.62 (1H, br s), 7.50-7.48 (1H, m), 7.33 (1H, td, J=7.6, 2.0 Hz), 7.30 (1H, td, J=7.6, 2.0 Hz), 7.21 (1H, dd, J=8.4, 1.2 Hz), 7.09-7.07 (1H, m), 4.16 (2H, s), 3.71-3.68 (2H, m), 3.65-3.62 (2H, m), 3.58-3.50 (6H, m), 3.43-3.41 (2H, m), 3.23 (3H, s), 2.76 (3H, d, J=4.8 Hz).

Example 42

Production of 2-[(3-{[4-(3-{2-[2-(2-hydroxyethoxy)ethoxy]ethyl}ureido)phenyl]ethynyl}-1H-indazol-6-yl)thio]-N-methylbenzamide (Compound 42)

[Formula 131]

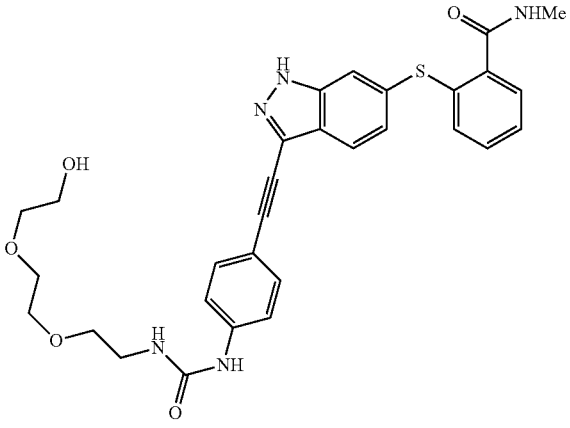

2-{(3-Iodo-1H-indazol-6-yl)thio}-N-methylbenzamide (119.5 mg, 0.29 mmol), 1-(4-ethynyphenyl)-3-{2-[2-(2-hydroxyethoxy)ethoxy]ethyl}urea (93.9 mg, 0.32 mmol), PdCl$_2$(PPh$_3$)$_2$ (10.5 mg, 0.015 mmol), CuI (5.5 mg, 0.029 mmol), acetonitrile (1 mL) and triethylamine (1 mL) were used as raw materials, and treated in the same way as Example 1 to obtain the title compound (36.6 mg, 22%) as a pale yellow solid.

$^1$H NMR (400 MHz, CD$_3$OD) δ 7.75 (1H, br d, J=8.4 Hz), 7.57 (1H, br s), 7.50-7.43 (5H, m), 7.33 (1H, td, J=7.6, 1.6 Hz), 7.29 (1H, td, J=7.6, 1.6 Hz), 7.22 (1H, br d, J=7.6 Hz), 7.16 (1H, dd, J=8.4, 1.2 Hz), 3.70-3.64 (6H, m), 3.60-3.56 (4H, m), 3.39 (2H, t, J=5.2 Hz), 2.85 (3H, s).

Example 43

Production of 2-[(3-{[4-(3-{2-[2-(2-aminoethoxy)ethoxy]ethyl}ureido)phenyl]ethynyl}-1H-indazol-6-yl)thio]-N-methylbenzamide (Compound 43)

[Formula 132]

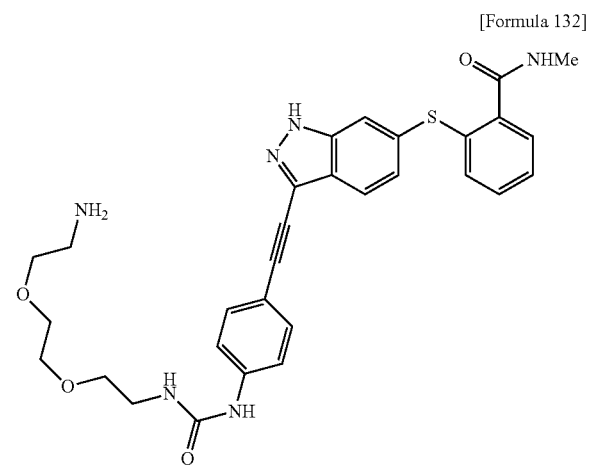 [SMILES: CNC(=O)c1ccccc1Sc1ccc2c(C#Cc3ccc(NC(=O)NCCOCCOCCN)cc3)n[nH]c2c1]

2-{(3-Iodo-1H-indazol-6-yl)thio}-N-methylbenzamide (100.0 mg, 0.24 mmol), 1-{2-[2-(2-aminoethoxy)ethoxy]ethyl}-3-(4-ethynylphenyl)urea (84.5 mg, 0.29 mmol), PdCl$_2$(PPh$_3$)$_2$ (8.6 mg, 0.012 mmol), CuI (4.6 mg, 0.024 mmol), acetonitrile (1 mL) and triethylamine (1 mL) were used as raw materials, and treated in the same way as Example 1 to obtain the title compound (50.4 mg, 37%) as a pale yellow solid.

$^1$H NMR (400 MHz, CD$_3$OD) δ 7.74 (1H, br d, J=8.4 Hz), 7.57 (1H, br s), 7.49-7.41 (5H, m), 7.32 (1H, td, J=7.6, 1.6 Hz), 7.29 (1H, td, J=7.6, 1.6 Hz), 7.21 (1H, br d, J=7.6 Hz), 7.16 (1H, dd, J=8.4, 1.2 Hz), 3.64-3.56 (6H, m), 3.51 (2H, t, J=5.2 Hz), 3.39 (2H, t, J=5.2 Hz), 2.85 (3H, s), 2.78 (2H, br t, J=5.2 Hz).

Example 44

Production of 2-{[3-({4-[3-(2-{2-[2-(dimethylamino)ethoxy]ethoxy}ethyl)ureido]phenyl}ethynyl)-1H-indazol-6-yl]thio}-N-methylbenzamide (Compound 44)

[Formula 133]

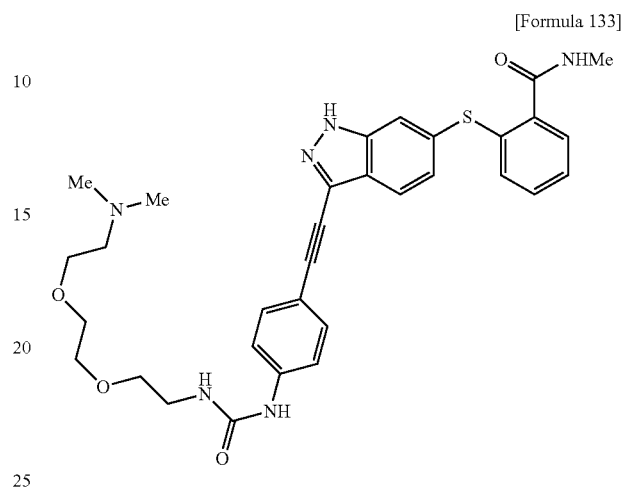

2-{(3-Iodo-1H-indazol-6-yl)thio}-N-methylbenzamide (119.4 mg, 0.29 mmol), 1-(2-{2-[2-(dimethylamino)ethoxy]ethoxy}ethyl)-3-(4-ethynylphenyl)urea (111.9 mg, 0.35 mmol), PdCl$_2$(PPh$_3$)$_2$ (10.5 mg, 0.015 mmol), CuI (5.5 mg, 0.029 mmol), N,N-dimethylformamide (1.2 mL) and N,N-diisopropylethylamine (0.15 mL, 0.86 mmol) were used as raw materials, and treated in the same way as Example 1 to obtain the title compound (36.4 mg, 21%) as a pale yellow solid.

$^1$H NMR (400 MHz, CD$_3$OD) δ 7.75 (1H, br d, J=8.4 Hz), 7.57 (1H, br s), 7.50-7.42 (5H, m), 7.32 (1H, td, J=7.6, 1.6 Hz), 7.29 (1H, td, J=7.6, 1.6 Hz), 7.22 (1H, br d, J=7.6 Hz), 7.17 (1H, dd, J=8.4, 1.2 Hz), 3.62-3.55 (8H, m), 3.38 (2H, t, J=5.6 Hz), 2.85 (3H, s), 2.53 (2H, t, J=5.6 Hz), 2.25 (6H, s).

Example 45

Production of 2-[(3-{[4-(3-{2-[2-(2-acetamidoethoxy)ethoxy]ethyl}ureido)phenyl]ethynyl}-1H-indazol-6-yl)thio]-N-methylbenzamide (Compound 45)

[Formula 134]

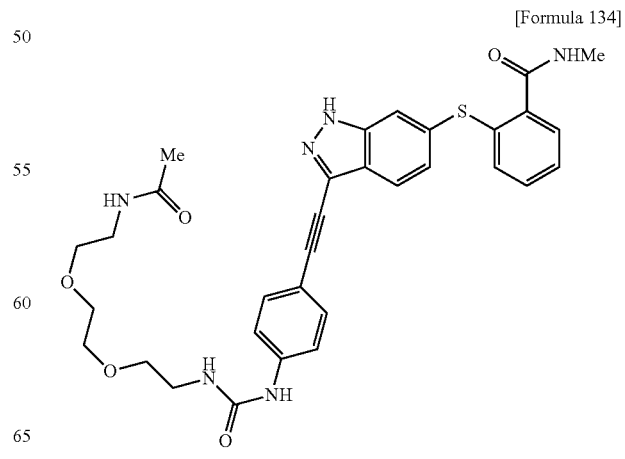

2-{(3-Iodo-1H-indazol-6-yl)thio}-N-methylbenzamide (90 mg, 0.22 mmol), N-[2-(2-{2-[3-(4-ethynylphenyl)ureido]ethoxy}ethoxy)ethyl]acetamide (74 mg, 0.22 mmol), PdCl$_2$(PPh$_3$)$_2$ (7.7 mg, 0.011 mmol), CuI (4.2 mg, 0.022 mmol), acetonitrile (1 mL) and triethylamine (1 mL) were used as raw materials, and treated in the same way as Example 1 to obtain the title compound (31.8 mg, 24%) as a pale yellow solid.

$^1$H NMR (400 MHz, CD$_3$OD) δ 7.76 (1H, d, J=8.4 Hz), 7.57 (1H, s), 7.50-7.43 (5H, m), 7.33 (1H, td, J=7.6, 1.6 Hz), 7.30 (1H, td, J=7.6, 1.6 Hz), 7.23 (1H, br d, J=7.6 Hz), 7.18 (1H, dd, J=8.4, 1.2 Hz), 3.63-3.53 (10H, m), 3.41-3.40 (2H, m), 2.85 (3H, s), 1.94 (3H, s).

Example 46

Production of N-methyl-2-[(3-{[4-(3-{2-[2-(2-morpholinoethoxy)ethoxy]ethyl}ureido)phenyl]ethynyl}-1H-indazol-6-yl)thio]benzamide (Compound 46)

[Formula 135]

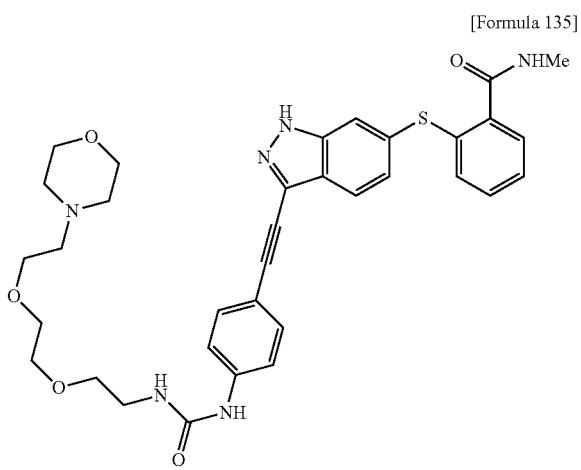 [SMILES: CNC(=O)c1ccccc1Sc1ccc2c(C#Cc3ccc(NC(=O)NCCOCCOCCN4CCOCC4)cc3)n[nH]c2c1]

2-{(3-Iodo-1H-indazol-6-yl)thio}-N-methylbenzamide (108.4 mg, 0.27 mmol), 1-(4-ethynylphenyl)-3-{2-[2-(2-morpholinoethoxy)ethoxy]ethyl}urea (105.2 mg, 0.29 mmol), PdCl$_2$(PPh$_3$)$_2$ (9.3 mg, 0.013 mmol), CuI (5.1 mg, 0.027 mmol), dimethylformamide (1.5 mL) and N,N-diisopropylethylamine (0.14 mL, 0.80 mmol) were used as raw materials, and treated in the same way as Example 1 to obtain the title compound (48.1 mg, 28%) as a pale yellow solid.

$^1$H NMR (400 MHz, CD$_3$OD) δ 7.75 (1H, br d, J=8.4 Hz), 7.57 (1H, br s), 7.50-7.42 (5H, m), 7.32 (1H, td, J=7.6, 1.6 Hz), 7.29 (1H, td, J=7.6, 1.6 Hz), 7.21 (1H, br d, J=7.6 Hz), 7.17 (1H, dd, J=8.4, 1.2 Hz), 3.66-3.59 (10H, m), 3.56 (2H, t, J=5.2 Hz), 3.38 (2H, t, J=5.2 Hz), 2.85 (3H, s), 2.55 (2H, t, J=5.2 Hz), 2.49-2.47 (4H, m).

FORMULATION EXAMPLES

A medicine containing the compound of the present invention as an active ingredient can be produced, for example, by the following formulations.

1. Capsule
   (1) Compound 1 40 mg
   (2) Lactose 70 mg
   (3) Microcrystalline cellulose 9 mg
   (4) Magnesium stearate 1 mg
   1 capsule 120 mg The total amount of (1), (2) and (3) and ½ of (4) were mixed and then granulated, to which the remaining (4) was added, and the whole compounds were encapsulated in a gelatin capsule.

2. Tablet
   (1) Compound 1 40 mg
   (2) Lactose 58 mg
   (3) Corn starch 18 mg
   (4) Microcrystalline cellulose 3.5 mg
   (5) Magnesium stearate 0.5 mg
   1 tablet 120 mg The total amount of (1), (2) and (3), ⅔ of (4) and ½ of (5) were mixed and then granulated. The remaining (4) and (5) were added to this granule, which was pressure-molded into a tablet.

3. Eye drop
   (1) Compound 1 0.1 g
   (2) Sodium dihydrogenphosphate dihydrate 0.35 mg
   (3) Sodium chloride 0.5 mg
   (4) Benzalkonium chloride 0.005 g
   (5) Sodium hydroxide q.s. (pH 7)
   (6) Sterile purified water total volume 100 mL The total amount of (1), (2), (3), (4), (5) and 90 mL of (6) were mixed under aseptic conditions and then appropriate volume of (6) was added to prepare an eye drop.

<Test Example 1> Evaluation of Compounds by VEGF Receptor 2 Kinase Inhibition Assay Compounds 1 to 41 produced in Examples were used as test substances.

Measurement of the kinase inhibitory activity of each compound produced in Examples was conducted using the Off-chip Mobility Shift Assay. For this test, a human recombinant VEGF receptor 2 was prepared in a baculovirus expression system. A recombinant protein was expressed as a GST fusion protein by using 790-1356 amino acids of a cytosolic domain in the VEGF receptor 2 (NP 002244.1) and binding a glutathione-S-transferase (GST) to N-terminal thereof. The expressed GST-VEGF receptor 2 fusion protein was purified using glutathione-sepharose chromatography. In addition, the test substance was dissolved in dimethylsulfoxide to prepare a solution at a concentration about 100 times higher than the test concentration. Furthermore, the solution was diluted with an assay buffer (20 mM HEPES, 0.01% Triton X-100 and 2 mM DTT, pH7.5) by 25 times to prepare a 4-time concentrated test substance solution. In the kinase inhibition assay, CSKtide was used as a substrate. In the kinase reaction, 10 mL of 2-time concentrated VEGF receptor 2 kinase solution, 5 mL of 4-time concentrated test substance solution prepared with the assay buffer, and 5 mL of 4-time concentrated substrate/ATP/metal solution were mixed in wells of a polypropylene 384-well plate, and reacted at room temperature for 1 hour (substrate concentration: CSKtide 1000 nM, ATP concentration: 75 μM, Magnesium: 5 mM). One hour after, 60 mL of Termination Buffer (QuickScout Screening Assist MSA) was added so as to terminate the reaction. After that, the substrate peptide and the phosphorylated peptide in the reaction solution were separated by LabChip3000 system (Caliper Life Science), and the both peptides were quantified. An efficiency of the kinase reaction was evaluated by a ratio of products (P/(P+S)) calculated from a substrate peptide peak height (S) and a phosphorylated peptide peak height (P). The average signal of the control wells containing all the reaction components was designated as 0% inhibition, and the average signal of the background wells (no enzyme added) was designated as 100% inhibition, and an inhibition rate was calculated from the average signal of the test wells of each test substance. An 1050 value was determined by approximating it to a logistic curve of 4 parameters, from the test substance concentration and the inhibition rate by a non-linear least-squares method.

The VEGF receptor 2 inhibitory activities of the compounds 1 to 41 produced in Examples are shown in Table 1 and Table 2. The compounds produced in Examples strongly inhibited the kinase activity of the VEGF receptor 2.

Furthermore, as a reference example, the VEGF receptor 2 kinase inhibition assay was conducted in the same way as described above by using the following compounds A and B. The results are shown in Table 2.

Compound A: 6-[2-(methylcarbamoyl)phenylsulfanyl]-3-E-[2-(pyridine-2-yl)ethenyl]indazole (generic name: Axitinib)

Compound B: 6-[2-(methylcarbamoyl)phenylsulfanyl]-3-[2-(pyridine-2-yl)ethynyl]indazole For the compound A, Axitinib produced by Tocris Bioscience (Catalog number: 4350) was purchased and used. The compound B was synthesized according to a method described in Example 20 of WO 2006/048745.

TABLE 1

| Compounds | Kinase Inhibitory Activity (nM) |
|---|---|
| Compound 1 | 4.0 |
| Compound 2 | 4.7 |
| Compound 3 | 5.9 |
| Compound 4 | 6.7 |
| Compound 5 | 7.7 |
| Compound 6 | 4.5 |
| Compound 7 | 3.4 |
| Compound 8 | 3.1 |
| Compound 9 | 3.9 |
| Compound 10 | 3.9 |
| Compound 11 | 8.8 |
| Compound 12 | 7.2 |
| Compound 13 | 8.9 |
| Compound 14 | 7.6 |
| Compound 15 | 5.8 |
| Compound 16 | 5.2 |
| Compound 17 | 6.4 |
| Compound 18 | 8.0 |
| Compound 19 | 4.6 |
| Compound 20 | 4.2 |
| Compound 21 | 4.9 |
| Compound 22 | 4.8 |
| Compound 23 | 13 |
| Compound 24 | 9.9 |
| Compound 25 | 10 |

TABLE 2

| Compounds | Kinase Inhibitory Activity (nM) |
|---|---|
| Compound 26 | 3.7 |
| Compound 27 | 4.0 |
| Compound 28 | 3.7 |
| Compound 29 | 4.2 |
| Compound 30 | 8.9 |
| Compound 31 | 15 |
| Compound 32 | 5.5 |
| Compound 33 | 9.2 |
| Compound 34 | 11 |
| Compound 35 | 4.2 |
| Compound 36 | 5.7 |
| Compound 37 | 5.9 |
| Compound 38 | 7.9 |
| Compound 39 | 9.7 |
| Compound 40 | 12 |
| Compound 41 | 4.3 |
| Compound 42 | 2.9 |
| Compound 43 | 2.8 |
| Compound 44 | 3.5 |
| Compound 45 | 5.1 |
| Compound 46 | 6.1 |
| Compound A | 0.91 |
| Compound B | 5.5 |

<Test Example 2> the Growth Inhibition Effect of the Compound on the Growth of Human Retinal Microvascular Endothelial (hRMVE) Cells (hRMVEC) by VEGF Stimulation Culture and passage of human retinal microvascular endothelial cells (Cell Systems Corporation, Human Retinal Microvascular Endothelial Cells, catalog number: ACBRI 181) were carried out according to the attached protocol. An adhesion factor solution (Cell Systems Corporation, Attachment Factor) was added to a 96-well plate (Iwaki Glass Co., Ltd.), fitted well, and then removed, so that the wells were coated. Subsequently, cells (hRMVEC) which were suspended in CS-C medium (Cell Systems Corporation, CS-C medium kit, catalog number: CS-4Z0-500R) containing serum, growth factors and Culture Boost were seeded at a density of $2\times10^3$ cells/100 µL/well, and cultured at 37° C. under 5% $CO_2$ for 1 day. After that, the medium was removed from the hRMVEC, washed with PBS twice, and then cultured in CS-C medium (Cell Systems Corporation, CS-C medium kit, catalog number: CS-4Z3-500R) containing 1% FBS and a growth factor for 6 hours. Furthermore, the medium was removed from the hRMVEC again and washed with PBS once, then CS-C medium (Cell Systems Corporation, CS-C medium kit, catalog number: CS-4Z0-5005) containing a recombinant human VEGF (Becton Dickinson and Company) was used, to which a solution prepared by diluting each compound at a threefold common ratio was added at 100 µL/well, and the hRMVEC was cultured for 48 hours.

The cell number was measured by MTT assay (DOJINDO LABORATORIES: Cell Counting Kit-8 was used), and the growth inhibition rate of hRMVEC by the compound was calculated from the following calculation equation.

Cell growth inhibition rate (%)=100−100×(absorbance of well to which the VEGF and compound are added−absorbance of well to which no VEGF is added)/(absorbance of well to which VEGF is added−absorbance of well to which no VEGF is added)

In addition, by using this value of the cell growth inhibition rate, IC50 (M) as a concentration indicating 50% inhibition was calculated from the following calculation formula.

$IC50(M) = 10^{\wedge}(LOG(A/B) \times (50-C)/(D-C) + LOG(B))$

A: Higher one of 2 concentrations which are upper and lower values closest to the 50% inhibition rate
B: Lower one of 2 concentrations which are upper and lower values closest to the 50% inhibition rate
C: Inhibition rate at B
D: Inhibition rate at A Among the compounds produced in Examples, the hRMVE cell growth inhibition activities of representative compounds are shown in Table 3. Furthermore, as a reference example, the hRMVE cell growth inhibition activities were similarly measured for the compound A and compound B used in Test Example 1, and the results are shown in Table 3.

TABLE 3

| Compounds | Cell Growth Inhibition Activity (nM) |
| --- | --- |
| Compound 3 | 11 |
| Compound 8 | 1.2 |
| Compound 13 | 9.3 |
| Compound 16 | 1.2 |
| Compound 20 | 1.7 |
| Compound 25 | 10 |
| Compound 27 | 1.2 |
| Compound 32 | 3.8 |
| Compound 35 | 3.2 |
| Compound 38 | 3.5 |
| Compound 42 | 1.6 |
| Compound 43 | 4.0 |
| Compound 44 | 3.0 |
| Compound 45 | 2.5 |
| Compound 46 | 3.2 |
| Compound A | 0.24 |
| Compound B | 1.6 |

<Test Example 3> Solubility Test 1.0 mL of 0.1% phosphate buffer solution (pH 7.0) was added to 1.00 mg of the compounds produced in Examples. The mixture was subjected to ultrasonic irradiation for 30 seconds, and then shaken at room temperature overnight. The resulting suspension was left at rest at room temperature for 30 minutes, then filtered through a chromatography disc (0.20 μm) to prepare a sample solution. The sample solution and the standard solution were analyzed by LC-MS (product name: ACQUITY UPLC H-CLASS SYSTEM and Xevo TQ-S, produced by Nihon Waters K.K.), and a solubility was calculated from the obtained peak area value by an external standard method.

As a reference example, the solubility test was similarly carried out for the compound A and compound B used in Test Example 1.

[Analytical condition of UPLC]
Column: ACQUITY UPLC (registered trademark) BEH C18, 1.7 μm, 2.1×50 mm (Waters)
Mobile phase: 0.006% formic acid aqueous solution:methanol=40:60 to 60:40
Detection wavelength: 354 nm
Column temperature: 40° C.
Flow rate: 0.25 mL/min
Injection volume: 1.0 μL
Standard solution: 1.00 mg of the compounds produced in Examples were dissolved in methanol (10 mL), and then diluted by 1000 times with methanol to prepare 100 ng/mL of standard solution.

The measurement results of solubilities for the 0.1% phosphate buffer solution (pH 7.0) are shown in Table 4.

TABLE 4

| Compounds | Solubility (μg/mL) |
| --- | --- |
| Compound 4 | 0.31 |
| Compound 5 | 0.99 |
| Compound 8 | 1.0 |
| Compound 9 | 1.2 |
| Compound 10 | 2.5 |
| Compound 16 | 0.27 |
| Compound 17 | 0.38 |
| Compound 18 | 0.86 |
| Compound 22 | 3.3 |
| Compound 27 | 0.48 |
| Compound 28 | 0.17 |
| Compound 29 | 0.89 |
| Compound 30 | 0.58 |
| Compound 31 | 9.9 |
| Compound 34 | 2.6 |
| Compound 35 | 4.4 |
| Compound 36 | 16 |
| Compound 37 | 29 |
| Compound 41 | 0.52 |
| Compound 42 | 3.1 |
| Compound 43 | 32 |
| Compound 44 | 7.6 |
| Compound 45 | 0.56 |
| Compound 46 | 1.4 |
| Compound A | 0.045 |
| Compound B | 0.084 |

<Test Example 4> Photostability Test 1.00 mg of the compounds produced in Examples were dissolved in 10 mL of methanol, then diluted with a water/methanol mixed solution (v/v=1:1) to prepare 10 μg/mL of sample solutions. This sample was left at rest under a white fluorescent lamp (500 Lux) for 6 hours, and then analyzed by HPLC to determine a residual ratio (%) of the compounds.

The analytical conditions of HPLC are as follows. As a reference example, the same experiment was conducted for the compound A used in Test Example 1.

The residual ratios (light stability) are shown in Table 5. The compounds produced in Examples were stable to light in the solution.

[Analytical condition of HPLC]
Column: YMC-Pack ODS-A AA12S05-1506WT, 6.0×150 mm, 5 μm, (YMC CO., LTD.)
Mobile phase: Solution A: a 0.01 v/v % formic acid aqueous solution, Solution B: 0.01 v/v % formic acid-methanol solution, mixing ratio (A:B)=4:6
Detection wavelength: 323 nm (compound 8), 330 nm (compound 37), 354/363 nm (Z form/E form in compound A)
Column temperature: 40° C.
Flow rate: 1.0 mL/min
Injection volume: 20 μL
Standard solution: The sample solution immediately after the preparation was preserved at 4° C., and used as a standard solution.

TABLE 5

| Compounds | Residual Ratio (%) |
| --- | --- |
| Compound 8 | 97.6 |
| Compound 37 | 99.2 |
| Compound A | 75.4 |

<Test Example 5> Drug Penetrating Test to Retina/Choroid

For the compounds 8, 27 and B produced in Examples, drug penetrating concentrations to retina/choroid tissues after instillation were measured. The ophthalmic solution used in this study was prepared by suspending the compound 8, compound 27 or compound A respectively in a phosphate buffer solution (pH 7.0) so that the concentration of the drug is 0.25%, according to the conventional method. In order to measure the drug concentration in the retina/choroid tissues, the eye drop was administered to rabbits (Japanese white rabbit) at 50 μL/eye, the rabbits were euthanized 2 hours after instillation, and the eyeballs were excised. The excised eyeballs were frozen with liquid nitrogen, split into two parts along the equatorial plane, and then the retina/choroid tissues were sampled from the posterior eye segment. In order to extract the compound from the sampled tissues, the tissues were finely cut in methanol to prepare a lysate, and subsequently the lysate was centrifuged to collect the supernatant. To the extracted solution of the compound from the supernatant, an equivalent amount of ultrapure water was added, and the solution was filtered through a membrane filter (0.22 μm), and the filtrate was designated as a final measurement solution. The drug concentration in the filtrate was analyzed by liquid chromatography mass spectrometry (LC/MS/MS), and the compound concentration in the retina/choroid tissues was calculated from the peak area value obtained by an external standard method. Analysis conditions of LC/MS/MS are as below.
[Analytical condition of LC/MS/MS]
Apparatus: ACQUITY UPLC (registered trademark) H-Class system (Waters)
Column: ACQUITY UPLC (registered trademark) BEH C18, 1.7 μm, 2.1×50 mm (Waters)
Mobile phase: 0.006% formic acid aqueous solution:methanol=40:60 (compound 27), 0.006% formic acid aqueous solution:methanol=47:53 (compounds 8 and B)
Detector: ESI probe-equipped tandem quadrupole mass spectrometer Xevo (registered trademark) TQ-S (Waters)
Ionization mode: ESI positive ion
Analysis mode: MRM
Cone voltage: (compound 8) 6 V, (compound 27) 72 V, (compound B) 2 V
Collision energy voltage: 26 eV (compound 8); 26 eV (compound 27); 18 eV (compound B)
Ion transition: m/z 588.12→367.97 (compound 8); m/z 545.18→393.99 (compound 27); m/z 385.07→353.95 (compound B)

The average compound concentrations in the retina/choroid are shown in Table 6. For the compound concentration in the retina/choroid, null hypothesis test was carried out using JMP (registered trademark) (SAS Institute Inc.), the outlier was excluded, and then the average value±standard deviation was used.

TABLE 6

| Compounds | Concentration in Retina/Choroid |
|---|---|
| Compound 8 | 2.60 ± 1.04 ng/g |
| Compound 27 | 1.62 ± 0.68 ng/g |
| Compound B | 0.51 ± 0.10 ng/g |

The drug penetrating concentrations of the compounds 8 and 27 in the retina/choroid were significantly higher than of the compound B (compounds B and 8: n=6, compound 27: n=4, p≤0.05). From the results shown in Table 6, it is apparent that the compound (I) of the present invention has an excellent penetrating property to retina/choroid tissues.

INDUSTRIAL APPLICABILITY

The compound (I) of the present invention and its pharmacologically acceptable salt are useful as a VEGF receptor inhibitor and useful for prevention or treatment of various diseases or conditions involving the receptor. In addition, the compound (I) of the present invention and its pharmacologically acceptable salt have high solubility in aqueous solutions and excellent stability in a solution state, and thus can be used, for example in a form of liquid formulation such as an eye drop. The compound (I) of the present invention and its pharmacologically acceptable salt are useful as medicines or the like for prevention or treatment of retinal diseases accompanying angiogenesis or edema.

What is claimed is:
1. An alkynyl indazole derivative represented by the following general formula (I):

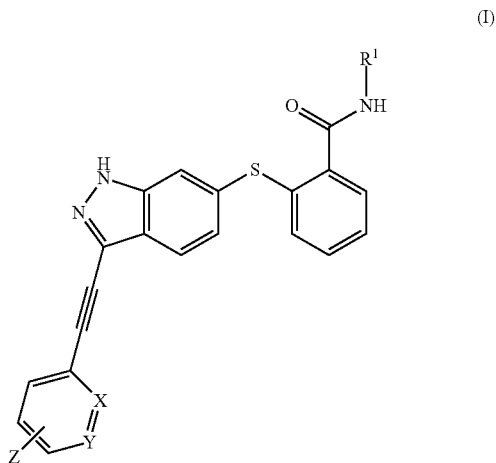

(I)

wherein
  $R^1$ represents a lower alkyl,
  X and Y are the same or different and each represents CH or N, with the proviso that X and Y are not simultaneously N; and
  Z is a group represented by the following general formula (a):

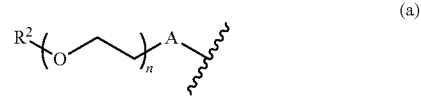

(a)

wherein
  $R^2$ represents a lower alkyl which may have a substituent,
  n is an integer of 1 to 7; and
  A is a partial structure represented by the following formula:

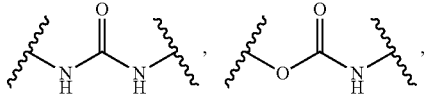

-continued

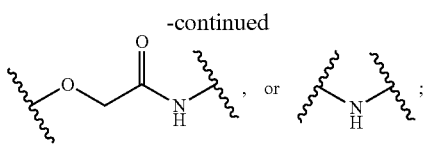

or a pharmaceutically acceptable salt thereof.

2. The alkynyl indazole derivative according to claim 1, or the pharmaceutically acceptable salt thereof, wherein X and Y are simultaneously CH.

3. The alkynyl indazole derivative according to claim 1, or the pharmaceutically acceptable salt thereof, wherein Z is bound in the para-position.

4. The alkynyl indazole derivative according to claim 1, or the pharmaceutically acceptable salt thereof, wherein A is a partial structure represented by the following formula:

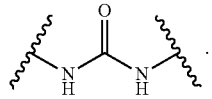

5. A medicine characterized by containing the alkynyl indazole derivative according to claim 1 or the pharmaceutically acceptable salt thereof.

6. The medicine according to claim 5, which is a vascular endothelial cell growth factor (VEGF) receptor tyrosine kinase inhibitor.

7. The medicine according to claim 5, which is used for treatment or prevention of a retinal disease accompanying angiogenesis or edema.

8. The medicine according to claim 7, wherein the retinal disease accompanying angiogenesis or edema is age-related macular degeneration, macular edema, diabetic retinopathy, retinopathy of prematurity, retinal vein occlusion, secondary cataract, myopic choroidal neovascularization, or glaucoma.

9. A method for treating a disease or condition accompanying angiogenesis or edema in a mammal, the method comprising the step of administering the alkynyl indazole derivative according to claim 1, or the pharmaceutically acceptable salt thereof, to the mammal.

10. The method according to claim 9, wherein the disease or condition accompanying angiogenesis or edema to be treated is a retinal disease accompanying angiogenesis or edema.

11. The method according to claim 10, wherein the retinal disease accompanying angiogenesis or edema is age-related macular degeneration, macular edema, diabetic retinopathy, retinopathy of prematurity, retinal vein occlusion, secondary cataract, myopic choroidal neovascularization, or glaucoma.

\* \* \* \* \*